United States Patent
Wang

(10) Patent No.: US 7,745,230 B2
(45) Date of Patent: Jun. 29, 2010

(54) ESTROGEN RECEPTORS AND METHODS OF USE

(75) Inventor: Zhao Yi Wang, Bellevue, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 10/591,199

(22) PCT Filed: Mar. 10, 2005

(86) PCT No.: PCT/US2005/007857

§ 371 (c)(1), (2), (4) Date: Jun. 13, 2007

(87) PCT Pub. No.: WO2005/087811

PCT Pub. Date: Sep. 22, 2005

(65) Prior Publication Data

US 2007/0258895 A1    Nov. 8, 2007

Related U.S. Application Data

(60) Provisional application No. 60/552,067, filed on Mar. 10, 2004, provisional application No. 60/643,469, filed on Jan. 13, 2005.

(51) Int. Cl.
G01N 33/53 (2006.01)
C12P 21/08 (2006.01)
C07K 16/00 (2006.01)

(52) U.S. Cl. .................... 436/548; 436/547; 435/7.1; 530/388.1; 530/389.1; 530/388.15; 530/387.3; 530/387.1; 530/388.24

(58) Field of Classification Search .................. None
See application file for complete search history.

(56) References Cited

U.S. PATENT DOCUMENTS

| 4,036,945 A | 7/1977 | Haber |
| 4,331,647 A | 5/1982 | Goldenberg |
| 4,946,778 A | 8/1990 | Ladner et al. |
| 5,053,133 A | 10/1991 | Klein et al. |
| 5,116,750 A | 5/1992 | Gelfand et al. |
| 5,168,049 A | 12/1992 | Meade et al. |
| 5,223,409 A | 6/1993 | Ladner et al. |
| 5,312,752 A | 5/1994 | Wotiz et al. |
| 5,403,484 A | 4/1995 | Ladner et al. |
| 5,560,922 A | 10/1996 | Chien et al. |
| 5,571,698 A | 11/1996 | Ladner et al. |
| 5,595,887 A | 1/1997 | Coolidge et al. |
| 5,788,983 A | 8/1998 | Chien et al. |
| 6,127,150 A | 10/2000 | Coolidge et al. |
| 6,306,434 B1 | 10/2001 | Hong et al. |
| 6,342,221 B1 | 1/2002 | Thorpe et al. |
| 6,365,146 B1 | 4/2002 | Uhrich |
| 6,534,281 B2 | 3/2003 | Kitajima et al. |
| 6,558,924 B1 | 5/2003 | Stahl et al. |
| 6,664,372 B1 | 12/2003 | Janda et al. |
| 2003/0044412 A1 | 3/2003 | Pietras et al. |
| 2004/0180819 A1 | 9/2004 | Deecher et al. |
| 2007/0015271 A1* | 1/2007 | Rosen et al. ............. 435/252.1 |

FOREIGN PATENT DOCUMENTS

| WO | WO 01/00823 A1 | 1/2001 |
| WO | WO 01/62969 A2 | 8/2001 |
| WO | WO 01/62969 A3 | 8/2001 |
| WO | WO 02/097044 A2 | 12/2002 |
| WO | WO 02/097044 A3 | 12/2002 |
| WO | WO 2004/016653 A2 | 2/2004 |
| WO | WO 2005/087811 A2 | 9/2005 |
| WO | WO 2005/087811 A3 | 9/2005 |

OTHER PUBLICATIONS

Abbondanza et al., "Characterization and Epitope Mapping of a New Panel of Monoclonal Antibodies to Estrogen Receptor," *Steroids*, 1993; 58:4-12.

Åkesson "New approaches to pharmacological treatment of osteoporosis," 2003 *Bulletin of the World Health Organization* 81(9):657-664.

Altucci et al., "17β-Estradiol Induces Cyclin $D_1$ Gene Transcription, $p36^{D_1}$- $p34^{cdk4}$ Complex Activation and $p105^{Rb}$ Phosphorylation During Mitogenic Stimulation of $G_1$-arrested Human Breast Cancer Cells," *Oncogene*, 1996; 12:2315-2324.

Altucci et al., "Estrogen Induces Early and Timed Activation of Cyclin-dependent Kinases 4, 5, and 6 and Increases Cyclin Messenger Ribonucleic Acid Expression in Rat Uterus," *Endocrinology*, 1997; 138:978-984.

American Type Cell Culture. Accession No. Htb-22. Designation Mcf7. Available Online [Retrieved May 2, 2007]. Retrieved from the Internet: <Http://www.atcc.org/common/catalog/numsearch/numresults.cfm>; 4 pgs.

Anderson et al., "BRCA1 Protein Is Linked to the RNA Polymerase Ii Holoenzyme Complex via Rna Helicase A," *Nat Genet.*, 1998; 19:254-256.

"Anti-estrogen Receptor/rat Anti-estrogen Receptor (Clone H222)" Datasheet [Online]. Research Diagnostics, Inc., Concord, Ma, Rev. Mar. 17, 2005 [Retrieved on Oct. 19, 2006]. Retrieved from the Internet:<Url:http://www.researchd.com/rdiabs/estrorec.htm>; 10 pgs.

Aronica et al., "Estrogen Action via the cAMP Signaling Pathway: Stimulation of Adenylate Cyclase and cAMP-regulated Gene Transcription," *Proceedings of the National Academy of Sciences of the United States of America*, 1994; 91:8517-8521.

Bachelier et al., "Effect of Bilateral Oophorectomy on Mammary Tumor Formation in BRCA1 Mutant Mice," *Oncol. Rep.*, 2005; 14:1117-1120.

(Continued)

*Primary Examiner*—Gary B Nickol
*Assistant Examiner*—Shulamith H Shafer
(74) *Attorney, Agent, or Firm*—Mueting Raasch & Gebhardt, P.A.

(57) ABSTRACT

The present invention provides isolated polypeptides having an amino acid sequence having at least 70% identity to SEQ ID NO:20, wherein the polypeptide has ER-α36 activity. The invention further provides methods for identifying agents that bind to such polypeptides, methods for detecting such polypeptides, and methods for altering the activity of such polypeptides. Also provided are antibodies that specifically bind to an amino acid sequence depicted at SEQ ID NO:1, or an immunogenic fragment thereof, and methods for making and using such antibodies.

34 Claims, 26 Drawing Sheets

OTHER PUBLICATIONS

Barany and Merrifield (Gross and Meienhofer, Eds.) *The Peptides, Analysis, Synthesis, Biology*, vol. 2, Academic Press: New York, NY; 1980. Table of Contents, and Chapter 1 Table of Contents, 9 pgs.

Beato et al. "Steroid Hormone Receptors: Many Actors in Search of a Plot." 1995 *Cell* 83:851-857.

Berry et al., "Role of the Two Activating Domains of the Oestrogen Receptor in the Cell-type and Promoter-context Dependent Agonistic Activity of the Anti-oestrogen 4-hydroxytamoxifen," *Embo Journal*, 1990; 9:2811-2818.

Bird et al. "Single-chain Antigen-binding Proteins." 1988 *Science* 242(4877):423-426.

Björnström et al., "Estrogen Receptor-dependent Activation of Ap-1 via Non-genomic Signaling," *Nuclear Receptor*, 2004; 1-11.

Borgna "Contirbution à l'élucidation du mécanisme d'action antioestrogénique et antitumoral du tamoxifène," 1994 *Bull Cancer* 81:29-37. English language abstract only.

Boussif et al., "A Versatile Vector for Gene and Oligonucleotide Transfer into Cells in Culture and in Vivo: Polyethylenimine," *PNAS*, 1995; 92:7297-7301.

Campbell et al., "Phosphatidylinositol 3-kinase/akt-mediated Activation of Estrogen Receptor α: a New Model for Anti-estrogen Resistance," *Journal of Biological Chemistry*, 2001; 276:9817-9824.

Carlomagno et al., "c-*erb*-B2 Overexpression Decreases the Benefit of Adjuvant Tamoxifen in Early-stage Breast Cancer Without Axillary Lymph Node Metastases," *J. Clin. Oncol.*, 1996; 14:2702-2708.

Carell et al., "A Novel Prcedure for the Synthesis of Libraries Containing Small Organic Molecules," 1994 *Angewandte Chemie International Edition English* 33:2059 2061.

Carter et al. "Humanization of an Anti-p185$^{HER2}$ for Human Cancer Therapy." 1992, *PNAS*; 89:4285-4289.

Castilla et al., "Mutations in the BRCA1 Gene Families with Early-onset Breast and Ovarian Cancer," *Nature Genet.*, 1994; 8:387-391.

Castoria et al., "Non-transcriptional Action of Oestradiol and Progestin Triggers Dna Synthesis," *EMBO*, 1999; 18:2500-2510.

Cerillo et al., "The Oestrogen Receptor Regulates NfκB and AP-1 Activity in a Cell-specific Manner," *J. Steroid Biochem. Mol. Biol.*, 1998; 67(2):79-88.

Chen et al., "Rb Associated Protein 46 (RbAp46) Inhibits Transcriptional Transactivation Mediated by BRCA1," *Biochem Biophys Res Commun*, 2001; 284:507-514.

Chen et al., "The C-Jun N-terminal Kinase Pathway and Apoptotic Signaling," *Int. J Oncol.*, 2000; 16:651-662.

Chen et al., "Estrogen Receptor α Mediates the Nongenomic Activation of Endothelial Nitric Oxide Synthase by Estrogen," *Journal of Clinical Investigation*, 1999; 103:401-406.

Cho et al., "An unnatural biopolymer," *Science*, 1993; 261(5126):1303-1305.

Clark et al., "Correlations between estrogen receptor, progesterone receptors, and patient characteristics in human breast cancer," *J. Clin. Oncol.*, 1984; 2:1102-1109.

Clark et al., "Prognostic and predictive factors," *Diseases of the Breast*, vol. 2, Lippincott Williams & Wilkins, Philadelphia, PA 2000; 38:489-514.

Clark-Lewis et al., "16: Chemical Synthesis, Purification, and Folding of C-X-C and C-C chemokines," 1997 *Metho. Enzymol.* 287:233.

Clarke et al., "Cellular and molecular pharmacology of antiestrogen action and resistance," *Pharmacol. Rev.*, 2001; 53:25-71.

Clarke et al., "Dissociation between steroid receptor expression and cell proliferation in the human breast," *Cancer Res.*, 1997; 57:4987-4991.

Clarke et al., "Antiestrogen resistance in breast cancer and the role of estrogen receptor signaling," *Oncogene*, 2003; 22:7316-7339.

Coligan et al., "Unit 9" *Current Protocols in Immunology*, Wiley Interscience, 1991, vol. 3, Table of Contents for vol. 3 and Unit 9, 6 pgs.

Coligan et al. Current Protocols in Immunology, Wiley Interscience, 1995, vol. 1, Table of Contents, publisher's page, and sections 2.4.1, 2.5.1-2.6.7, 2.8.1-2.8.10 and 2.10.1-2.10.4; 1992.

Committee on Methods of Producing Monoclonal Antibodies "Monoclonal Antibody Production" Institute for Laboratory Animal Research, National Research Council: The National Academies Press 1999.

Connor et al., "Circumventing tamoxifen resistance in breast cancers using antiestrogens that induce unique conformational changes in the estrogen receptor," *Cancer Res.*, 2001; 61:2917-2922.

Coopman et al., "Anti-Proliferative and anti-estrogenic affects of ICI 164,384 and ICI 182,780 in 4-OH-Tamoxifen-Resistant human breast-cancer cells," 1994 *Int. J. Cancer* 56:295-300.

Cull et al., "Screening for Receptor Ligands Using Large Libraries of Peptides Linked to the C Terminus of the lac Repressor," *Proc. Natl. Acad Sci. USA*, 1992; 89:1865-1869.

Cwirla et al., "Peptides on Phage: A Vast Library of Peptides for Identifying Ligands," *Proc. Natl. Acad. Sci. USA*, 1990; 87:6378-6382.

Dang et al., "Peroxisome Proliferator-Activated Receptor γ (PPARγ) as a Molecular Target for the Soy Phytoestrogen Genistein," *J. Biol. Chem.*, 2003; 278(2):962-967.

Dauvois et al., "Antiestrogen ICI 164,384 reduces cellular estrogen receptor content by increasing its turnover," *Proc. Natl. Acad. Sci. USA*, 1992; 89:4037-4041.

DeConinck et al., "Transcriptional regulation of estorgen receptor in breast carcinomas," *Mol. Cell Biol.*, 1995; 15:2191-2196.

Denger et al., "ERα gene expression in human primary osteoblasts: evidence for the expression of two receptor proteins," *Molecular Endocrinology*, 2001; 15:2064-2077.

DeWitt et al., "'Diversomers': An Approach to Nonpeptide, Nonoligomeric Chemical Diversity," *Proc. Natl. Acad. Sci. USA*, 1993; 90:6909-6913.

Devlin, "Random peptide libraries: a source of specific protein binding molecules," *Science*, 1990; 249(4967):404-406.

Diaz-Chico et al., "A 46-kDa antigen associated with estrogen receptor in human breast cancer," *J. Steroid Biochem.*, 1988; 30:315-320.

Dobrzycka et al., "Estrogen receptor corepressors—a role in human breast cancer?" *Endocrine Related Cancer*, 2003; 10(4):517-536.

Dotzlaw et al., "Characterization of estrogen receptor variant mRNAs from human breast cancers," *Molecular Endocrinology*, 1992; 6:773-85.

Driggers et al., "Estrogen action and cytoplasmic signaling pathways. Part II: the role of growth factors and phosphorylation in estrogen signaling," *Trends in Endocrinology and Metabolism*, 2002; 13:422-427.

Eckert et al., "Estrogen receptor synthesis and turnover in MCF7 breast cancer cells measured by a density shift technique," *Endocrinology*, 1984; 114:629-637.

Elbashir et al., "Duplexes of 21-nucleotide RNAs mediate RNA interference in cultured mammalian cells," *Nature*, 2001; 411:494-498.

Endoh et al., "Purification and identification of p68 RNA helicase acting as a transcriptional coactivator soecific for the activation function of human estrogen receptor alpha," *Mol. Cell Biol.*, 1999; 19:5363-5372.

Engelman et al., "Recombinant expression of caveolin-1 in oncogenically transformed cells abrogates anchorage-independent growth," *The Journal of Biological Chemistry*, 1997; 272:16374-16381.

Engelman et al., "Reciprocal regulation of neu tyrosine kinase activity and caveolin-1 protein expression in vitro and in vivo. Implications for human breast cancer," *The Journal of Biological Chemistry*, 1998; 273:20448-20455.

Engelman et al., "p42/44 MAP kinase-dependent and -independent signaling pathways regulate caveolin-1 gene expression," *The Journal of Biological Chemistry*, 1999; 274:32333-32341.

Erb et al., "Recursive Deconvolution of Cominatorial Chemical Libraries," *PNAS*, 1994; 91:11422.

"ERK Antibodies" datasheet [online]. Santa Cruz Biotechnology, Inc., Santa Cruz, CA, © 2006 Santa Cruz Biotechnology, Inc. [retrieved on Oct. 17, 2006]. Retrieved from the Internet <URL:http://www.scbt.com/table.php?table=ERK> and http://www.scbt.com/product.php?datasheet=94>; 2 pgs.

Evans et al., "Design of nonpeptidal ligands for a peptide receptor: cholecystokinin antagonists," *J. Med. Chem.*, 1987; 30(7):1229-1239.

Evans et al., "Reciprocal Antagonism Between Estrogen Receptor and NF-κb Activity in Vivo," *Circ. Res.*, 2001; 89:823-830.

Fan et al., "BRCA1 inhibition of estrogen receptor signaling in transfected cells," *Science*, 1999; 284:1354-1356.

Fan et al., "Role of direct interaction in BRCA1 inhibition of estrogen receptor activity," *Oncogene*, 2001; 20:77-87.

Farhat et al., "The vascular protective effects of estrogen," *FASEB J.*, 1996; 10:615-624.

Fauchere, "Elements for the rational design of peptide drugs," *J. Adv. Drug Res.*, 1986; 15:29-69.

Fawell et al., "Inhibition of estrogen receptor-DNA binding by the "pure" antiestrogen ICI 164,384 appears to be mediated by impaired recepto dimerization," *Proc. Natl. Acad. Sci. USA*, 1990; 87:6883-6887.

Feigelson et al., "Estrogens and breast cancer," *Carcinogenesis*, 1996; 17:2279-2284.

Felici, "Selection of antibody ligands from a large library of oligopeptides expressed on a multivalent exposition vector," *J. Mol. Biol.*, 1991; 222(2):301-310.

Ferguson et al., "Demethylation of the estrogen receptor gene in estrogen receptor-negative breast cancer cells can reactivate estrogen receptor gene expression," *Cancer Res.*, 1995; 55:2279-2283.

Figtree et al., "Truncated estrogen receptor α 46-kDa isoforms in human endothelial cells: Relationship to acute activation of nitric oxide synthase," *Circulation*, 2003; 107:120-126.

Fiucci et al., "Caveolin-1 inhibits anchorage-independent growth, anoikis and invasiveness in MCF-7 human breast cancer cells," *Oncogene*, 2002; 21:2365-75.

Flouriot et al., "Identification of a new isoform of the human estrogen receptor-α (hER-α) that is encoded by distinct transcripts and that is able to repress hER-α activation function 1," *EMBO*, 2000; 19:4688-4700.

Flouriot et al., "Differentially expressed messenger RNA isoforms of the human estrogen receptor-α gene are generated by alternative splicing and promoter usage," *Molecular Endocrinology*, 1998; 12:1939-1954.

Fodor, "Multiplex biochemical assays with biological chips," *Nature*, 1993; 364:555-556.

Foulkes et al., "Estrogen receptor status in BRCA1-and -BRCA2-related breast cancer: The influence of age, grade and histological type," *Clin. Cancer Res.*, 2004; 10:2029-2034.

Frasor et al. "Profiling Estrogen Up- and Down-Regulated Gene Expression in Human Breast Cancer Cells: Insights into Gene Networks and Pathways Underlying Estrogenic Control of Proliferation and Cell Phenotype." 2003 Endocrinology 144:4562.

Friedman et al., "Confirmation of BRCA1 by analysis of germline mutations linked to breast and ovarian-cancer in 10 families," *Nature Genet.*, 1994; 8:399-404.

Futreal et al., "BRCA1 mutations in primary breast and ovarian carcinomas," *Science*, 1994; 266:120-122.

Galbiati et al., "Targeted downregulation of caveolin-1 is sufficient to drive cell transformation and hyperactivate the p42/44 Map kinase cascade," *EMBO*, 1998; 17:6633-6648.

Gallop et al., "Application of Combinatorial Technologies to Drug Technology. 1. Background and Peptide Combinatorial Libraries," *J. Med. Chem.*, 1994; 37(9):1233-1251.

Gottardis et al., "Development of tamoxifen stimulated growth of MCF-7 tumors in athymic mice after a long-term antiestrogen administration," *Cancer Res.*, 1988; 48:5183-5187.

Gram et al. "In Vitro Selection and Affinity Maturation of Antibodies from a Naive Combinatorial Immunoglobulin Library." 1992 PNAS 89:3576-3580.

Green et al., "Human oestrogen receptor cDNA: sequence, expression and homology to v-erb-A," *Nature*, 1986; 320:134-139.

Green et al. "Antigen-specific human monoclonal antibodies from mice engineered with human Ig heavy and light chain YACs," 1994 Nat Gen 7:13-21.

Greenberg et al., "Prostate Cancer in a Transgenic Mouse," *Proc. Natl. Acad. Sci. USA*, 1995; 92:3439-3443.

Greene et al., "Sequence and expression of human estrogen receptor complementary DNA," *Science*, 1986; 231:1150-1154.

Gruvberger et al., "Estrogen receptor status in breast cancer is associated with remarkably distinct gene expression patterns," 2001 *Cancer Research* 61:5979-5984.

Gu et al., "Rapid action of 17β-estradiol on kainate-induced currents in hippocampal neurons lacking intracellular estrogen receptors," *Endocrinology*, 1999; 140:660-666.

Hall et al. "The Multifaceted Mechanisms of Estradiol and Estrogen Receptro Signaling." 2001 J. Biol. Chem. 276(40):36869-36872.

Harlow et al., *Antibodies: A Laboratory Manual*, Cold Spring Harbor Laboratory Press, Cold Spring Harbor, NY, 1988; table of contents and pp. 319, 726.

Harnish et al. "The Role of CBP in Estrogen Receptor Cross-Talk with Nuclear Factor-κB in HepG2 Cells." *Endocrinology*, 2000; 141:3403-3411.

Hayashi et al., "Invasion activating caveolin-1 mutation in human scirrhous breast cancers," *Cancer Research*, 2001; 61:2361-2364.

Hopp et al., "Breast cancer patients with progesterone receptor PR-A-rich tumors have poorer disease-free survival rates," *Clin. Cancer Res.*, 2004; 10:2751-2760.

Hosking et al., "A somatic BRCA1 mutation in an ovarian tumor," *Nature Genet.*, 1995; 9:343-344.

Houghten "The Use of Synthetic Peptide Combinatorial Libraries for the Identification of Bioactive Peptides," *Bio Techniques*, 1992; 13(3):412-421.

Inbar et al. "Localization of Antibody-Combining Sites within the Variable Portions of Heavy and Light Chains." 1972 PNAS 69:2659.

Ishida et al., "RET: a poly A-trap retrovirus vector for reversible disruption and expression monitoring of genes in living cells," *Nucleic Acids Res.*, 1999; 27:580-591.

Jacque et al., "Modulation of HIV-1 replication by RNA interference," *Nature*, 2002; 418:435-438.

Jazaeri et al., "Expression of Estrogen Receptor Alpha MRNA and Protein Variants in Human Endometrial Carcinoma," *Gynecologic Oncology*, 1999; 74(1):38-47.

Jiang et al., "Growth regulation of estrogen receptor-negative breast cancer cells transfected with complementary DNAs for estrogen receptor," *Journal of the National Cancer Institute*, 1992; 84:580-591.

Joel et al., "pp90$^{rsk1}$ regulates estrogen receptor-mediated transcription through phosphorylation of Ser-167," *Molecular and Cellular Biology*, 1998; 273:13317-13323.

Jones et al., "Replacing the complementarity-determining regions in a human antibody with those from a mouse," *Nature*, 1986; 321:522-525.

Jozan et al., "65 and 47 kDa forms of estrogen receptor in human breast cancer: relation with estrogen responsiveness," *Breast Cancer Research and Treatment*, 1991; 19:103-109.

Kametaka et al. "Reduction of CTLL-2 Cytotoxicity by Induction of Apoptosis with a Fas-estrogen Receptor Chimera." 2003 Cancer Sci 94(7):639-643.

Kay et al., *Phage Display of Peptides and Proteins: A Laboratory Manual*, Academic Press, San Diego, CA, 1996; Title page and table of contents only.

Karp et al., "Influence of BRCA1 mutations on nuclear grade and estrogen receptor status of breast carcinoma in Ashkenazi Jewish women," *Cancer*, 1997; 80:435-441.

Katzenellenbogen et al., "Estrogen receptor transcription and transactivation: Estrogen receptor alpha and estrogen receptor beta—regulation by selective estrogen receptor modulators and importance in breast cancer," *Breast Cancer Res.*, 2000; 2:335-344.

Katzenellenbogen et al., "Biomedicine. Defining the 'S' in SERMs," *Science*, 2002; 295(5564):2380-2381.

Keaveney et al., "Sequence analysis of the 5' flanking region of the human estrogen receptor gene," *DNA sequence-J. DNA Seq. Mapping*, 1992; 2:347-358.

Kelly et al., "Rapid action of plasma membrane estrogen receptors," *Trends Endocrinol. Metab.*, 2001; 12:152-156.

Kermani et al. "Production of ScFv antibody fragments following immunization with a phage-displayed fusion protein and analysis of reactivity to surface-exposed epitopes of the protein F of *Pseudomonas aeruginosa* by cytofluorometry." 1995 Hybridoma 14:323-328.

Khan et al., "Estrogen receptor expression of benign breast epithelium and its association with breast cancer," *Cancer Research*, 1994; 54:993-997.

Khoo et al., "Somatic mutations in the BRCA1 gene in the Chinese sporadic breast cancer and ovarian case," *Oncogene*, 1999; 18:4643-4646.

Klinge "Estrogen receptor interaction with estrogen response elements," *Nucleic Acids Research*, 2001; 29:2905-2919.

Kohler and Milstein "Continuous cultures of fused cells secreting antibody of predefined specificity." 1975 Nature 256:495-497.

Koleske et al. "Reduction of caveolin and caveolae in oncogenically transformed cells," *PNAS*, 1995; 92:1381-1385.

Kong et al., "Structure and mechanism of the oestrogen receptor," *Biochemical Society Transactions*, 2003; 31:56-59.

Kousteni et al. "Reversal of Bone Loss in Mice by non-genotropic signaling of sex steroids." 2002 Science 298:843-846.

Kranenburg et al., "Regulating c-Ras function: cholesterol depletion affects caveolin association, GTP loading, and signaling," *Current Biology*, 2001; 11:1880-1884.

Kuiper et al. "Cloning of a novel receptor expressed in rat prostate and ovary," *PNAS*, 1996; 93:5925-5930.

Kurokawa et al., "Inhibition of HER2/neu (erbB-2) and mitogen-activated protein kinases enhances Tamoxifen action against HER-2overexpressing, Tamoxifen-resistant breast cancer cells," *Cancer Re.*, 2000; 60:5887-5894.

Kushner et al., "Construction of cell lines that express high levels of the human estrogen receptor and are killed by estrogens," *Molecular Endocrinology*, 1990; 4:1465-1473.

Kushner et al., "Estrogen receptor pathway to AP-1," *J. Steriod Biochem. Mol. Biol.*, 2000; .74:311-317.

Lakhani et al., "The pathology of familial breast cancer: predictive value of Immunohistochemical markers estrogen receptor, progesterone receptor, HER-2 and p53 in patients with mutations in BRCA1 and BRCA2," *J. Clin. Oncol.*, 2002; 20:2310-2318.

Lam et al., "A New Type of Synthetic Peptide Library for Identifying Ligand-Binding Activity," *Nature*, 1991; 354:82-84.

Lam, "Mini-Review: An Application of Combinatorial Library Methods in Cancer Research and Drug Discvery," *Anti-Cancer Drug Des.*, 1997; 12:145-167.

Lannigan, "Estrogen receptor phosphorylation," *Steroids*, 2003; 68:1-9.

Larrick et al. Methods: A Companion to Methods in Enzymology vol. 2 1991; Title page, publisher's page, and p. 106.

Lawson et al., "Low oestrogen receptor a expression in normal human breast tissue underlies low breast cancer incidence in Japan," *Lancet*, 1999; 351:1787-1788.

Leclercq, "Molecular forms of the estrogen receptor in breast cancer," *Journal of Steroid Biochemistry & Molecular Biology*, 2002; 80:259-272.

Leclercq et al., "Estrogen Receptor Alpha: Impact of Ligands on Intracellular Shuttling and Turnover Rate in Breast Cancer Cells," *Current Cancer Drug Targets*, 2006; 6:39-64.

Lee et al., "Caveolin-1 mutations (P132L and null) and the pathogenesis of breast cancer: caveolin-1 (P132L) behaves in a dominant-negative manner and caveolin-1 (-/-) null mice show mammary epithelial cell hyperplasia," *American Journal of Pathology*, 2002; 161:1357-1369.

Lee et al., "Tumor cell growth inhibition by caveolin re-expression in human breast cancer cells," *Oncogene*, 1998; 16:1391-1397.

Le Mellay et al., "$G\alpha_{q/11}$ and gβγ proteins and membrane signaling of calcitriol and estradiol," *Journal of Cellular Biochemistry*, 1999; 75:138-146.

Levenson et al., "MCF-7: The first hormone-responsive breast cancer cell line," *Cancer Research*, 1997; 51:3071-3078.

Levin, "Integration of the extranuclear and nuclear actions of estrogen," *Molecular Endocrinology*, 2005; 19:1951-1959.

Li et al., "Plasma membrane localization and function of the estrogen receptor α variant (ER46) in human endothelial cells," *PNAS*, 2003; 100:4807-4812.

Liu et al., "Organized endothelial cell surface signal transduction in caveolae distinct from glycosylphosphatidylinositol-anchored protein microdomains," *The Journal of Biological Chemistry*, 1997; 272:7211-7222.

Liu et al., "Estrogen receptor protects p53 from deactivation by human double minute-2," *Cancer Research*, 2000; 60:1810-1814.

Liu et al., "Multiple functions of caveolin-1," *The Journal of Biological Chemistry*, 2002; 277:41295-41298.

Loman et al., "Steroid receptors in hereditary breast carcinomas associated with BRCA1 or BRCA2 mutations or unknown susceptibility genes," *Cancer (Phila.)*, 1998; 83:310-319.

Lonard et al., "The 26S proteasome is required for estrogen receptor α and coactivator turnover and for efficient Er-α transactivation," *Mol. Cell*, 2000; 5:939-948.

Lonberg et al. "Antigen-specific human antibodies from mice comprising four distinct genetic modifications." 1994 Nature 368:856-859.

Macgregor et al., "Basic guide to the mechanisms of antiestrogen action," *Pharmacol. Rev.*, 1998; 50:151-196.

Mandlekar et al., "Activation of caspase-3 and cJun NH2-terminal Kinase-1 signaling pathways in tamoxifen-induced apoptosis of human cancer cells," *Cancer Research*, 2000; 60:5995-6000.

Mandlekar, "Mechanisms of tamoxifen-induced apoptosis," *Apoptosis*, 2001; 6:469-477.

Maret et al., "Expression of the interleukin-6 gene is constitutive and not regulated by estrogen in rat vascular smooth muscle cells in culture." *Endocrinology*, 1999; 140:2876.

Margeat et al., "Ligands differentially modulate the protein interactions of the human estrogen receptors alpha and beta." *J. Mol. Biol.*, 2003; 326:77-92.

Marquez et al., "Membrane-associated binding sites for estrogen contribute to growth regulation of human breast cancer cells," *Oncogene*, 2001; 20:5420-5430.

Marsaud et al., "Various phosphorylation pathways, depending on agonist and antagonist binding to endogenous ERα, differentially affect Erα proteasome-mediated stability, and transcriptional activity in human breast cancer cells," *Molecular Endocrinology*, 2003; 17:2013-2027.

Mayer and Walker (Eds.) Immuno chemical Methods in Cell and Molecular Biology Academic Press: London, England; 1987, Table of Contents only.

McDonnell et al., "Connections and Regulators of the Human Estrogen Receptor." *Science*, 2002; 296:1642-1644.

McGuire, "Prognostic factors in primary breast cancer," *Cancer Surv.*. 1986; 5:527-536.

McKay et al., "Molecular control of immune/inflammatory responses: interactions between nuclear factor-kappa B and steroid receptor-signaling pathways," *Endocr. Rev.*, 1999; 20:435-459.

McPherson et al., "Identification of ERF-1 as a member of the AP2 transcription factor family," *PNAS*, 1997; 94:4342-4347.

Merck Index, Merck Research Laboratories, 13$^{th}$ edition. Whitehouse Station, NJ; 2001; Title page, publisher's page, and table of contents only.

Meienhofer (Li, Ed.) Hormonal Proteins and Peptides vol. 2 Academic Press: city, state; 1973. Title page, publisher's page and table of contents only.

Merajver et al., "Germline BRCA1 mutations and loss of the wildtype allele in tumors from families with early-onset breast and ovarian -cancer," *Clin. Cancer Res.*, 1995;1:539-544.

Merrifield, "Synthesis of a Tetrapeptide," *J. Am. Chem Soc.*, 1963;85:2149-2154.

Migliaccio et al., "Tyrosine kinase/p21$^{ras}$/Map-kinase pathway activation by estradiol-receptor complex in MCF-7 cells," *EMBO Journal*, 1996; 15:1292-1300.

Miki et al., "A strong candidate for the breast and ovarian-cancer susceptibility gene," *Science*, 1994; 266:66-71.

Mokbel "Risk-reducing strategies for breast cancer—a review of recent literature," 2003 Int J Fertility and Women's Med. 48(6):274-277.

Mosbys 2004 Drug Guide Mosbys, Inc: St. Louis, MO; 20047, Title page, Table of contents.

Narod, "Hormonal prevention of hereditary breast cancer," *Ann. NY Acd. Sci.*, 2001; 952:36-43.

National Center for Biotechnology Information, National Library of Medicine, National Institutes of Health, GenBank Locus AL078582, Accession No. AL078582, "Human DNA sequence from clone RP1-13OE4 on chromosome 6q24.2-25.3, complete sequence," [online]. Bethesda, MD [retrieved on Jun. 18, 2007]. Retrieved from the Internet: <http://www.ncbi.nlm.nih.gov/entrez/viewer.fcgi?db=nuccore&id=7161747>; 41 pgs.

National Center for Biotechnology Information, National Library of Medicine, National Institutes of Health, GenBank Locus AL133564, Accession No. AL133564, "*Homo sapiens* mRNA; cDNA DKFZp434J186 (from clone DKFZp434J186)," [online]. Bethesda, MD [retrieved on Oct. 17, 2006]. Retrieved from the Internet: <URL:http://www.ncbi.nlm.nih.gov/entrez/viewer/fcgi?db=nucleotide&val=659 9139>; 2 pgs.

National Center for Biotechnology Information, National Library of Medicine, National Institutes of Health, GenBank Locus AY425004, Accession No. AY425004, "*Homo sapiens* estrogen receptor 1 (ESR1) gene, complete cds," [online]. Bethesda, MD [retrieved on Oct. 17, 2006]. Retrieved from the Internet: <URL:http://www.ncbi.nlm.nih.gov/entrez/viewer.fcgi?db=nucleotide&val=3749 9470>; 131 pgs.

National Center for Biotechnology Information, National Library of Medicine, National Institutes of Health, GenBank Locus BX640939, Accession No. BX640939, "*Homo sapiens* mRNA; cDNA DKFZp686N23123 (from clone DKFZp686N23123)," [online]. Bethesda, MD [retrieved on Oct. 17, 2006]. Retrieved from the Internet: <URL:http://www.ncbi.nlm.nih.gov/entrez/viewer/fcgi?db=nucleotide&val=343 65270>; 3 pgs.

National Center for Biotechnology Information, National Library of Medicine, National Institutes of Health, GenBank Locus HSDJ130E4, Accession No. AL078582, "Human DNA sequence from clone RP1-130E4 on chromosome 6q24.2-25.3 Contains the 3' end of the ESR1 gene for estrogen receptor 1, the 3' end of the synaptic nuclei expressed gene 1b (SYNE-1) (nesprin-1 beta, MYNE1, SYNE1, KIAA0796), complete sequence," [online]. Bethesda, MD [retrieved on Oct. 17, 2006]. Retrieved from the Internet: <URL:http://www.ncbi.nlm.nih.gov/entrez/viewer.fcgi?db=nucleotide&val=7161 747>; 44 pgs.

National Center for Biotechnology Information, National Library of Medicine, National Institutes of Health, GenBank Locus HSM807087, Accession No. BX640939, "*Homo sapiens* mRNA; cDNA DKFZp686N23123 (from clone DKFZp686N23123)," [online]. Bethesda, MD [retrieved on Mar. 2, 2005]. Retrieved from the Internet: <URL:http://www.ncbi.nlm.nih.gov/entrez/viewer/fcgi?db=nucleotide&val=343 65270>; 3 pgs.

National Center for Biotechnology Information, National Library of Medicine, National Institutes of Health, GenBank Locus HumerMCF, Accession No. M12674, "Human estrogen receptor mRNA, complete cds," [online]. Bethesda, MD [retrieved on Oct. 17, 2006]. Retrieved from the Internet: <URL:http://www.ncbi.nlm.nih.gov/entrez/viewer/fcgi?db=nucleotide&val=182 192>; 2 pgs.

National Center for Biotechnology Information, National Library of Medicine, National Institutes of Health, GenBank Locus NT_004441, Accession No. NT_004441, "*Homo sapiens* chromosome 1 working draft sequence segment," [online]. Bethesda, MD [retrieved on Oct. 18, 2007]. Retrieved from the Internet: <http://www.ncbi.nlm.nih.gov/entrez/viewer.fcgi?db=nuccore&id=15296704>; 2 pgs.

National Center for Biotechnology Information, National Library of Medicine, National Institutes of Health, GenBank Locus XM_048940, Accession No. XM- 48940, "*Homo sapens* caveolin 1, caveolae protein 22kD (CAV-1), mRNA," [online]. Bethesda, MD [retrieved on Oct. 18, 2007]. Retrieved from the Internet: <http://www.ncbi.nlm.nih.gov/entrez/viewer.fcgi?db=nuccore&id=14781952>; 2 pgs.

National Center for Biotechnology Information, National Library of Medicine, National Institutes of Health, GenPept Locus AAA52399, Accession No. AAA52399, "estrogen receptor," [online]. Bethesda, MD [retrieved on Oct. 17, 2006]. Retrieved from the Internet: <URL:http://www.ncbi.nlm.nih.gov/entrez/viewer.fcgi?db=protein&val=182193>; 2 pgs.

National Center for Biotechnology Information, National Library of Medicine, National Institutes of Health, GenPept Locus CAE45969, Accession No. CAE45969, "hypothetical protein [*Homo sapiens*]," [online]. Bethesda, MD [retrieved on Feb. 16, 2004]. Retrieved from the Internet: <http://www.ncbi.nlm.nih.gov/entrez/viewer.fcgi?db=protein&id=34365271>; 2 pgs.

Nawaz et al., "Proteasome-dependent degradation of the human estrogen receptor," *Proc. Natl. Acad. Sci. USA*, 1999; 96:1858-1862.

Nicholson et al., "Responses to pure antiestrogens (ICI164384, ICI182780) in estrogen-sensitive and-resistant experimental and clinical breast cancer," *Ann. NY Acad. Sci.*, 1995; 761:148-163.

Nilsson et al., "Mechanisms of estrogen action," *Physiological Reviews*, 2001; 81:1535-1565.

Nirmala et al., "Ubiquitination of the rat uterine estrogen receptor: dependence on estradiol," *Biochem. Biophys. Res. Communi.*, 1995; 213:24-31.

Norris et al., "Identification of a third autonomous activation domain within the human estrogen receptor," *Mol. Endocrinol.*, 1997;11:747-754.

Obrero et al., "Estrogen receptor-dependent and estrogen receptor-independent pathways for Tamoxifen and 4-hydroxytamoxifen-induced programmed cell death," *The Journal of Biological Chemistry*, 2002; 277:45695-45703.

Ogawa et al., "Molecular cloning and characterization of human estrogen receptor betacx: a potential inhibitor of estrogen action in human," *Nucleic Acids Research*, 1998; 26:3505-3512.

Okamoto et al., "Caveolins, a family of scaffolding proteins for organizing 'preassembled signaling complexes' at the plasma membrane," *The Journal of Biological Chemistry*, 1998; 273:5419-5422.

Okuda et al., "Novel splicing events of untranslated first exons in human estrogen receptor α (ER α) gene," *Endocrine Journal*, 2003; 50:97-104.

Olson et al., "Production of a biologically active variant form of recombinant human secretin," *Peptides* 1988; 9:301-307.

Orlandi et al., "Cloning immunoglobulin variable domains for expression by the polymerase chain reaction," *Proc. Nat'l Acad. Sci. USA*, 1989; 86:3833-3837.

Osborne et al., "The value of estrogen and progesterone receptors in the treatment of breast cancer," *Cancer*, 1980; 46(12 Suppl):2884-2888.

Osborne et al., "Human breast cancer in the athymic nude mouse: cytostatic effects of long-term antiestrogen therapy." *Eur. J. Cancer Clin. Oncol.*, 1987; 23:1189-1196.

Pack et al. "Improved bivalent miniantibodies, with identical avidity as whole antibodies, produced by high cell density fermentation of *Escherichia coli*." 1993 BioTech 11:1271.

Page et al., *Diagnostic Histopathology of the Breast*, Edinburgh, UK, 1987, pp. 120-145.

Page et al., "Anatomic markers of human premalignancy and risk of breast cancer," *Cancer*, 1990; 66:1326-1335.

Petersen et al., "Frequency and distribution of estrogen receptor-positive cells in normal, nonlactating human breast tissue," *Cancer Res.*, 1987; 47:5748-5751.

Petz et al., "Fos and Jun inhibit estrogen-induced transcription of the human progesterone receptor gene through an activator protein-1 site," *Mol. Endo.*, 2004; 18:521-532.

Physician's Desk Reference 58th Edition Thompson PDR: Des Moines, IA; 2004 Title page agd Table or contents.

Piccart et al., "Evolution Towards Hormone Independence of the MXT Mouse Mammary Tumor is Associated with a Gradual Change in its Estrogen Receptor Molecular Polymorphism," *Cancer Biochem Biophys.*, 1998; 16:169-182.

Pilat et al., "Characterization of the estrogen receptor transfected MCF10A breast cell line 139B6," *Breast Cancer Res. Treat.*, 1996; 37:253-266.

Pink et al., "A novel 80kDa human estrogen receptor containing a duplication of exons 6 and 7," *Nucleic Acids Research*, 1996; 24:962-969.

Pinzone et al., "Molecular and cellular determinants of estrogen receptor α expression," *Mol. Cell. Bio.*, 2004; 24:4605-4612.

Planas-Silva et al., "Estrogen-dependent cyclin E-cdk2 activation through p21 redistribution," *Molecular and Cellular Biology*, 1997; 17:4059-4069.

Porter "The hydrolysis of rabbit y-globulin and antibodies with crystalline papain" 1959 *Biochem J.* 73:119.

Prall et al., "Estrogen Regulation of Cell Cycle Progression in Breast Cancer Cells," *Journal of Steroid Biochemistry and Molecular Biology*, 1998; 65:169-174.

"Polyvinylidene flouride (PVDF)" product datasheet [online]. Millipore Corporation, Billerica, MA, © 1994-2006 Millipore Corporation or an affiliated company. [retrieved on Oct. 17, 2006]. Retrieved from the Internet: <URL:http://www.millipore.com/catalogue.nsf/docs/C3117>; 4 pgs.

Rao et al., "Antisense RNA to the putative tumor suppressor gene BRCA1 transforms mouse fibroblasts," *Oncogene*, 1996; 12:523-528.

Razandi et al., "Cell membrane and nuclear estrogen receptors (ERs) originate from a single transcript: studies of ERα and ERα expressed in Chinese hamster ovary cells," *Molecular Endocrinology*, 1999; 13:307-319.

Razandi et al., "Plasma membrane estrogen receptors signal to antiapoptosis in breast cancer," *Molecular Endocrinology*, 2000; 14:1434-1447.

Razandi et al., "ERs associate with and regulate the production of caveolin: implications for signaling and cellular actions," *Molecular Endocrinology*, 2002; 16:100-115.

Razani et al., "Caveolin-1, a putative tumor suppressor gene," *Biochemical Society Transactions*, 2001; 29:494-499.

Rebbeck et al., "Prophylactic oophorectomy in carriers of BRCA1 or BRCA2 mutations," *N. Engl. J. Med.*, 2002; 346:1616-1622.

Reid et al., "Human estrogen receptor-α: regulation by synthesis, modification and degradation," *Cellular and Molecular Life Sciences*, 2002; 59:821-31.

Reid et al., "Cyclic, proteasome-mediated turnover of unliganded and liganded ERα on responsive promoters is an integral feature of estrogen signaling," *Mol. Cell*, 2003; 11:695-707.

Riechmann et al., "Reshaping human antibodies for therapy." *Nature*, 1988; 332:323-327.

Ring et al., "Mechanisms of Tamoxifen resistance," *Endocrine-Related Cancer*, 2004; 11:643-658.

Robertson "Estrogen receptor downregulators: New antihormonal therapy for advanced breast cancer," 2002 *Clinical Therapeutics* 24(supp. A): A17-A30.

Rochefort, "Oestrogen- and anti-estrogen-regulated genes in human breast cancer," *Ciba Found Symp.*, 1995; 191:254-265.

Rochefort et al., "Estrogen receptor mediated inhibition of cancer cell invasion and motility: an overview," *J. Steroid Biochem Mol. Biol.*, 1998; 65:163-168.

Rochefort et al., "How to target estrogen receptor-negative breast cancer?" *Endocrine-Related Cancer*, 2003; 10:260-266.

Roger et al., "Dissociated overexpression of cathepsin D and estrogen receptor alpha in preinvasive mammary tumors," *Hum. Pathol.*, 2000; 31:593-600.

Russell et al., "Human vascular endothelial cells contain membrane binding sites for estradiol, which mediate rapid intracellular signaling," *Proceedings of the National Academy of Sciences of the United States of America*, 2000; 97:5930-5935.

Safe, "Transcriptional Activastion of Genes by 17-beta-estradiol Through Estrogen Receptor-Sp1 Interactions." *Vitam. Horm.*, 2001; 62:231-252.

Sager et al., "RNA genetics of breast cancer: maspin as paradigm," *Cold Spring Harb Symp Quant Biol.*, 1994; 59:537-546.

Sambrook et al., *Molecular Cloning: A Laboratory Manual*, 3rd edition, Cold Spring Harbor Press, Cold Spring Harbor, NY, 2001; Title page, publisher's page, and table of contents only.

Sandhu "Protein engineering of antibodies." 1992 *Crit Rev. Biotech.* 12:437-462.

Sanna et al. "Directed selection of recombinant human monoclonal antibodies to herpes simplex virus glycoproteins from phage display libraries," 1995 *PNAS* 92:6439.

Santen et al., "The role of mitogen-activated protein (MAP) kinase in breast cancer," *Journal of Steroid Biochemistry and Molecular Biology*, 2002; 80:239-256.

Schlegel et al., "Caveolin-1 potentiates estrogen receptor α (ERα) signaling, Caveolin-1 drives ligand-independent nuclear translocation and activation of ERα," *J. Biol. Chem.*, 1999; 274:33551-33556.

Schlegel et al., "Ligand-independent activation of oestrogen receptor alpha by caveolin-1," *Biochem. J.*, 1999; 359:203-210.

Schmitz et al. "Phage display: a molecular tool for the generation of antibodies—a review." 2000, *Placenta*, 21(suppA):S106-112.

Schnitzer et al., "Caveolae from luminal plasmalemma of rat lung endothelium: microdomains enriched in caveolin.Ca2+-ATPase, and inositol triphosphate receptor," *PNAS*, 1995; 92:1759-1763.

Scott et al., "Searching for peptide ligands with an epitope library," *Science*, 1990; 249:386-390.

Segars et al., "Estrogen action and cytoplasmic signaling cascades. Part I: membrane-associated signaling complexes," *Trends in Endocrinology and Metabolism*, 2002; 13:349-354.

Shang et al., "Co-factor dynamics and sufficiency in estrogen receptor-regulated transcription," *Cell*, 2000; 103:843-852.

Shang et al., "Molecular determinants for the tissue specificity of SERMs," *Science*, 2002; 295:2465-2468.

Shao and Brown "Advances in estrogen receptor biology: prospects for improvements in targeted breast cancer therapy," 2004 *Breast Cancer Research* 6:39-52.

Sheikh et al., "Why are estrogen-receptor-negative breast cancers more aggressive than the estrogen-receptor-positive breast cancers?" *Invasion and Metastasis*, 1995; 14:329-336.

Shekhar et al., "Transcriptional activation of functional endogenous estrogen receptor gene expression in MCF10AT cells: a model for early breast cancer," *Int. J. Oncol.*, 1998; 13:907-15.

Shekhar et al., "Direct action of estrogen on sequence of progression of human preneoplastic breast disease," *Am. J. Of Pathl.*, 1998; 152:1129-1132.

Shoker et al., "Estrogen receptor-positive proliferating cells in the normal and precancerous breast," *American Journal of Pathology*, 1999; 155:1811-1815.

Simoncini et al., "Interaction of oestrogen receptor with regulatory subunit of phosphatidylinositol 3-kinase," *Nature*, 2000; 407:538-541.

Simoncini et al., "Molecular basis of cell membrane estrogen receptor interaction with phosphatidylinositol 3-kinase in endothelial cells," *Anterioscier Thromb. Vasc. Biol.*, 2003; 193:198-203.

Singer II et al., "Optimal humanization of 1B4, and anti-CD18 murine monoclonal antibody, is achieved by correct choice of human V-region framework sequences." 1993. *J. Immunol*,150:2844-2857.

Smith et al., "Allele losses in the region 17q12-21 in familial breast and ovarian cancer involve the wild-type chromosome," *Nature Genet.*, 1992; 2:128-131.

Smith et al., "cJun overexpression in MCF-7 breast cancer cells produces a tumorigenic, invasive and hormone resistant phenotype," *Oncogene*, 1999; 18:6063-6070.

Sommer et al., 2001 "Estrogen Receptor and Breast Cancer." *Semin. Cancer Biol.*,11:339-352.

Soule et al., "Isolation and characterization of a spontaneously immortalized human breast epithelial cell line, MCF-10," *Cancer Res.*, 1990; 50:6075-6080.

Speir et al., "Competition for p300 Regulates Transcription by Estrogen Receptors and Nuclear Factor-k(beta) in Human Coronary Smooth Muscle Cells." *Circ. Res.*, 2000; 87:1006-1011.

Stewart et al. Solid Phase Peptide Synthesis W.H. Freemand Co: San Francisco, CA, 1969. Title page, publisher's page, and table of contents only.

Stoica et al., "Regulation of estrogen receptor-α gene by epidermal growth factor," *J. Endocrinol.*, 2000; 165:371-378.

Stoner et al., "Hypoxia induces proteasome-dependent degradation of estrogen receptor α in ZR-75-1 breast cancer cells," *Mole. Endocrinol.*, 2002; 16:2231-2242.

Sui et al., "A DNA vector-based RNAi technology to suppress gene expression in mammalian cells." *PNAS*, 2002; 99:5515-5520.

Tamrazi et al. "Estrogen Receptor Dimerization: Ligand Binding Regulates Dimer Affinity and Dimer Dissociation Rate." 2002 Mol. Endocrin. 16(12):2706-2719.

Tanimoto et al., "Regulation of estrogen receptor α gene mediated by promoter B responsible for its enhanced expression in human breast cancer," *Nucleic Acids Res.*, 1999; 27:903-909.

Tatusova et al.1999 "BLAST 2 Sequences, a new tool for comparing protein and nucleotide sequences." *FEMS Microbiol. Lett.*, 174:247-250.

Taylor et al. "Human immunoglobulin transgenes undergo rearrangement, somatic mutation and class switching in mice that lack endogenous IgM."1994 *Int. Immunol* 6:579.

Thompson et al., "Clustal W: improving the sensitivity of progressive multiple sequence alignment through sequence wieghting, position specific gap penalties, and weight matrix choice." *Nucleic Acids Res.*, 1994; 22:4673-4680.

Tomlinson et al., "Characterization of a breast cancer cell line derived from a germ line BRCA1 mutation carrier," *Cancer Res.*, 1998; 58:3237-3242.

Toran-Allerand et al. "ER-X: A novel, plasma-membrane associated, putative estrogen receptor that is regulated during development and after ischemic brain injury." 2002 J. Neuroscience 22:8391-8401.

Toran-Allerand et al. "Minireview: A Plethora of Estrogen Receptors in the Brain: Where Will it End?" 2004 *Endocrinology* 145(3):1069-1074.

Touitou et al., "Stable transfection of the estrogen receptor cDNA into Hela cells induces estrogen responsiveness of endogenous cathepsin D gene but not of cell growth," *Biochemical and Biophysical Research Communications*, 1990; 169:109-115.

Tsai et al., "Akt activation by estrogen in estrogen receptor-negative breast cancer cells," *Cancer Research*, 2001; 61:8390-8392.

Tsukamoto et al., "Expression of the int-1 gene in transgenic mice is associated with mammary gland hyperplasia and adenocarcinomas in male and female mice." *Cell*, 1988; 55:619-625.

Turner et al., "Skeletal effects of estrogen." *Endocr. Rev.*, 1994; 15:275.

Tzukerman et al., "Human estrogen receptor transactivational capacity is determined by both cellular and promoter context and mediated by two functionally distinct intramolecular regions," *Molecular Endocrinology*, 1994; 8:21-30.

van den Heuvel et al., "Distinct roles for cyclin-dependent kinases in cell cycle control," *Science*, 1993; 262:2050-2054.

Verhoeyen et al. "Reshaping human antibodies: grafting antilysozyme activity." 1988 *Science* 239:1534.

Wang, Zhao-Yi "Estrogen Signaling in Normal and Transformed Cell Growth," Grant Abstract, Grant No. 1R01DK070016-01A2. Available online [retrieved Oct. 12, 2006]. National Institute of Diabetes and Digestive and Kidney Diseases, project dates Apr. 1, 2006 to Mar. 30, 2011. Retrieved from the Internet: <URL:http://crisp.cit.nih.gov/crisp/CRISP_LIB.getdoc?textkey=7104684&p_grant_num=1R01DK070016-01A2&p_query=&ticket=25547686&p_audit_session_id=177068781&p_keywords=>; 2 pgs.

Wang, Zhao-Yi "RB Associated Protein 46 and Breast Cancer Progression," Grant Abstract, Grant No. 5ROI CA84328. Available online [retrieved May 29, 2007]. National Cancer Institute, project dates Jul. 1, 2000 to Jun. 30, 2007. Retrieved from the Internet: <http://crisp.cit.nih.gov/CRISP_LIB.getdoc?textkey=6795924&p_grant_num=5R01CA084328-05&p_query=&ticket=37767727&p_audit_session_id=243011768&p_keywords=>; 1 pg.

Wang et al., "Identification, cloning, and expression of human estrogen receptor-α36, a novel variant of human estrogen receptor-α66," *Biochem Biophys Res Commun.*, 2005 336(4):1023-7.

Wang et al., "A variant of estrogen receptor-α, hER-α36: transduction of estrogen- and antiestrogen-dependent membrane-initiated mitogenic signaling," *PNAS*, Jun. 13, 2006; 103(24):9063-9068.

Watters et al., "Rapid membrane effects of steroids in neuroblastoma cells: Effects of estrogen on mitogen activated protein kinase signaling cascade and c-fos immediate early gene transcription," *Endocrinology*, 1997; 138:4030-4033.

Weihua et al., "Update on estrogen signaling." 2003 *FEBS Letters* 546:17-24.

Weisz et al., "Estrogen regulation of proto-Oncogenes coding for Nuclear Proteins," *Critical Reviews in Oncogenesis*, 1993; 4:361-388.

Whitlow et al. Methods: A Companion to Methods in Enzymology vol. 2 1991 p. 97.

Wijayaratne et al., "The human estrogen receptor-α is a ubiquitinated protein whose stability is affected differently by agnists, antagonists and selective estrogen receptor modulators," *J. Biol. Chem.*, 2001; 276:35684-35692.

Williams et al., "Loss of caveolin-1 gene expression accelerates the development of dysplastic mammary lesions in tumor-prone transgenic mice," *Molecular Biology of the Cell*, 2003; 14:1027-1042.

Wilson et al., "Localization of human BRCA1 and its loss in high grade, non-inherited breast carcinomas," *Nature Genet.*, 1999; 21:236-240.

Wilson et al. "The use of mRNA display to select high-affinity protein-binding peptides." 2001 *PNAS* 98:3750.

Yarden et al., "BRCA1 interacts with components of the histone deacetylase complex," *Proc. Natl. Acad. Sci. USA*, 1999; 96:4983-4988.

Yoshida et al., "Role of BRCA1 and BRCA2 as regulators of DNA repair, transcription, and cell cycle in response to DNA damage," *Cancer Sci.*, 2004; 95:866-871.

Zhang et al., "Activation of the p38 Mitogen-activated protein kinase pathway by estrogen or 4-hydroxytamoxifen is coupled to estrogen receptor-induced apoptosis," *The Journal of Biological Chemistry*, 2000; 275:479-468.

Zhang et al., "Caveolin-1 inhibits epidermal growth factor-stimulated lemellipod extension and cell migration in metastatic mammary adenocarcinoma cells (MTLn3). Transformation suppressor effects of adenovirus-mediated gene delivery of caveolin-1," *The Journal of Biological Chemistry*, 2000; 275:20717-20725.

Zhang et al., "Inducible Expression of RbAp46 Activates c-Jun NH2-terminal Kinase Dependent Apoptosis and Suppresses Progressive Growth of Tumor Xenografts in Nude Mice," *Anticancer Research*, 2003; 23:4621-4628.

Zhang et al., "Caveolin-1 Downregulation Activates Estrogen Receptor Alpha Expression and Leads to 17β-estradiol-Stimulated Mammary Tumorigenesis," *Anticancer Research*, 2005; 25:369-376.

Zheng et al., "BRCA1 mediates ligand-independent transcriptional repression of the estrogen receptor," *Proc. Natl. Acad. Sci. USA*, 2001; 98:9587-9592.

Zhu et al. "Generation and Characterization of Transgenic Mice Expressing Tamoxifen-Inducible Cre-Fusion Protein Specifically in Mouse Liver." 2003 World J. Gastroenterology 9(8):1844-1847.

Zschocke et al., "Estrogen receptor αmediated silencing of caveolin gene expression in neuronal cells," *The Journal of Biological Chemistry*, 2002; 277:38772-38780.

Zuckermann et al., "Discovery of nanomolar ligands for 7-transmembrane G-protein-coupled receptors from a diverse N-(substituted)glycine peptoid library." *J. Med. Chem.*, 1994; 37:2678.

Baekkeskov et al., "Glucose stimulates the biosynthesis of a human pancreatic islet cell protein detected by an antiserum against the human erythrocyte glucose transporter" *FEBS*, Jul. 1983; 157(2):331-335.

EMBL Sequence Version Archive [online]. Aug. 28, 2003, "*Homo sapiens* mRNA; cDNA DKFZp686N23123 (from clone DKFZp686N23123)" Accession No. BX640939.1. [Retrieved on Oct. 11, 2007]. Retrieved from the Internet:<URL:http://www.ebi.ac.uk/cgi-bin/sva/sva.pl?session=%2Febi%2 Fextserv%2Foldwork%2FSESSION8521-1192131928-1&index=12 &view=155707327>; 3 pgs.

Bianco et al., "Functional Implications of Antiestrogen Induction of Quinone Reductase: Inhibition of Estrogen-Induced Deoxyribonucleic Acid Damage," *Molecular Endocrinology*, 2003; 17(7):1344-1355.

Kundu et al., "Identification of a Potent Analogue of Nazumamide A Through Iteration of Combinatorial Tetrapeptide Libraries," *Bioorganic & Medicinal Chemistry Letters*, Jul. 7, 1998; 8:1669-1672.

Lindner et al., "Synergistic Antitumor Effects of a Combination of Interferon and Tamoxifen on Estrogen Receptor-Positive and Receptor-Negative Human Tumor Cell Lines In Vivo and In Vitro," *Journal of Interferon and Cytokine Research*, 1997; 17:681-693.

Schulz et al., "Major histocompatibility complex binding and T cell recognition of a viral nonapeptide containing a minimal tetrapeptide," *European Journal of Immunology*, May 1991; 21:1181-1185.

Acs et al., "Immunohistochemical Expression of Erythropoietin and Erythropoietin Receptor in Breast Carcinoma," *Cancer*, Sep. 1, 2002; 95(5):969-981.

Fukazawa et al., "Mitogen-activated Protein/Extracellular Signal-regulated Kinase Kinase (MEK) Inhibitors Restore Anoikis Sensitivity in Human Breast Cancer Cell Lines with a Constitutively Activated Extracellular-regulated Kinase (ERK) Pathway," *Molecular Cancer Therapeutics*, Mar. 2002; 1:303-309.

Renzi, et al., "Erythroprotein down regulates SHP1 and induces a sustained activation of ERK1/ERK2 in primary cortical neurons," *Blood*, Nov. 16, 2001; 98; 1 page—abstract only.

* cited by examiner

1   MAMESAKETRYCAVCNDYASGYHYGVWSCEGCKAFFKRSIQGHNDYMCPATNQCTIDKNR

61  RKSCQACRLRKCYEVGMMKGGIRKDRRGGRMLKHKRQRDDGEGRGEVGSAGDMRAANLV

121 PSPLMIKRSKKNSLALSLTADQMVSALLDAEPPILYSEYDPTRPFSEASMMGLLTNLADRE

181 LVHMINWAKRVPGFVDLTLHDQVHLLECAWLEILMIGLVWRSMEHPGKLLFAPNLLLDRN

241 QGKCVEGMVEIFDMLLATSSRFRMMNLQGEEFVCLKSILLNSGISHVEAKKRILNLHPK

301 IFGNKWFPRV

Figure 10

```
GGTACCCGCGCCCGCGCCGCCCGTCGGGGTGGCCGCCGCGCCCGGCAGGAGGGAGGGAGGG
    Sp1         AP-2                    Krox-20              Sp1
AGGGAGGGAGAAGGGAGAGCCTAGGGAGCTGCGGGAGCCGCGGGACGCGCGACCCGAGGGT
   Sp1     Sp1              AhR
GCGCGCAGGGAGCCCGGGGCGCGCGGCCCAGCCCGGGGGTTCTGCGTGCAGCCCGCGCTGC
               WT1
GTTCAGAGTCAAGTTCTCTCGCCGGGCAGCTGAAAAAAACGTACTCTCCACCCACTTACCGTCCG
  YY1       c-Fos
TGCGAGAGGCAGACCCGAAAGCCCGGGCTTCCTAACAAAACACACGTTGGAAAACCAGACAAAG
                                                        NF-kappaB
CAGCAGTTATTTGTGGGGGAAAACACCTCCAGGCAAATAAACACGGGGCGCTTTGAGTCACTTG
          GR   NF-kappaB    GATA-1                AP-1         c-Fos
                                               c-Jun AP-1    ER
GGAAGGTCTCGCTCTTGGCATTTAAAGTTGGGGGTGTTTGGAGTTAGCAGAGCTCAGCAGAGTTT
  NF-kappa
TATTTATCCTTTTAATGTTTTTGTTTAATGTGCTCCCCAAATTTCCTTTCATCTAGACTATTTGATTG
 TBP
GAAATATGTCAGCTATGATGATGACTTTCTGGGAAGCGATTCCTGTCACCCGCTTTCCCCTCCTC
CCCACCCCACGTCCTGGGGCTTTAGAGAGCGATTGGGAGTTGAATGGGTCTGATTTCGGAGTTA
GCTGGCTGAGTCCGCGCTGGAGCGGATTGCTGGCATGTGACTTCTGACAGCCGGAAATTTGTAG
                                      cDNA→
GTGTCCCGCGAGTTTAAAACAAGCCATATGGAAGCACAAGTGCTTAAAAA
```

Fig. 12a

Figure 12b ctggtatctcacatgtagaagcaaagaagagaatcctgaacttgcatcctaaaatatttggaaacaagtggtttcctcgt
gtctaaagcctctggtcataaggcctcacagtatcctgcagatcatcaaatccgtgtgtggacgtggggacattttgttt
tgaggcagttacatgaccatgggcaagtggattggtctctctggccttcagttttctcatttgcaatgattcaatggttt
gccttaaagtgtcttaagaaggataggatagctacccacaaactttggatcaaattttcttcaaaacatccttcccctga
ctttaaaatatgccctggcaaccaacactcaacacccgtagctagatgagttataacagagtgactgaagagagctccca
caattcctagttattaaatacctgactaattttcattaggagacatttaagaactttagtgatgggaagatttacatata
taattgatagtacaatctgacagagctgaatagctcctgtttgtcaactgttaaattctttgtgcaattaggtcaaagat
caagatcaaaacaagggctgcccattgacctgttcactcctgagaaaaatggcaaaccattgaatcataaatcatgacag
ccaaaataattttaggatattaatgcacccctcatctttgcaagtgagaaaactgaaggccagagagactaatttacttg
cccattttgataaaaatgtcaccatttacagaatgtggactcctatgttggagtctgttgaaggacatggcacatttaa
cagcatcagagcatttttattaaaatttaatttgtgcatgacttctaatgctgaagaacgccaagctaggaagaagtca
tgggctgagatggggacagagagaacacacaatattcagtgactgtccgtgcagctggctgcccttgaaaatatccgaac
tatccactgggaaaatgcctgtcccctggggtaattaccagagtttcaacatgcccaaagctgcctcatcttcagggggg
aacttgttctagcgatttagtatcaagaagctaatggtcccagggaaagggttatttttaatatttagctactgtgcta
aaaatcacctaagtttctagagtcttgggaaatttcataagggaaagaacaaaggcaacttgttgactacccactggtca
ttctcctctggtcttattacatacatggatgccagtttagattgtgtttatataggaaaatttaaatgtgtgagcctcct
taaggaacatcatcaatacagatatatcagatagttctgtccagcaaaaaacgtgcttatttgctacaagtaaattttta
tttatttttctcacttccctcactccttcaaatttccaggtaaatagctgcccaggagttgcttcatctctgtcccaaaa
tacctagacaattgcgggataaggagaatggcagggagggagtagtggctaaaatcacaccttcaaaagaaagtgtgta
ggacacacaattgtgagaagtctgaatgccatgcacatagggtatgactcactttgaaaattgtttataatcaaggaaat
gaaaatgagttaatttcgtgcatgcatcatttaaagccaaatgagaagaaacttctaatttattttgttacttttcggct
aacactggcagtatgtaacagatttattttgcagaaacatctagattgtccgtgatcttgatcctgcccttatgtgtctt
gtctttgaaacccagtgtttcctggatatatggttcaggagacaagtttccagaatcaagttaggacccaggtcttcttt
ttttccaaaccaaacattcttgctaatcctaaactacctgaggcagcctgtggtggcctcagctctaaaaccattgttta
aaggcttctacccatcaatggcccttcagcagagtggtacggttaacgggggtagggtctggagtcaggggagacctgggt
tcaaatcctacatctttacacctctaatccccagtgtccttgtctataaattgggaatatagccatgtcatgggattctt
gtgagggttaaatgaggtaaaacacatacaatgcttagcatgtatacaattaagcactaaataattgaaacacattaagt
actaaatgaatgtcagcagcttatcactattatctgtataatgataccaagggtgtgccgactcatacccttaggggttg
gctggattcggcctttctctcgggaaaacatacctgatttattaatagtgctttcaagcatgtgataaatttctcaaac
tgcctgtcttgttccctagaaacaccaggaaggcctacctcaaatagcaacagagaaacctatcggagccttacctaca
gctttccttggggcacgggtgagcaatctgccttagaggggagaggctctgtgctgaggctctttgaatgctttgaataa
atagatccccagataatgaaaagacttcaaaacaaattctacaagaaactgagtagtgtttatagtgaggccctagtgta
catgcaaaaaaccccactgccccttgcttaaatgtatctgattaacttgaatacattttaaatgagggctttttttccc
tctttcagtgtttcggccagtcatttgccacttctcattccatcttagttctctgtaaagaaggtgccagagacctaagg
tgcccaaggcaattttgcattttacaattctaagctttagaatgaagtcatcaatttgctacatccggactacagtgcaa
ttattccttgccttgctggaaattggagtgaaatctttctagctgtcaatttcaactcagttgcagtagtgttttgaag
aattaatggcgataaggttagaaaattttaagtcaaacgtagggaaaaagtaccagctagaccatcataagcatttgctt
tgaaagcatgcttctaaagtgtgtttaacctcaaataacagtcacaaatatggttattatgaatgtatgcacagatttt
atgtttctaattttaagaagttctagggagctccctgtaacgatttagggaatctctagattctgatatactgcaagtct
tttaatggtaggaatcacattgaattaattttgtaggcccagggcctaaatttagtaggtgttcagtacctattggcatc
aattcatatgtaggtttaaaatactgtatgaagatacagaatcaccaccatcaaatcaaattgaaatatgtaacaggcta
gtataatattaacatctgactttaaacaacaacaaagaaaccaaatgagtaactcctcccttcaaactaatagtcagttt
cttccaactcagtctctttctcctctcaggaagaatgcgtatctaaaaatttcccattgcagactgctggaaacaacatt
ctaaactatttatgcttctgcaataacctttccaatttgctggaccagtgcaagattaaacacgagatatctcaagtctc aatgtaaaggaacaccacgacagcctggactgtgggtgaagttcattcttccccagcagactctgcctttcattctcggg
gttgggtgtgccccaaacagaggtaccgacggtaacgaagcccaagaatgttcaaccacaacctgtctgtgaaggtgttg
gatgacgtttgccattcaggtgaagattatttatgttccagtcccacctgagtagcaaagtgaacactgtgctgaatgct
cagaaagatgttaatgaaccgtgctggacagagcagagctgaaaggcgccttgcgagtgtcgtagtgagaatgtggctgt
cccagctgcaaagccctgttaggaggcatgaggaagcacttgctgccctaagaaacgatgccttcgacattttcaaaaga
tctatgtggctgtctgaaacaatgcggagagcagatagacgcaatatttgggaaccaaagagtgactgctgttggcgttg
catcataacataagcgctttccccttctcgtcactatcatttgtatcaaccaaagaactgatctctggtatcctcgaag
gaatgctgtggggatattcttcatctctgttcatggtacatcagcaatttgtggggaaaagatggactatataacacaat
gatctgcctaaaagaaactgtctctacttataggggggctgagcaaaccttagagcatctgcggatgctcgtcattatctt
caaaagtccccaagagttttctccatactttattattgctattttgtttaggctagaaaaaaaaaaaactcataaaatt
gtcttcaaaccaaaccaaaggaaaaaaaaaaaaaaaaaaa

Figure 12b (part 2)

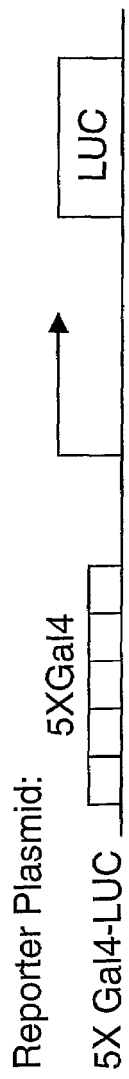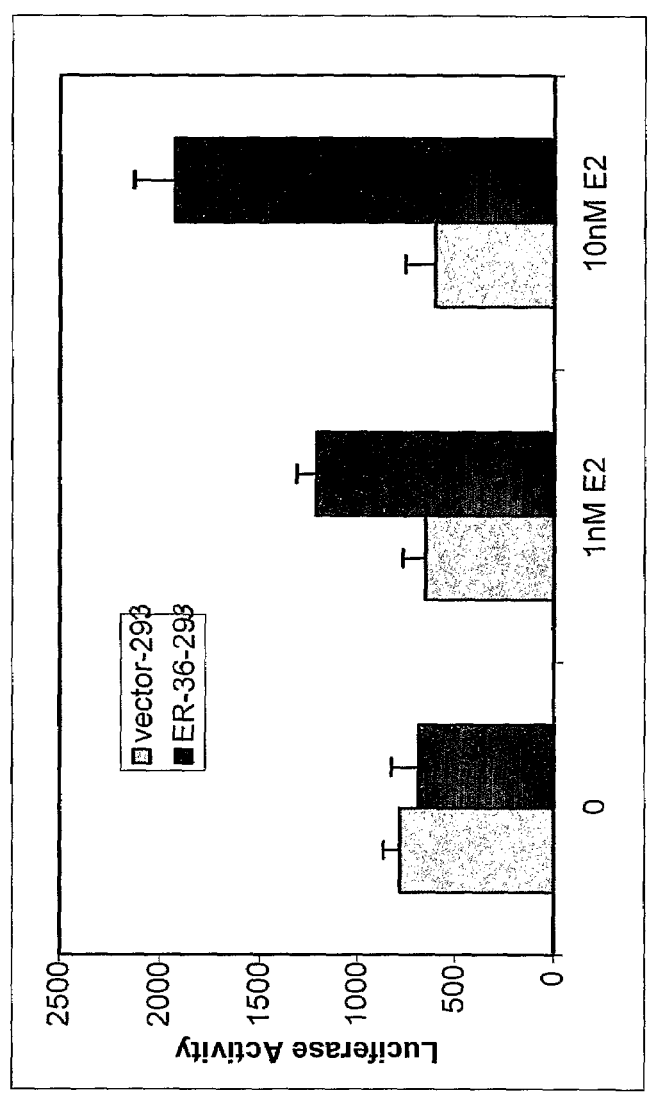
Figure 16a

ESTROGEN RECEPTORS AND METHODS OF USE

CONTINUING APPLICATION DATA

This application claims the benefit of U.S. Provisional Application Ser. No. 60/552,067, filed 10 Mar. 2004, and 60/643,469, filed 13 Jan. 2005, each of which is incorporated by reference herein.

GOVERNMENT FUNDING

The invention described herein was developed with support from the Department of Health and Human Services under Grant Number CA84328. The U.S. Government has certain rights in the invention.

BACKGROUND OF THE INVENTION

Estrogen is a generic term for steroid compounds that are formed in the ovary, the testis, and possibly the adrenal cortex. Examples of estrogens and compounds having estrogen activity include diethylstilbestrol, fosfestrol, hexestrol, polyestradiol phosphate, broparoestrol, chlorotrianisene, dienestrol, diethylstilbestrol, methestrol, colpormon, equilenin, equilin, estradiol, estriol, estrone, ethinyl estradiol, mestranol, mexestrol, quinestradiol and quinestrol. Estrogens regulate diverse physiological processes in reproductive tissues and in mammary, cardiovascular, bone, liver, and brain tissues. Estrogens are also used in oral contraceptives. Other uses for estrogens include the relief of the discomforts of menopause, inhibition of lactation, and treatment of osteoporosis, threatened abortion, and various functional ovarian disorders. Anti-estrogens are used to treat metastatic breast carcinoma and advanced prostate cancer.

The effects of estrogens are mediated via estrogen receptors. The first estrogen receptor (ER) was cloned in 1986 (Green et. al., Nature, 320:134 (1986) and Greene et. al., Science, 231:1150 (1986)). Until 1995, it was assumed that there was only one estrogen receptor responsible for all of the physiological and pharmacological effects of natural and synthetic estrogens and antiestrogens. However, in 1995, a second estrogen receptor was cloned (Kuiper et. al., PNAS, 93:5925 (1996)). The first estrogen receptor discovered is now called estrogen receptor-alpha (ER-α) and the second estrogen receptor is called estrogen receptor-beta (ER-β).

ER-α and ER-β share a common structural architecture (Zhang et. al., FEBS Letters, 546:17 (2003) and Kong et. al., Biochem. Soc. Trans., 31:56 (2003)). Both are composed of three independent but interacting functional domains: the N-terminal A/B domain, the C or DNA-binding domain, and the D/E/F or ligand-binding domain (FIG. 1). The N-terminal domain of ER-α encodes a ligand-independent activation function (AF-1), a region involved in interaction with co-activators, and transcriptional activation of target genes. The DNA-binding domain or C domain contains a two zinc-finger structure, which plays an important role in receptor dimerization and binding to specific DNA sequences. The C-terminal D/E/F domain is a ligand-binding domain that mediates ligand binding, receptor dimerization, nuclear translocation, and a ligand-dependent transactivation function (AF-2). The relative contributions that both AF-1 and AF-2 exert on transcriptional control vary in a cell-specific and DNA promoter-specific manner (Berry et. al., EMBO J., 9:2811 (1990) and Tzukerman et. al., Mol. Endocrin., 8:21 (1994)).

A 46-kDa ER-α isoform lacking the first 173 amino acids of the full-length gene product of the ER-α gene (A/B or AF-1 domain) was shown to be derived from alternative splicing of the ER-α gene by skipping exon 1 (Flouriot et. al., EMBO J., 19:4688 (2000)). This alternative splicing event generates an mRNA that has an AUG in a favorable Kozak sequence for translation initiation in frame with the remainder of the original open reading frame. Therefore, this new isoform of ER-α was named as ER-α46 and the original one was named ER-α66 (Flouriot et. al., EMBO J., 19:4688 (2000)). ER-α46 forms homodimers and binds to an estrogen response element (ERE), and it can also form heterodimers with ER-α66 (Flouriot et. al., EMBO J., 19:4688 (2000)). ER-α46 homodimers show a higher affinity for an ERE than ER-α66 homodimers. Furthermore, the ER-α46/66 heterodimers form preferentially over the ER-α66 homodimers and ER-α46 acts competitively to inhibit transactivation mediated by the AF-1 domain of liganded-ER-α66, but does not effect AF-2-dependent transactivation (Flouriot et. al., EMBO J., 19:4688 (2000)). Therefore, it is thought that ER-α46 is a naturally occurring isoform of ER-α that regulates estrogen signaling mediated by the AF-1 domain of ER-α66.

ER-α is expressed in approximately 15-30% of luminal epithelial cells and not at all in any of the other cell types in the normal human breast. Dual label immunofluorescent techniques revealed that ER-α-expressing cells are separate from those labeled with proliferation markers in both normal human and rodent mammary glands (Clarke et. al., Cancer Res., 57:4987 (1997)). ER-α expression is increased at the very earliest stages of ductal hyperplasia and increases even more with increasing atypia, such that most cells in atypical ductal hyperplasias and in ductal cancer in situ of low and intermediate nuclear grade contain the ER-α (Khan et. al., Cancer Res., 54:993 (1994) and Lawson et. al., Lancet, 351:1787 (1994)). As ER-α expression increases, the inverse relationship between receptor expression and cell proliferation become dysregulated (Shoker et. al., Amer. Jour. Path., 155:1811 (1999)). Approximately 70% of invasive breast carcinomas express the ER-α and most of these tumors contain ER-α-positive proliferating cells (Clarke et. al., Cancer Res., 57:4987 (1997)).

Estrogen receptors are members of the nuclear receptor superfamily of ligand-activated transcription factors that control numerous physiological processes. This control often occurs through the regulation of gene transcription (Katzenellenbogen and Katzenellenbogen, Breast Cancer Res., 2:335 (2000); Hull et al., J. Biol. Chem., 276:36869 (2001); McDonnell and Norris, Science, 296:1642 (2002)). The estrogen receptor utilizes multiple mechanisms to either activate or repress transcription of its target genes. These mechanisms include: (a) direct interaction of the ligand-occupied receptor with DNA at estrogen response elements followed by recruitment of transcriptional coregulator or mediator complexes, (b) interaction of the ligand-occupied ER with other transcription factors such as AP-1 (Kushner at al., J. Steroid Biochem. Mol. Biol., 74:311 (2000)), Sp1 (Safe, Vitam. Horm., 62:231 (2001)) or NF-κB (McKay and Cidlowski, Endocr. Rev., 20:435 (1999)), or (c) indirect modulation of gene transcription via sequestration of general/common transcriptional components (Harnish et al., Endocrinology, 141:3403 (2000) and Speir et al., Circ. Res., 87:1006 (2000)). In addition, the ability of an estrogen receptor to regulate transcription through these various mechanisms appears to be cell-type specific, perhaps due to differences in the complement of transcriptional coregulatory factors available in each cell type (Cerillo et al., J. Steroid Biochem. Mol. Biol., 67:79 (1998); Evans et al., Circ. Res., 89:823 (2001); Maret et al., Endocrinology, 140:2876 (1999)). Also, transcriptional regulation is dependent upon the nature of the ligand, with various natural and synthetic selective estrogen receptor modulators acting as either estrogen receptor agonists or antagonists through each of these various mechanisms (Shang and Brown, Science, 295:2465 (2002); Katzenellenbogen and Katzenellenbogen, Science, 295:2380 (2002); Margeat et al., J. Mol. Biol., 326:77 (2003); Dang et al., J. Biol. Chem., 278:962 (2003)).

Another signaling pathway mediated by estrogens, also known as a 'non-classic', 'non-genomic' or 'membrane signaling' pathway, exists that involves cytoplasmic proteins, growth factors and other membrane-initiated signaling pathways (Segars et. al., Trends Endocrin. Met., 13:349 (2002)). Several intracellular signaling pathways have been shown to cross-talk with rapid estrogen-initiated effects: the adenylate cyclase pathway (Aronica et. al., PNAS, 91:8517 (1994)), the phospholipase C pathway (Le Mellay et. al., J. Cell. Biochem., 75:138 (1999)), the G-protein-coupled receptor-activated pathways (Razandi et. al., Mol. Endocrin., 13:307 (1999)) and the mitogen activated protein kinase (MAPK) pathway (Watters et. al., Endocrinology, 138:4030 (1997)). However, all membrane forms described to date are related to ER-α but not ER-β (Segars et. al., Trends Endocrin. Met., 13:349 (2002)).

Estrogen signaling has been associated pathologically with an increased risk for breast and endometrial cancer (Summer and Fuqua, Semin. Cancer Biol., 11:339 (2001); Turner et al., Endocr. Rev., 15:275 (1994); Farhat et al., FASEB J., 10:615 (1996); Beato et al., Cell, 83:851 (1995); Dobrzycka et al., Endo. Rel. Cancer, 10:517 (2003)). Consequently, estrogen receptors have been found to be essential in the initiation and development of most of these cancers. Current endocrine therapies for estrogen receptor-positive breast cancers are primarily designed to target estrogen levels, estrogen receptor levels, or the activity of estrogen and estrogen receptors. Use of a partial antiestrogen, tamoxifen, in the management of early-stage breast cancer has clearly demonstrated an increase in both disease-free and overall survival. In addition, recent studies demonstrate that tamoxifen can be used as a chemopreventive agent for hormone-dependent breast cancer. The major concerns of long-term therapy with tamoxifen are its uterotropic effects, which result in an increase risk for endometrial cancer, and the acquired clinical resistance to tamoxifen. This has led to the active pursuit of better selective estrogen receptor modulators (SERM) that display the optimal agonistic or antagonistic activities in various estrogen responsive target tissues.

Accordingly, what are needed are additional methods and materials that can be used to screen for agents that modulate estrogen signaling, as well as methods and materials that can be used to modulate estrogen signaling.

SUMMARY OF THE INVENTION

The present invention provides an isolated antibody that specifically binds to an amino acid sequence depicted at SEQ ID NO:1, or an immunogenic fragment thereof, preferably, an amino acid sequence depicted at amino acids 13-27 of SEQ ID NO:1. The antibody may be a monoclonal antibody or a polyclonal antibody. Optionally, the antibody is a humanized antibody. The antibody may be covalently attached to a compound such as, for instance, a chemotherapeutic agent or a detectable marker such as a fluorescent marker. The antibody may be present in a composition, and the composition may include a pharmaceutically acceptable carrier. Also provided are kits that include an antibody of the present invention.

The present invention also provides a method for making an antibody. The antibody may be polyclonal or monoclonal. The method includes administering to an animal a polypeptide having an amino acid sequence depicted at SEQ ID NO:1, or an immunogenic fragment thereof, preferably, an amino acid sequence depicted at amino acids 13-27 of SEQ ID NO:1. The method further includes isolating antibody from the animal, wherein the isolated antibody specifically binds to the amino acid sequence. The polypeptide or immunogenic subunit thereof may be covalently attached to a carrier polypeptide. The isolating may include obtaining from the animal a cell that produces the antibody, and making a monoclonal-antibody producing hybridoma using the cell. The invention further includes a polyclonal antibody produced by the method and a monoclonal antibody produced by the method.

The invention is also directed to a cell including an exogenous coding region, wherein the coding region encodes a polypeptide including SEQ ID NO:20. The coding region may encode a polypeptide having an amino acid sequence with at least 90% identity to SEQ ID NO:20, wherein the polypeptide has ER-α36 activity. The coding region may be operably linked to a constitutive promoter. The cell may be a eukaryotic cell or a prokaryotic cell. Also provided by the invention is a cell that expresses such polypeptides.

The present invention further provides a method for identifying an agent that binds a polypeptide. The method includes combining a polypeptide that includes an amino acid sequence depicted at SEQ ID NO:1, and an agent, and detecting the formation of a complex between the agent and the polypeptide, detecting an alteration in the activity of the polypeptide, or the combination thereof. The binding of the agent to the polypeptide may be detected by directly detecting the binding of the agent to the polypeptide, detecting the binding of the agent to the polypeptide using a competition binding assay, or the combination thereof. Optionally, the method also includes determining whether the agent binds a polypeptide including SEQ ID NO:18.

Also provided by the present invention are methods for detecting polypeptides. In one aspect, the method includes providing a cell, analyzing the cell for a polypeptide having ER-α36 activity and a molecular weight of 36 kDa as measured following electrophoresis on a sodium dodecyl sulfate (SDS)-polyacrylamide gel, and determining whether the cell expresses the polypeptide. The cell may be ex vivo or in vivo. The cell may be, for instance, a tumor cell, such as a breast tumor cell. The analyzing may include contacting the cell with an antibody that specifically binds to an amino acid sequence depicted at SEQ ID NO:1, or an immunogenic fragment thereof. The analyzing may include amplifying an mRNA polynucleotide to form amplified polynucleotides. The amplification includes contacting polynucleotides obtained from the cell with a primer pair that will amplify an mRNA polynucleotide that includes SEQ ID NO:22 or SEQ ID NO:25, or the combination thereof, wherein the presence of amplified polynucleotides indicates the cell expresses the polypeptide. One primer of the primer pair may be chosen from nucleotides of SEQ ID NO:22, nucleotides complementary to nucleotides of SEQ ID NO:25, or the combination thereof.

The invention also provides a method for inhibiting ER-α36 activity of a cell. The method includes contacting a cell expressing a polypeptide having an amino acid sequence depicted at SEQ ID NO:1 with a compound that inhibits ER-α36 activity. Such a compound may be an antibody that specifically binds to a polypeptide having an amino acid sequence depicted at amino acids 13-27 of SEQ ID NO:1. The cell may be in vivo or ex vivo, and optionally may be ER-α66 negative, ER-α46 negative, or the combination thereof. In some aspects the compound is not an anti-estrogen.

Further provided by the present invention is an isolated polypeptide that includes an amino acid sequence depicted at amino acids 13-27 of SEQ ID NO:1, preferably an amino acid sequence depicted SEQ ID NO:1, more preferably, an amino acid sequence depicted at SEQ ID NO:20. In another aspect, the isolated polynucleotide has at least 70% identity to SEQ ID NO:20, wherein the polypeptide has ER-α36 activity. The present invention also includes an immunogenic fragment of SEQ ID NO:1.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE DRAWINGS

FIG. 10 shows the predicted amino acid sequence of the ER-α36 open-reading frame. The amino acid positions are indicated by numbers on the left side of the amino acid sequence (SEQ ID NO:20). The last 27 amino acids that are unique to ER-α36 are underlined.

FIG. 12 shows (a) the DNA sequence of the 5' flanking sequence (SEQ ID NO:22) of the gene that encodes ER-α36 and which includes the ER-α36 promoter, and (b) the DNA sequence of the 3' flanking sequence (SEQ ID NO:25) of the gene that encodes ER-α36 and which includes the nucleotides encoded by exon 9. In the 5' flanking sequence the putative transcription binding sites are underlined and the proteins that bind to the nucleic acid sequence are also indicated. The initiation site of the cDNA is also indicated by an arrow.

DETAILED DESCRIPTION OF PREFERRED EMBODIMENTS OF THE INVENTION

Figure 2:
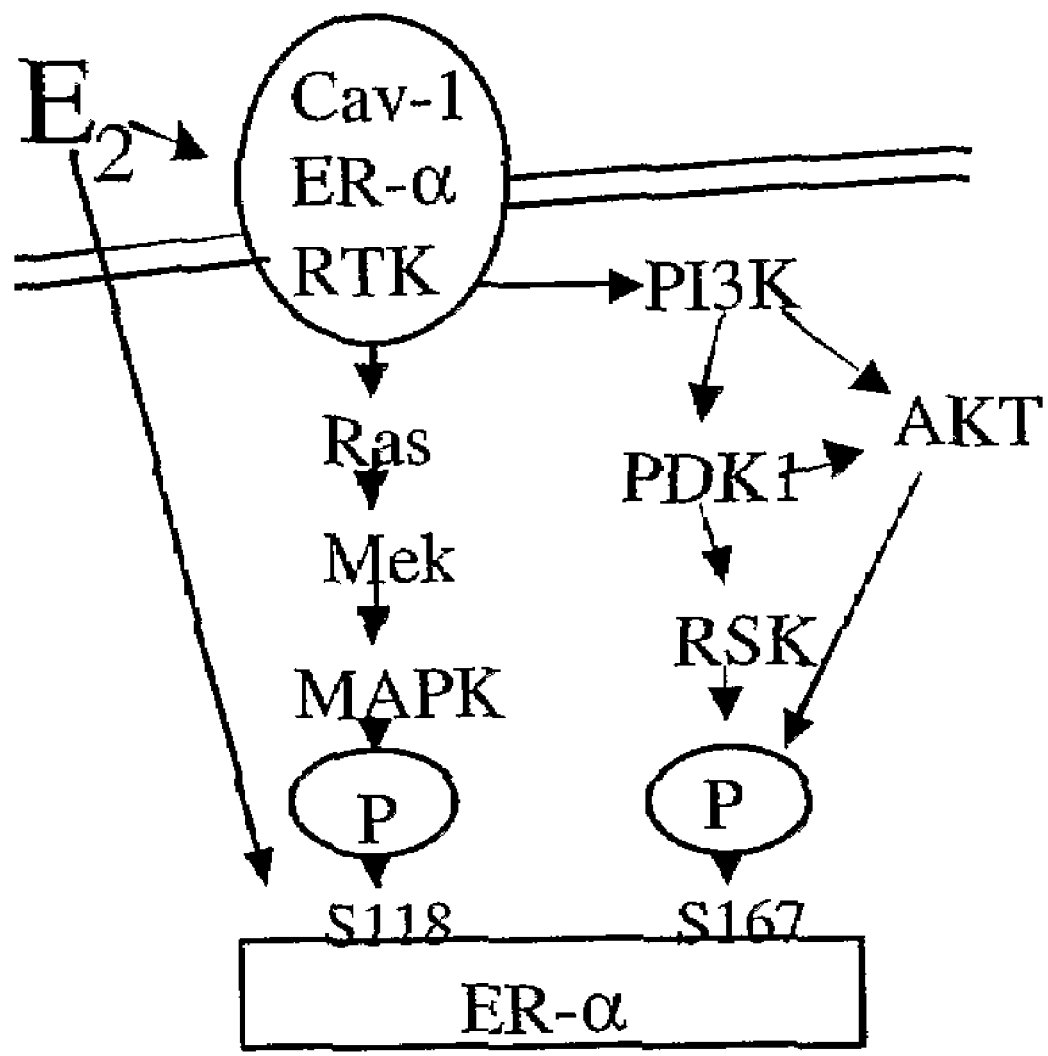
FIG. 2 is a schematic demonstrating the possible crosstalk between the membrane and genomic signaling pathways of ER-α. Cav-1 represents caveolin-1, ER-α, estrogen receptor-alpha; RTK, a receptor tyrosine kinase; Ras, Ras oncogene; Mek, MAP/ERK kinase; MAPK, a mitogen activated protein kinase; PI3K, phosphoinositol-triphosphate kinase; AKT, protein kinase 13; PDK1, phosphoinositol-dependent protein kinase; RSK, p90 ribosome S6 kinase.

It has been discovered that downregulation of the Caveolin-1 (Cav-1) system constitutively activates the mitogen activated protein kinase (MAPK) pathway, activates expression of estrogen receptor-alpha (ER-α), and triggers positive estrogen signaling. This discovery has, for the first time, provided a clear link between activated MAPK signaling and mammary tumorigenesis, especially breast cancer progression that is stimulated by estrogens. This discovery strongly suggests that Cav-1 plays an important role in maintaining normal growth of mammary epithelial cells by coordinating the cross-talk between the MAPK and estrogen signaling pathways, and its downregulation may contribute to dysregulation of these two important pathways which eventually lead to mammary tumorigenesis. A schematic of the estrogen signaling pathway and the MAPK signaling pathway is presented in FIG. 2.

An estrogen receptor-alpha isoform has also been identified and cloned. This 36-kDa isoform (ER-α36) of estrogen receptor-alpha is generated from a promoter located in the first intron of the original 66-kDa ER-α (ER-α66) gene. ER-α36 differs from ER-α66 because it lacks both transcriptional activation domains (AF-1 and AF-2) but retains the DNA-binding, dimerization and most of the ligand-binding domains. The structure of ER-α36 indicates that ER-α36 is a regulator of estrogen signaling. ER-α36 may also mediate the membrane effects of estrogen signaling as it is primarily expressed on the plasma membrane, and also in cytosol and nucleus.

ER-β has been proposed as a constitutive regulator of ER-α66 mediated estrogen signaling. The finding that ER-α46 lacking the AF-1 domain can dimerize to ER-α66 and inhibit the transactivation activity mediated by the AF-1 domain of ER-α66 indicates that ER-α46 plays a regulatory role in the functional activity mediated by the AF-1 domain of ER-α66. ER-α36 lacks both AF-1 and AF-2 domains. Thus, it is thought that ER-α36 inhibits biological functions mediated by both AF-1 and AF-2 of ER-α66, and AF-2 mediated functions of ER-α46 as well. With regulation mediated by ER-α36 and ER-α46, both of which might be expressed at different levels in different tissues, ER-α66 may function differently in different target tissues. Such a mechanism is thought to provide an explanation for the pleiotrophic roles of estrogen signaling in different biological processes.

Polypeptides and Peptidomimetics of the Invention

The invention provides polypeptides. As used herein, the term "polypeptide" refers broadly to a polymer of two or more amino acids joined together by peptide bonds. The terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring. Numerous examples of polypeptides that are within the scope of the invention are disclosed and described herein. In the case of a polypeptide or polynucleotide that is naturally occurring, it is preferred that such polypeptide or polynucleotide be isolated and, optionally, purified. An "isolated" polypeptide or polynucleotide is one that is separate and discrete from its natural environment. A "purified" polypeptide or polynucleotide is one that is at least 60% free, preferably 75% free, and most preferably 90% free from other components with which they are naturally associated. Polypeptides and nucleotides that are produced outside the organism in which they naturally occur, e.g., through chemical or recombinant means, are considered to be isolated and purified by definition, since they were never present in a natural environment. An "exogenous polypeptide" refers to a foreign polypeptide, i.e., a polypeptide that is not normally present in a cell, or a polypeptide that is normally present in a cell but has been introduced into the cell by experimental procedure, e.g., by introduction of a polynucleotide encoding the polypeptide.

The polypeptides of the present invention may be biologically active. Such biological activity is referred to herein as "ER-α36 activity." A example of a bioassay that can be used to determine if a polypeptide of the invention is biologically active involves contacting a cell that expresses this polypeptide with an estrogen or anti-estrogen and determining if activities of the MAPK pathway are increased or decreased in the presence of the estrogen or anti-estrogen, when compared to the MAPK activities in a control cell that was not expressing the polypeptide of the invention. Preferably, the MAPK activities are phosphorylation of ERK 1/2 and Mek 1/2, and preferably the phosphorylation of ERK 1/2 induced by a polypeptide of the present invention is not decreased in the presence of an anti-estrogen. Preferably, ER-α36 activity is membrane initiated. ER-α36 activity may be measured by exposing a cell expressing a polypeptide that may have ER-α36 activity to a different ligands. Examples of ligands that can be used include, but are not limited to, estrone (E1), 17α-estradiol (E2α), 17β-estradiol (E2β), estriol (E3), estetrol (E4), or an estrogen attached to a membrane impermeable molecule, for instance, bovine serum albumin (BSA). Generally, when the ER-α36 activity to be measured is to be limited to membrane initiated ER-α36 activity, an estrogen attached to a membrane impermeable molecule is used. The amount of estrogen used can vary, and is preferably in the range of between 1 nM and 10 nM. The cell exposed to the estrogen is preferably a quiescent cell. The exposure is allowed to occur for between 5 and 90 minutes, the cell is then lysed, and the polypeptides present in the cell are resolved by SDS-polyacrylamide gel electrophoresis. After transfer of the resolved polypeptides to a membrane, antibodies against the non-phosphorylated and phosphorylated forms of ERK 1/2 and Mek 1/2 are used to evaluate activation of the MAPK pathway. Optionally, an anti-estrogen, such as Tamoxifen, 4OH-Tamoxifen, or ICI-182,780, may be included to determine if the phosphorylation of ERK 1/2 is insensitive to anti-estrogens.

Figure 1:
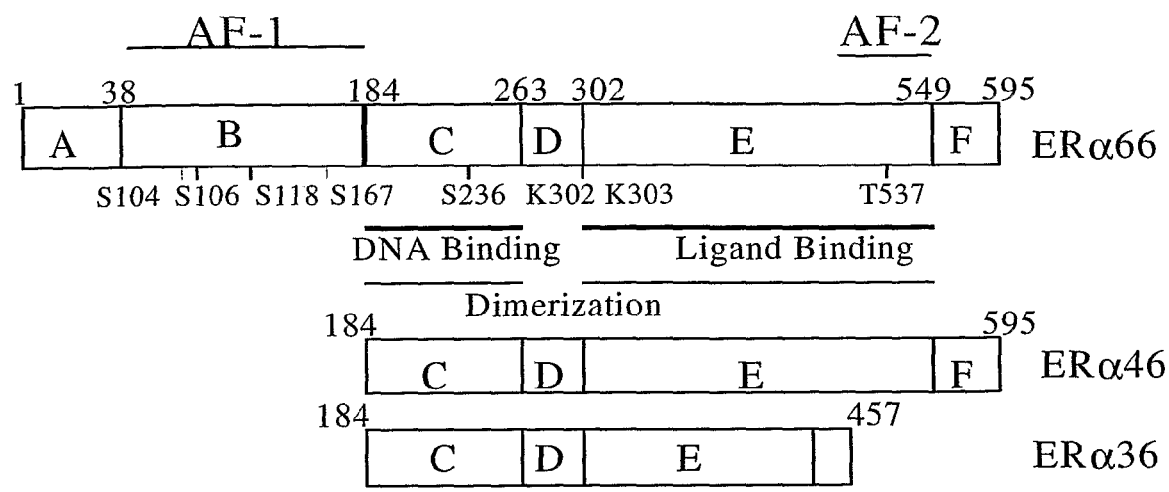
FIG. 1 illustrates the domain structure representation of Human estrogen receptor-alpha (ER-α) isoforms. Domains (labeled A-F), amino acid sequence numbering, AF-1 and AF-2, the DNA binding domain, the ligand-binding domain, and the dimerization domain are shown. The phosphorylation sites and function of each domain are also indicated.

The invention provides a polypeptide having the amino acid sequence depicted in SEQ ID NO:20. This polypeptide, and related polypeptides as described herein, are also referred to herein as ER-α36, ER-α36 isoform, and ER receptor α36-subunit. As shown in FIG. 1, the ER-α36 isoform lacks amino-terminal amino acid residues 1-183, carboxyl-terminal amino acid residues 430-595, and has an addition of 27 amino acid residues to its C-terminus when compared to the ER-α66 isoform (see Table 1). Estrogen receptor alpha isomers include ER-α36, ER-α46, ER-α66. Estrogen receptor beta isomers include ER-β. The present invention also provides estrogen receptors that include an ER-α36 isoform. Without intending to be limiting, the ER-α36 isoform is believed to modulate the response of a cell to estrogen through regulation of estrogen receptor function by forming a dimer with ER-α66, ER-α46 or ER-β. Further, ER-α36 is thought to lack activation factor 1 (AF-1) and activation factor 2 (AF-2) activity, and thus lacks intrinsic transcription activity. However, ER-α36 is thought to retain an intact dimerization domain that allows ER-α36 to dimerize with an ER-α46, ER-α66 or ER-β. This interaction is thought to allow ER-α36 to modulate the activity of ER-α46, ER-α66 and ER-β containing estrogen receptors.

TABLE 1

Amino acid and nucleotide sequences

| SEQ ID NO and Description | Amino acid and nucleotide Sequences |
|---|---|
| SEQ ID NO: 18, ER-α66, Accession Numbers M12674, AAA52399 | MTMTLHTKASGMALLHQIQGNELEPLNRPQLKIPLE RPLGEVYLDSSKPAVYNYPEGAAYEFNAAAAANAQV YGQTGLPYGPGPSEAAAFGSNGLGGFPPLNSVSPSPL MLLHPPPQLSPFLQPHGQQVPYYLENEPSGYTVREA GPPAFYRPNSDNRRQGGRERLASTNDKGSMAMESAK ETRYCAVCNDYASGYHYGVWSCEGCKAFFKRSIQGH NDYMCPATNQCTIDKNRRKSCQACRLRKCYEVGMMK GGIRKDRRGGRMLKHKRQRDDGEGRGEVGSAGDMRA ANLWPSPLMIKRSKKNSLALSLTADQMVSALLDAEP PILYSEYDPTRPFSEASMMGLLTNLADRELVHMINW AKRVPGFVDLTLHDQVHLLECAWLEILMIGLVWRSM EHPVKLLFAPNLLLDRNQGKCVEGMVEIFDMLLATS SRFRMMNLQGEEFVCLKSIILLNSGVYTFLSSTLKS LEEKDHIHRVLDKITDTLIHLMAKAGLTLQQQHQRL AQLLLILSHIRHMSNKGMEHLYSMKCKNVVPLYDLL LEMLDAHRLHAPTSRGGASVEETDQSHLATAGSTSS HSLQKYYITGEAEGFPATV |
| SEQ ID NO: 19, ER-α66, Accession Number M12674, AY425004 | ATGACCATGACCCTCCACACCAAAGCATCTGGGATG GCCCTACTGCATCAGATCCAAGGGAACGAGCTGGAG CCCCTGAACCGTCCGCAGCTCAAGATCCCCCTGGAG CGGCCCCTGGGCGAGGTGTACCTGGACAGCAGCAAG CCCGCCGTGTACAACTACCCCGAGGGCGCCGCCTAC GAGTTCAACGCCGCGGCCGCCGCCAACGCGCAGGTC TACGGTCAGACCGGCCTCCCCTACGGCCCCGGGTCT GAGGCTGCGGCGTTCGGCTCCAACGGCCTGGGGGGT TTCCCCCCACTCAACAGCGTGTCTCCGAGCCCGCTG ATGCTACTGCACCCGCCGCCGCAGCTGTCGCCTTTC CTGCAGCCCCACGGCCAGCAGGTGCCCTACTACCTG GAGAACGAGCCCAGCGGCTACACGGTGCGCGAGGCC GGCCCGCCGGCCATTCTACAGGCCAAATTCAGATAAT CGACGCCAGGGTGGCAGAGAAAGATTGGCCAGTACC AATGACAAGGGAAGTATGGCTATGGAATCTGCCAAG GAGACTCGCTACTGTGCAGTGTGCAATGACTATGCT TCAGGCTACCATTATGGAGTCTGGTCCTGTGAGGGC TGCAAGGCCTTCTTCAAGAGAAGTATTCAAGGACAT AACGACTATATGTGTCCAGCCACCAACCAGTGCACC ATTGATAAAAACAGGAGGAAGAGCTGCCAGGCCTGC CGGCTCCGCAAATGCTACGAAGTGGGAATGATGAAA GGTGGGATACGAAAAGACCGAAGAGGAGGGAGAATG TTGAAACACAAGCGCCAGAGAGATGATGGGGAGGGC AGGGGTGAAGTGGGGTCTGCTGGAGACATGAGAGCT GCCAACCTTTGGCCAAGCCCGCTCATGATCAAACGC TCTAAGAAGAACAGCCTGGCCTTGTCCCTGACGGCC GACCAGATGGTCAGTGCCTTGTTGGATGCTGAGCCC CCCATACTCTATTCCGAGTATGATCCTACCAGACCC TTCAGTGAAGCTTCGATGATGGGCTTACTGACCAAC CTGGCAGACAGGGAGCTGGTTCACATGATCAACTGG GCGAAGAGGGTGCCAGGCTTTGTGGATTTGACCCTC CATGATCAGGTCCACCTTCTAGAATGTGCCTGGCTA GAGATCCTGATGATTGGTCTCGTCTGGCGCTCCATG GAGCACCCAGTGAAGCTACTGTTTGCTCCTAACTTG CTCTTGGACAGGAACCAGGGAAAATGTGTAGAGGGC ATGGTGGAGATCTTCGACATGCTGCTGGCTACATCA TCTCGGTTCCGCATGATGAATCTGCAGGGAGAGGAG TTTGTGTGCCTCAAATCTATTATTTTGCTTAATTCT GGAGTGTACACATTTCTGTCCAGCACCCTGAAGTCT CTGGAAGAGAAGGACCATATCCACCGAGTCCTGGAC AAGATCACAGACACTTTGATCCACCTGATGGCCAAG GCAGGCCTGACCCTGCAGCAGCAGCACCAGCGGCTG GCCCAGCTCCTCCTCATCCTCTCCCACATCAGGCAC ATGAGTAACAAAGGCATGGAGCATCTGTACAGCATG AAGTGCAAGAACGTGGTGCCCCTCTATGACCTGCTG CTGGAGATGCTGGACGCCCACCGCCTACATGCGCCC ACTAGCCGTGGAGGGGCATCCGTGGAGGAGACGGAC CAAAGCCACTTGGCCACTGCGGGCTCTACTTCATCG CATTCCTTGCAAAAGTATTACATCACGGGGGAGGCA GAGGGTTTCCCTGCCACAGTCTGA |
| SEQ ID NO 21, ER-α36, Nucleotides 234-1166 of Accession Number BX640939 | ATGGCTATGGAATCTGCCAAGGAGACTCGCTACTGT GCAGTGTGCAATGACTATGCTTCAGGCTACCATTAT GGAGTCTGGTCCTGTGAGGGCTGCAAGGCCTTCTTC AAGAGAAGTATTCAAGGACATAACGACTATATGTGT CCAGCCACCAACCAGTGCACCATTGATAAAAACAGG AGGAAGAGCTGCCAGGCCTGCCGGCTCCGCAAATGC TACGAAGTGGGAATGATGAAAGGTGGGATACGAAAA GACCGAAGAGGAGGGAGAATGTTGAAACACAAGCGC CAGAGAGATGATGGGGAGGGCAGGGGTGAAGTGGGG TCTGCTGGAGACATGAGAGCTGCCAACCTTTGGCCA AGCCCGCTCATGATCAAACGCTCTAAGAAGAACAGC CTGGCCTTGTCCCTGACGGCCGACCAGATGGTCAGT GCCTTGTTGGATGCTGAGCCCCCATACTCTATTCC GAGTATGATCCTACCAGACCCTTCAGTGAAGCTTCG ATGATGGGCTTACTGACCAACCTGGCAGACAGGGAG CTGGTTCACATGATCAACTGGGCGAAGAGGGTGCCA GGCTTTGTGGATTTGACCCTCCATGATCAGGTCCAC CTTCTAGAATGTGCCTGGCTAGAGATCCTGATGATT GGTCTCGTCTGGCGCTCCATGGAGCACCCAGGGAAG CTACTGTTTGCTCCTAACTTGCTCTTGGACAGGAAC CAGGGAAAATGTGTAGAGGGCATGGTGGAGATCTTC GACATGCTGCTGGCTACATCATCTCGGTTCCGCATG ATGAATCTGCAGGGAGAGGAGTTTGTGTGCCTCAAA TCTATTCTTTTGCTTAATTCTGGTATCTCACATGTA GAAGCAAAGAAGAGAATCCTGAACTTGCATCCTAAA ATATTTGGAAACAAGTGGTTTCCTCGTGTCTAA |

Polypeptides of the present invention include polypeptides having an amino acid sequence that is at least 70% identical to SEQ ID NO:20. Such polypeptides include those having an amino acid sequence that is at least single unit percentages greater than 70% identical to SEQ ID NO:20, for example 71%, 72%, 73% identity, and so on to 100% identity to SEQ ID NO:20. Preferably, the polypeptide includes those having an amino acid sequence that is, in increasing order of preference, at least about 80% identity, at least about 90% identity, or at least about 95% identity to SEQ ID NO:20. Preferably the polypeptide is biologically active. Preferably the polypeptide has a molecular weight of 36 kDa as measured following electrophoresis on a sodium dodecyl sulfate (SDS)-polyacrylamide gel. Typically, residues involved in phosphorylation of ER-α66, e.g., S236, K302, and K303 are conserved, as are those residues involved in the function of the DNA binding domain, ligand binding domain, and dimerization domains of ER-α66. Residues that function in DNA binding, ligand binding, and/or dimerization are known in the art.

Percent identity between two polypeptide sequences is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al. (FEMS Microbiol. Lett., 174, 247-250 (1999)), and available on the world wide web at http://www.ncbi.nlm.nih.gov/blast/bl2seq/bl2.html. Preferably, the default values for all BLAST 2 search parameters are used, including matrix=BLOSUM62; open gap penalty=11, extension gap penalty=1, gap x_dropoff=50, expect=10, word-size=3, and optionally, filter on. In the comparison of two amino acid sequences using the BLAST search algorithm, structural similarity is referred to as "identity."

Polypeptides that are fragments of the ER-α36 estrogen receptor isoform are also provided by the invention. Preferably, a fragment is immunogenic. In some aspects, a fragment has ER-α36 activity. An example of an immunogenic fragment is the amino acid sequence depicted at amino acids 13-27 of SEQ ID NO:1, more preferably, 1-27 of SEQ ID NO:1. Such fragments are useful for preparing antibodies that specifically bind to the ER-α36 estrogen receptor isoform. Examples of fragments include an estrogen receptor isoform that has been truncated at either the N-terminus, or the C-terminus, or both, by one or more amino acids, as long as the fragment contains at least 5 contiguous amino acids, more preferably at least 7 contiguous amino acids, even more preferably at least contiguous 10 amino acids, and most preferably at least contiguous 12 amino acids.

The invention provides fusion polypeptides having a carrier polypeptide coupled to a polypeptide of the invention. A carrier polypeptide may be used to increase or decrease the solubility of a fusion polypeptide. The carrier polypeptide may also be used to increase the immunogenicity of the fusion polypeptide to increase production of antibodies that bind to a polypeptide of the invention. For example, a carrier polypeptide may be fused to a fragment of a polypeptide of the present invention to facilitate production of antibodies that specifically bind ER-α36. An example of such a fragment is a polypeptide having amino acids 13-27 SEQ ID NO:1. The invention is not limited by the types of carrier polypeptides used to create fusion polypeptides of the invention. Examples of carrier polypeptides include keyhole limpet hemacyanin, bovine serum albumin, ovalbumin, mouse serum albumin, rabbit serum albumin, and the like. The carrier polypeptides may also be used to provide for the separation or detection of a fusion polypeptide. Examples of such carrier proteins include glutathione-S-transferase, maltose-binding protein, chitin-binding protein, and polypeptides having the following amino acid sequences: QFFGLM (SEQ ID NO:2), EQKLISEEDL (SEQ ID NO:3), KAEDESS (SEQ ID NO:4), YPYDVPDYA (SEQ ID NO:5), DYKDDDDK (SEQ ID NO:6), YTDIEMNRLGK (SEQ ID NO:7), MASMTGGQQMG (SEQ ID NO:8), DTYRYI (SEQ ID NO:9), TDFYLK (SEQ ID NO:10), HHHHHH (SEQ ID NO:11), HPOL (SEQ ID NO:12), QYPALT (SEQ ID NO:13), QRQYGDVFKGD (SEQ ID NO:14), EYMPME (SEQ ID NO:15), EFMPME (SEQ ID NO:16), and RYIRS (SEQ ID NO:17). Accordingly, a fusion polypeptide can be detected or isolated by interaction with other components that bind to the carrier polypeptide portion of the fusion polypeptide. For example, a fusion polypeptide having avidin as a carrier polypeptide can be detected or separated with biotin through use of known methods. A carrier polypeptide may also be used to cause the fusion polypeptide to form an inclusion body upon expression within a cell. A carrier polypeptide can also be an export signal that causes export of a fusion polypeptide out of a cell, or directs a fusion polypeptide to a compartment within a cell, such as the periplasm.

The invention also provides two or more polypeptides of the invention that are continuously linked into a single amino acid chain. Such a polypeptide is referred to herein as a polypeptide. The polypeptides can be connected by linkers (see Stahl et al., U.S. Pat. No. 6,558,924). Such a polyprotein can be isolated and then cleaved to produce polypeptides or coupled polypeptides of the invention. The polyprotein can be cleaved through use of numerous methods, such as chemical or protease cleavage. Accordingly, linkers can be designed to be cleaved by specific proteases or chemicals. Examples of compounds that can be used to cleave polyproteins of the invention include chemicals and enzymes. Examples of chemicals include cyanogen bromide, formic acid and heat, hydroxylamine and heat, iodosobenzoic acid-2-(2-nitrophenyl)-3-methyl-3-bromoindole-nine in acetic acid, and the like. Examples of enzymes include Ala-64 subtilisin, clostripain, collagenase, enterokinase, factor Xa, renin, α-thrombin, trypsin, chymotrypsin, tobacco etch virus protease, and the like. Polyproteins may be used to increase the production efficiency of the polypeptides of the invention. Methods to produce polyproteins are known in the art (see Coolidge et al., U.S. Pat. No. 6,127,150).

The polypeptides of the invention include analogs that have been modified by the addition, substitution, or deletion of one or more contiguous or noncontiguous amino acids, or that have been chemically or enzymatically modified, e.g., by attachment of a reporter group, by an N-terminal, C-terminal or other functional group modification or derivatization, or by cyclization, as long as the analog retains biological activity or is able to stimulate the production of antibodies that bind to ER-α36. An analog can thus include additional amino acids at one or both of the termini of a polypeptide. Preferably, an analog is immunogenic, more preferably, an analog is immunogenic and has ER-α36 activity. In some aspects, the invention provides polypeptides that are not analogs.

Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Related amino acids (such as 3-hydroxyproline, 4-hydroxyproline, homocysteine, 2-aminoadipic acid, 2-aminopimelic acid, γ-carboxyglutamic acid, β-carboxyaspartic acid), amino acid amides (ornithine, homoarginine, N-methyl lysine, dimethyl lysine, trimethyl lysine, 2,3-diaminopropionic acid, 2,4-diaminobutyric acid, homoarginine, sarcosine and hydroxylysine) and substituted phenylalanines, norleucine, norvaline, 2-aminooctanoic acid, 2-aminoheptanoic acid, statine, O-valine, naphthylalanines, tetrahydroisoquinoline-3-carboxylic acid, and halogenated tyrosines may be exchanged for a like amino acid.

The invention provides peptidomimetics of the polypeptides of the invention. A peptidomimetic describes a polypeptide in which at least one of the peptide bonds has been replaced with a non-peptide bond, such as those commonly used in the pharmaceutical industry as non-peptide drugs, with properties analogous to those of the template polypeptide. (Fauchere, J., Adv. Drug Res., 15: 29 (1986), Evans et al., J. Med. Chem., 30:1229 (1987), and Janda et al., U.S. Pat. No. 6,664,372). Peptidomimetics are structurally similar to polypeptides having peptide bonds, but have one or more peptide linkages optionally replaced by a linkage such as, —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods known in the art. Advantages of peptidomimetics over natural polypeptide embodiments may include more economical production, greater chemical stability, altered specificity and enhanced pharmacological properties such as half-life, absorption, potency and efficacy.

Substitution of one or more amino acids within a polypeptide or a peptidomimetic with a D-amino acid of the same type (e.g., D-lysine in place of L-lysine) may be used to generate polypeptides and peptidomimetics that are, for instance, more stable and more resistant to endogenous proteases.

Polypeptides and peptidomimetics of the invention can be modified for in vivo use by the addition, at the amino-terminus and/or the carboxyl-terminus, of a blocking agent to decrease degradation in vivo. This can be useful in those situations in which the polypeptide termini tend to be degraded by proteases in vivo. Such blocking agents can include, without limitation, additional related or unrelated peptide sequences that can be attached to the amino and/or carboxyl terminal residues of the polypeptide or peptidomimetic of the invention. This can be done during chemical synthesis, or by recombinant DNA technology by methods familiar to artisans of average skill. Alternatively, blocking agents such as pyroglutamic acid, or other molecules known in the art, can be attached to the amino and/or carboxyl terminal residues, or the amino group at the amino terminus or carboxyl group at the carboxyl terminus can be replaced with a different moiety. Accordingly, the invention provides polypeptides and peptidomimetics that are blocked and the amino terminus, the carboxyl terminus, or the combination thereof.

Polypeptides of the invention can be produced on a small or large scale through use of numerous expression systems that include, but are not limited to, cells or microorganisms that are transformed with a recombinant vector into which a polynucleotide of the invention has been inserted. Such recombinant vectors and methods for their use are described below. These vectors can be used to transform a variety of organisms. Examples of such organisms include bacteria (for example, *E. coli* or *B. subtilis*); yeast (for example, *Saccharomyces* and *Pichia*); insects (for example, baculovirus); plants; or mammalian cells (for example, COS, CHO, BHK, 293, VERO, HeLa, MDCK, W138, and NIH 3T3 cells). Also useful as host cells are primary or secondary cells obtained directly from a mammal that are transfected with a vector.

Synthetic methods may also be used to produce polypeptides and peptidomimetics of the invention. Such methods are known in the art and are routine. For instance, the solid phase peptide synthetic method is an established and widely used method. Polypeptides can be readily purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; ligand affinity chromatography, and the like. Polypeptides can also be readily purified through binding of a fusion polypeptide to separation media, followed by cleavage of the fusion polypeptide to release a purified polypeptide. For example, a fusion polypeptide that includes a factor Xa cleavage site between the polypeptide and the carrier polypeptide can be created. The fusion polypeptide can be bound to an affinity column to which the carrier polypeptide portion of the fusion polypeptide binds. The fusion polypeptide can then be cleaved with factor Xa to release the polypeptide. Such a system has been used in conjunction with a factor Xa removal kit for purification of the polypeptides of the invention.

Polynucleotides

The invention provides polynucleotides that encode the polypeptides of the invention. The term "polynucleotide" refers broadly to a polymer of two or more nucleotides covalently linked in a 5' to 3' orientation. A polynucleotide may include nucleotide sequences having different functions, including for instance coding sequences, and non-coding sequences such as regulatory sequences. Coding sequence, non-coding sequence, and regulatory sequence are defined below. The terms nucleic acid, nucleic acid molecule, and oligonucleotide and protein included within the definition of polynucleotide and these terms are used interchangeably. It should be understood that these terms do not connote a specific length of a polymer of nucleotides, nor are they intended to imply or distinguish whether the polynucleotide is produced using recombinant techniques, chemical or enzymatic synthesis, or is naturally occurring.

Polynucleotides can be single-stranded or double-stranded, and the sequence of the second, complementary strand is dictated by the sequence of the first strand. The term "polynucleotide" is therefore to be broadly interpreted as encompassing a single stranded nucleic acid polymer, its complement, and the duplex formed thereby. "Complementarity" of polynucleotides refers to the ability of two single-stranded polynucleotides to base pair with each other, in which an adenine on one polynucleotide will base pair with a thymidine (or uracil, in the case of RNA) on the other, and a cytidine on one polynucleotide will base pair with a guanine on the other. Two polynucleotides are complementary to each other when a nucleotide sequence in one polynucleotide can base pair with a nucleotide sequence in a second polynucleotide. For instance, 5'-ATGC and 5'-GCAT are fully complementary, as are 5'-GCTA and 5'-TAGC.

An example of a polynucleotide of the present invention is SEQ ID NO:21 (see Table 1, also nucleotides 234-1166 of the nucleotide sequence present at GenBank accession number BX640939). Preferred polynucleotides of the invention also include polynucleotides having a nucleotide sequence that is "substantially complementary" to a nucleotide sequence that encodes a polypeptide according to the invention, or the complement of such nucleotide sequence. "Substantially complementary" polynucleotides can include at least one base pair mismatch, however the two polynucleotides will still have the capacity to hybridize. For instance, the middle nucleotide of each of the two DNA molecules 5'-AG-CAAATAT and 5'-ATATATGCT will not base pair, but these two polynucleotides are nonetheless substantially complementary as defined herein. Two polynucleotides are substantially complementary if they hybridize under hybridization conditions exemplified by 2×SSC (SSC: 150 mM NaCl, 15 mM trisodium citrate, pH 7.6) at 55° C. Substantially complementary polynucleotides for purposes of the present invention preferably share at least one region of at least 20 nucleotides in length which shared region has at least 60% nucleotide identity, preferably at least 80% nucleotide identity, more preferably at least 90% nucleotide identity, and most preferably at least 95% nucleotide identity. Particularly preferred substantially complementary polynucleotides share a plurality of such regions. Preferably the polynucleotides have a nucleotide sequence that is at least 70% identical to SEQ ID NO:21. More preferably the polynucleotides have a nucleotide sequence that is at least single unit percentages greater than 70% identical to SEQ ID NO:21, for example 71%, 72%, 73% identity, and so on to 100% identity to SEQ ID NO:21. Even more preferably, the polynucleotides have a nucleotide sequence that is at least 80% identical, at least 90% identical, or at least 95% identity to SEQ ID NO:21. Most preferably, the polynucleotides have a nucleotide sequence that is 100% identical to SEQ ID NO:21. A polynucleotide having at least 70% identity to SEQ ID NO:21 has ER-α36 activity.

Percent identity between two polynucleotide sequences is generally determined by aligning the bases of the two polynucleotide sequences to optimize the number of identical bases along the lengths of their sequences; gaps in either or both sequences are permitted in making the alignment in order to optimize the number of identical bases, although the bases in each sequence must nonetheless remain in their proper order. The two polynucleotide sequences are preferably compared using the Blastn program, version 2.0.11, of the BLAST 2 search algorithm, also as described by Tatusova et al. (FEMS Microbiol. Lett, 174, 247-250 (1999)), and available on the world wide web at http://www.ncbi.nlm.nih.gov/blast/bl2seq/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. Locations and levels of nucleotide sequence identity between two polynucleotide sequences can also be readily determined using CLUSTALW multiple sequence alignment software (J. Thompson et al., Nucl. Acids Res., 22:4673-4680 (1994)), available at from the world wide web at www.ebi.ac.uk/clustalw/.

It should be understood that a polynucleotide that encodes a polypeptide of the invention is not limited to a polynucleotide that contains all or a portion of naturally occurring genomic or cDNA nucleotide sequence, but also includes the class of polynucleotides that encode such polypeptides as a result of the degeneracy of the genetic code. For example, the naturally occurring polynucleotide sequence SEQ ID NO:21 is but one member of the class of nucleotide sequences that encodes a polypeptide having amino acid SEQ ID NO:20.

The class of nucleotide sequences that encode a selected polypeptide sequence is large but finite, and the nucleotide sequence of each member of the class can be readily determined by one skilled in the art by reference to the standard genetic code, wherein different nucleotide triplets (codons) are known to encode the same amino acid.

A polynucleotide that "encodes" a polypeptide of the invention optionally includes both coding and noncoding regions, and it should therefore be understood that, unless expressly stated to the contrary, a polynucleotide that "encodes" a polypeptide is not structurally limited to nucleotide sequences that encode a polypeptide but can include other nucleotide sequences outside (i.e., 5' or 3' to) the coding region. A "coding region" or "coding sequence" is a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. An "exogenous coding region" refers to a foreign coding region, i.e., a coding region that is not normally present in a cell, or a coding region that is normally present in a cell but has been introduced into the cell by experimental procedure, is operably linked to a regulatory region to which it is not normally operably linked, or the combination thereof.

A polynucleotide of the invention can be linear or circular in topology. A polynucleotide can be, for example, a portion of a vector. A vector can provide for further cloning (amplification of the polynucleotide), i.e., a cloning vector, or for expression of the polypeptide encoded by the coding region, i.e., an expression vector. A vector may include, but is not limited to, plasmid, phagemid, F-factor, virus, cosmid, or phage. The vector may be in a double-stranded or single-stranded linear or circular form. The vector can also transform a prokaryotic or eukaryotic host either by integration into the cellular genome or exist extrachromosomally (e.g., as an autonomous replicating plasmid with an origin of replication). The polynucleotide in the vector can be under the control of, and operably linked to, an appropriate promoter or other regulatory sequence for transcription in vitro or in a host cell, such as a eukaryotic cell, or a microbe, e.g. bacteria. Preferred examples of eukaryotic cells include MDA-MB-231, Hela, CHO, and MCF10A cell lines. A regulatory sequence, or regulatory region, refers to nucleotide sequences located upstream, within, or downstream of a coding sequence, and operably linked to, a coding sequence. Examples of regulatory sequences include enhancers, promoters, translation leader sequences, introns, and polyadenylation signal sequences. They include natural and synthetic sequences as well as sequences that may be a combination of synthetic and natural sequences. Regulatory sequences are not limited to promoters. However, some suitable regulatory sequences useful in the present invention will include, but are not limited to, constitutive promoters, tissue-specific promoters, development-specific promoters, inducible promoters and viral promoters. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

The vector may be a shuttle vector that functions in multiple hosts. The vector may also be a cloning vector which typically contains one or a small number of restriction endonuclease recognition sites at which foreign DNA sequences can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance or ampicillin resistance. Many cloning vectors are commercially available (for instance Stratagene, New England Biolabs, Clonetech). A vector may be an expression vector that contains regulatory sequences which direct the expression of a polynucleotide that is inserted into the expression vector. Numerous vectors are commercially available and are known in the art (Stratagene, La Jolla, Calif.; New England Biolabs, Beverly, Mass.). An expression vector may be used in in vitro transcription and translation assays.

Methods to introduce a polynucleotide into a vector are well known in the art (Sambrook et al., Molecular Cloning: A Laboratory Manual, 3rd edition, Cold Spring Harbor Press, Cold Spring Harbor, N.Y. (2001)). Briefly, a vector into which a polynucleotide is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a polynucleotide into the vector. The polynucleotide that is to be inserted into the vector is treated with one or more restriction enzymes to create a linearized segment having a blunt end, a "sticky" end with a 5' or a 3' overhang, or any combination of the above. The polynucleotide may also be treated with a restriction enzyme and subsequently treated with another DNA modifying enzyme. Such DNA modifying enzymes include, but are not limited to, polymerase, exonuclease, phosphatase or a kinase, to create a polynucleotide that has characteristics useful for ligation of a polynucleotide into the vector.

The treated vector and polynucleotide are then ligated together to form a construct containing a polynucleotide according to methods known in the art (Sambrook et al., Molecular Cloning: A Laboratory Manual, 3rd edition, Cold Spring Harbor Press, Cold Spring Harbor, N.Y. (2001)). Briefly, the treated nucleic acid fragment and the treated vector are combined in the presence of a suitable buffer and ligase. The mixture is then incubated under appropriate conditions to allow the ligase to ligate the nucleic acid fragment into the vector.

The invention further provides methods for making a polypeptide of the invention and methods for making the polynucleotides that encode them. The methods include biological, enzymatic, and chemical methods, as well as combinations thereof, and are well-known in the art. For example, a polynucleotide can be expressed in a host cell using standard recombinant DNA technologies, it can be enzymatically synthesized in vitro using a cell-free RNA based system, or it can be synthesized using chemical technologies such as solid phase peptide synthesis. When recombinant DNA technologies are used, the host cell can be, for example, a bacterial cell, an insect cell, a yeast cell, or a mammalian cell.

The present invention also provides polynucleotides having promoter activity. In one aspect, the promoter of the present invention includes a nucleotide sequence depicted at SEQ ID NO:22, or a portion thereof. In another aspect, a promoter of the present invention has a nucleotide sequence that is at least single unit percentages greater than 70% identical SEQ ID NO:22, for example 71%, 72%, 73% identity, and so on to 100% identity to SEQ ID NO:22. Methods for determining percent identity are described herein. Even more preferably, the promoter has a nucleotide sequence that is at least 80% identical, at least 90% identical, or at least 95% identity to SEQ ID NO:22. A promoter of the present invention has estrogen receptor (ER) regulated activity. As used herein, ER regulated activity refers to increased expression of an operably linked coding region in the presence of ER-α66, preferably, in the presence of ER-α66 bound to an estrogen. A promoter of the present invention is expressed in an estrogen dependent and independent manner. A promoter of the present invention may be operably linked to a coding region encoding a polypeptide, including a marker polypeptide. Examples of marker polypeptides include detectable markers (for instance, fluorescent proteins, enzymes, antigenic markers, and the like) and selectable markers (polypeptides causing drug resistance, drug susceptibility, or nutritional deficiency, or correcting a nutritional deficiency, and the like).

Antibodies

The invention provides antibodies that specifically bind to the polypeptides and peptidomimetics of the invention. As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets. In some aspects, an antibody of the present invention specifically binds to ER-α36 or a portion thereof, and does not specifically bind to ER-α66 or ER-α46.

Accordingly, the polypeptides and peptidomimetics of the invention and fragments thereof can be used as antigens to produce antibodies, including vertebrate antibodies, hybrid antibodies, chimeric antibodies, humanized antibodies, altered antibodies, univalent antibodies, monoclonal and polyclonal antibodies, Fab proteins, and single domain antibodies. For example, a polypeptide having SEQ ID NO:1 or a fragment thereof, such as amino acids 13-27 of SEQ ID NO:1, can be used to generate antibodies that specifically bind to ER-α36. A polypeptide or peptidomimetic of the present invention, or fragments thereof, can be modified by covalently linking them to an immunogenic carrier, such as keyhole limpet hemocyanin (KLH), bovine serum albumin, ovalbumin, mouse serum albumin, rabbit serum albumin, and the like.

If polyclonal antibodies are desired, a selected animal (e.g., mouse, rabbit, goat, horse or bird, such as chicken) may immunized with the desired antigen. Serum from the immunized animal is collected and treated according to known and routine methods. If serum containing polyclonal antibodies to a polypeptide of the invention contains antibodies to other antigens, the polyclonal antibodies can be purified by immunoaffinity chromatography. Techniques for producing and processing polyclonal antisera are known in the art (see, for example, Harlow et al., Antibodies: A Laboratory Manual, Cold Spring Harbor Pub. 1988)).

Monoclonal antibodies directed against the polypeptides or peptidomimetics of the present invention or fragments thereof can also be readily produced by one skilled in the art. The general methodology for making monoclonal antibodies by hybridomas is well known (see, for example, Harlow et al., Antibodies: A Laboratory Manual, Cold Spring Harbor Pub. 1988). Immortal antibody-producing cell lines (hybridimas) can be created by cell fusion, and also by other techniques such as direct transformation of B lymphocytes with oncogenic DNA, or transfection with Epstein-Barr virus. Panels of monoclonal antibodies produced against the polypeptides and peptidomimetics of the invention can be screened for various properties, for example epitope affinity. Other well known methods for making antibody include the use of phage display techniques (see, for instance, Kay et al., Phage display of peptides and proteins: A laboratory manual. San Diego: Academic Press (1996))

An antibody of the invention may be derived from a "humanized" monoclonal antibody. Humanized monoclonal antibodies may be produced by transferring mouse complementarity determining regions from heavy and light variable chains of a mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described (Orlandi et al., Proc. Nat'l Acad. Sci. USA, 86:3833 (1989), and techniques for producing humanized monoclonal antibodies are described (Jones et al., Nature, 321:522 (1986); Riechmann et al., Nature, 332:323 (1988)).

Antibody fragments of the invention can be prepared by routine known methods including proteolytic hydrolysis of the antibody or by expression in $E.$ $coli$ of a polynucleotide encoding the fragment. Antibody fragments can be obtained by digestion (with, for instance, pepsin or papain) of whole antibodies by conventional methods. For example, antibody fragments can be produced by enzymatic cleavage of antibodies with pepsin to provide a 5S fragment denoted $F(ab)_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antibodies can be screened to determine the identity of the epitope to which they bind. An epitope refers to the site on an antigen, such as a polypeptide of the invention, to which the paratope of an antibody binds. An epitope usually consists of chemically active surface groupings of molecules, such as amino acids or sugar side chains, and can have specific three-dimensional structural characteristics, as well as specific charge characteristics. Methods which can be used to identify an epitope are known in the art (Harlow et al., Antibodies: A Laboratory Manual, page 319 (Cold Spring Harbor Pub. 1988).

Antibodies may be screened for their ability to specifically bind to a polypeptide or peptidomimetic of the present invention. For example, antibodies that specifically bind to the ER-α36 isoform or a portion thereof, but not the ER-α46 or α66 isoform, can be selected through use of methods routine in the art (see Kitajima et al., U.S. Pat. No. 6,534,281, and Harlow et al., Antibodies: A Laboratory Manual, Cold Spring Harbor Pub. 1988).

The antibodies of the invention may be coupled to a large variety of compounds. Examples of compounds include detectable markers. Examples of such detectable markers include fluorescent markers, enzymes, radioisotopes, and the like, such as avidin or biotin, which permit the detection of an antibody. Methods to couple antibodies to detectable markers, and useful detectable markers, are known in the art. Such antibodies are useful within automated systems for detection of ER-α36. An antibody can be covalently attached to a chemotherapeutic agent. Chemotherapeutic agents useful in the treatment of cancers such as breast cancer and prostate cancer are known in the art. Examples of chemotherapeutic agents include centchroman, delmadinone acetate, droloxifene, idoxifene, tamoxifen, raloxifene, toremifene, fulvestrant and faslodex, a bisphosphonate, calcitonin, tribolone, parathyroid hormone, or strontium ranelate. Other examples include a cytokine, or a toxin, such as diphtheria toxin A chain.

Compositions

The present invention also provides compositions including a polynucleotide, peptidomimetic, or antibody of the present invention. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

The compositions of the invention may be prepared in many forms that include tablets, hard or soft gelatin capsules, aqueous solutions, suspensions, and liposomes and other slow-release formulations, such as shaped polymeric gels. An oral dosage form may be formulated such that the polypeptide, peptidomimetic, or antibody is released into the intestine after passing through the stomach. Such formulations are described in Hong et al., U.S. Pat. No. 6,306,434 and in the references contained therein.

Oral liquid compositions may be in the form of, for example, aqueous or oily suspensions, solutions, emulsions, syrups or elixirs, or may be presented as a dry product for constitution with water or other suitable vehicle before use. Such liquid compositions may contain conventional additives such as suspending agents, emulsifying agents, non-aqueous vehicles (which may include edible oils), or preservatives.

A composition can be formulated for parenteral administration (e.g., by injection, for example, bolus injection or continuous infusion) and may be presented in unit dosage form in ampules, prefilled syringes, small volume infusion containers or multi-dose containers with an added preservative. The compositions may take such forms as suspensions, solutions, or emulsions in oily or aqueous vehicles, and may contain formulatory agents such as suspending, stabilizing and/or dispersing agents.

Compositions suitable for rectal administration can be prepared as unit dose suppositories. Suitable carriers that may be included in the composition include those exemplified by saline solutions and other materials commonly used in the art.

For administration by inhalation, a composition can be conveniently delivered from an insufflator, nebulizer or a pressurized pack or other convenient means of delivering an aerosol spray. Pressurized packs may include a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, a composition may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, a composition may be administered via a liquid spray, such as via a plastic bottle atomizer.

A composition can be formulated for transdermal administration. A composition can also be formulated as an aqueous solution, suspension or dispersion, an aqueous gel, a water-in-oil emulsion, or an oil-in-water emulsion. A transdermal formulation may also be prepared by encapsulation of a composition within a polymer. The dosage form may be applied directly to the skin as a lotion, cream, salve, or through use of a patch.

Compositions of the invention may also contain other ingredients such as flavorings, colorings, anti-microbial agents, and preservatives. In addition, a composition of the invention can include pharmaceutically active ingredients, such as hormones, anti-necrotic agents, vasodilators, pharmaceutical agents and the like.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. In one aspect, the range of dosage for use in humans is an amount sufficient to result in serum concentrations that are at least 10 micromolar (μM), preferably, at least 25 μM, more preferably, 50 μM.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a composition can include a single treatment or, preferably, can include a series of treatments.

Methods of Detection

The present invention provides methods for detecting a polypeptide of the present invention. The method typically includes providing a cell, analyzing the cell for a polypeptide of the present invention, and determining whether the cell expresses the polypeptide. The cell may be ex vivo or in vivo. As used herein, the term "ex vivo" refers to a cell that has been removed, for instance, isolated from the body of a subject. Ex vivo cells include, for instance, primary cells (e.g., cells that have recently been removed from a subject and are capable of limited growth or maintenance in tissue culture medium), and cultured cells (e.g., cells that are capable of extended growth or maintenance in tissue culture medium). As used herein, the term "in vivo" refers to a cell that is within the body of a subject. An in vivo cell may be a cell present in an organ or a tumor. The cell is preferably a mammalian cell, such as, for instance, mouse, rat, or primate (e.g., monkey, human), preferably, human. Preferred examples of cells include breast cells, such as a breast tumor cell, and prostate cells, such as a prostate tumor cell. A cell may be obtained from a subject by, for example, biopsy of human breast or prostate tissue. Samples obtained from nearly any type of tissue may be used. Control cells may be cultured in vitro according to methods known in the art. Cells that do not express an ER-α36 kDa estrogen receptor and thus can be used as a negative control include HEK293 cells. Positive control cells include cells grown at low cell density in the presence of serum, and BRCA1 negative cells. Preferably, cells are grown at low density in the presence of serum. Control cells may also be obtained from tissue samples through, for example, biopsy.

In one aspect, the method includes analyzing the cell by contacting the cell with an antibody of the present invention. Whether a cell expresses a polypeptide of the present invention can be determined using detection methods that are routine and known in the art. Examples of immunoassays include competitive and non-competitive assays such as radioimmunoassay, immunoenzymometric assay, immunofluorometric assay, or enzymoimmunoassays assays. Chemiluminescent methods with horseradish peroxidase, alkaline phosphatase, or other chemiluminescent detection agents can also be used. Western blotting and chromatographic assays can also be used within the method of the invention. An antibody of the present invention used to detect a polypeptide of the present invention may be coupled to a detectable marker and thereby detected directly, or a second antibody may be used. When detection methods are used that permit detection of the polypeptide in different areas of the cell, a cell expressing an ER-α36 is typically considered ER-α36 positive when the polypeptide is associated predominantly with the plasma membrane and the cytoplasm, and less than 20% of the signal is associated with the nucleus.

In another aspect, the method includes analyzing the cell by amplifying a polynucleotide, preferably, an RNA polynucleotide (e.g., an mRNA), to form amplified polynucleotides. Preferably, a polynucleotide is amplified by polymerase chain reaction (PCR), preferably, by reverse transcriptase (RT) PCR. Methods for synthesizing a DNA polynucleotide from an RNA polynucleotide are known in the art and routine. Polynucleotides obtained from the cell are contacted with a primer pair that will amplify a polynucleotide that includes SEQ ID NO:22 or SEQ ID NO:25, or the combination thereof. The presence of amplified polynucleotides resulting from such a primer pair indicates the cell expresses the estrogen receptor. As used herein, the term "primer pair" refers two oligonucleotides designed to flank a region of a polynucleotide to be amplified. One primer is complementary to nucleotides present on the sense strand at one end of a polynucleotide to be amplified and another primer is complementary to nucleotides present on the anti-sense strand at the other end of the polynucleotide to be amplified. The polynucleotide to be amplified can be referred to as the template polynucleotide. The nucleotides of a polynucleotide to which a primer is complementary can be referred to as a target sequence. A primer can have at least about 15 nucleotides, preferably, at least about 20 nucleotides, most preferably, at least about 25 nucleotides. The conditions for amplifying a polynucleotide by PCR vary depending on the nucleotide sequence of primers used, and methods for determining such conditions are routine in the art.

After amplification, the presence of the amplified polynucleotides may be determined, for instance, by gel electrophoresis. The amplified polynucleotides can be visualized by staining (e.g., with ethidium bromide) or labeling with a suitable label known to those skilled in the art, including radioactive and nonradioactive labels. Typical radioactive labels include $^{33}$P. Nonradioactive labels include, for example, ligands such as biotin or digoxigenin as well as enzymes such as phosphatase or peroxidases, or the various chemiluminescers such as luciferin, or fluorescent compounds like fluorescein and its derivatives.

Optionally, the presence in a cell of an ER-α66 polypeptide, ER-α46 polypeptide, ER-β, or the combination thereof, may also be determined. Methods for detecting the presence of ER-α66, ER-α46, ER-β, or the combination thereof, include the use of immunological detection using antibody or polynucleotide based detection methods such as amplification of a polynucleotide. When detection methods are used that permit detection of the polypeptide in different areas of the cell, a cell expressing an ER-α66 or ER-α46 is typically considered ER-α66 or ER-α46 positive when the polypeptide is associated predominantly with the nucleus of the cell, e.g., greater than 90% of the signal is associated with the nucleus.

Approximately 70-80% of all breast cancers expresses ER-α66 and are referred to as ER-positive breast cancer. These tumors usually grow more slowly, are better differentiated, and are associated with a better overall prognosis (Clark, In: Harris J R, editor. Diseases of the breast, volume 2. Lippincott Williams & Wilkins, 38:103-116 (2000)). The methods for detecting the presence of a polypeptide of the present invention are useful as a diagnostic marker to differentiate estrogen-positive and estrogen-negative cancer, preferably, breast cancer. The results disclosed in the Examples herein strongly indicate that estrogen signaling mediated by ER-α36 contributes to mammary tumorigenesis and suggest that ER-α36 may be involved in tumorigenesis of ER-α66 negative breast cancers. The results disclosed in the Examples herein also indicate that a cell highly expressing a polypeptide of the present invention is more resistant to lower dose of an anti-estrogen, for instance, tamoxifen, than a cell that expresses high levels of ER-α66 but lower levels of ER-α36. Thus, methods for detecting the presence of a polypeptide of the present invention permit the identification of a new class of patients, i.e., ER-α66-negative and ER-α36-positive. Methods for detecting the presence of a polypeptide of the present invention are also useful in determining the sensitivity of a cell to an anti-estrogen, and providing information relevant to, for instance, determining an appropriate course of treatment for an individual. For instance, a physician may decide that a subject with ER-α36-positive breast tumor cells may require higher doses of tamoxifen to overcome resistance to lower levels.

Detection of the presence of ER-α66, ER-α46, ER-α36, ER-β, or the combination thereof, also permits comparing the ratio of the estrogen receptors. Determination of the ratio of two or more of the estrogen receptors allows the sensitivity of a cell to an anti-estrogen, for instance, tamoxifen, to be predicted. For instance, in this aspect of the invention the ratio of ER-α36 to ER-α46, the ratio of ER-α36 to ER-α66, the ratio of ER-α36 to ER-β, or a combination thereof, in a cell is determined and compared to the corresponding ratio in a control cell. Such a ratio is referred to herein as an ER-α36 ratio. In one example, the control cell can be a cell that is refractory to treatment with an anti-estrogen. In another example, the control cell is a cell that is not refractory to the anti-estrogen. If an above described ER-α36 ratio determined in the test cell is the same as the ER-α36 ratio described in the control cell, then the test cell is classified according to the status of the control cell. For example, if the ER-α36 to ER-α66 ratio of the test cell is the same as the ER-α36 to ER-α66 ratio in a control cell known to be refractory to tamoxifen treatment, then the test cell is classified as being refractory to tamoxifen treatment. However, if the ER-α36 to ER-α66 ratio in the test cell is the same as the ER-α36 to ER-α66 ratio in a control cell that is not refractory to tamoxifen treatment, then the test cell is classified as not being refractory to tamoxifen treatment. In another example, the ER-α36 ratio determined in a test cell is compared to the corresponding ratio in a control cell known to be refractory to tamoxifen treatment, and to the ratio in a control cell that is known not to be refractory to tamoxifen treatment. The test cell is then classified as being refractory to tamoxifen treatment, or not refractory to tamoxifen treatment, as described above. An example of a control cell that is known not to be refractory to tamoxifen treatment is MCF7 (ATTC Collection accession number HTB-22). An example of a control cell that is known to be refractory to low dose tamoxifen treatment is MDA-MB-231. Breast cancer cells that are known to be refractory to tamoxifen treatment can also be used as control cells by comparing an ER-α36 ratio in a test cell.

Identification of Agents that Bind a Polypeptide of the Present Invention

The present invention also provides methods for identifying an agent that binds a polypeptide of the present invention. Such methods are also referred to as screening assays. The method includes combining a polypeptide of the present invention with an agent, and determining whether the agent binds the polypeptide. Typically, determining whether an agent binds the polypeptide includes detecting the formation of a complex between the agent and the polypeptide. Methods for determining the complex include, for instance, directly detecting the binding of an agent to the polypeptide, and detecting the binding of the agent to the polypeptide using a competition binding assay. The assay may be a cell-free assay. The assay may be done in the presence or absence of an estrogen or anti-estrogen. Optionally, the method also includes determining whether the agent binds an ER-α66 polypeptide, such as a polypeptide with an amino acid sequence depicted at SEQ ID NO:18. Preferably, an agent does not bind an ER-α66 polypeptide.

An agent can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach includes peptide libraries, while the other four approaches are applicable to peptide, nonpeptide oligomer, or small molecule libraries of compounds (Lam, Anticancer Drug Des. 12:145 (1997)). Examples of methods for the synthesis of molecular libraries can be found in the art (see, for example DeWitt et al. Proc. Natl. Acad. Sci. USA 90:6909 (1993); Erb et al. Proc. Natl. Acad. Sci. USA 91:11422 (1994); Zuckermann et al. J. Med. Chem. 37:2678 (1994); Cho et al. Science 261:1303 (1993); Carrell et al. Angew. Chem. Int. Ed. Engl. 33:2059 (1994); Carrell et al. Angew. Chem. Int. Ed. Engl. 33:2061 (1994); and Gallop et al. J. Med. Chem. 37:1233 (1994)). The sources for potential agents to be screened include also include, for instance, fermentation media of bacteria and fungi, and cell extracts of plants and other vegetations.

Libraries of compounds maybe presented, for instance, in solution (e.g. Houghten Bio/Techniques 13:412-421 (1992)), or on beads (Lam Nature 354:82-84 (1991)), chips (Fodor Nature 364:555-556 (1993)), bacteria (U.S. Pat. No. 5,223, 409), spores (U.S. Pat. Nos. 5,571,698; 5,403,484; and 5,223, 409), plasmids (Cull et al. Proc. Natl. Acad. Sci. USA 89:1865-1869 (1992)), or phage (Scott et al. Science 249: 386-390 (1990); Devlin Science 249:404-406 (1990); Cwirla et al. Proc. Natl. Acad. Sci. USA 87:6378-6382 (1990); and Felici J. Mol. Biol. 222:301-310 (1991)).

Determining the ability of an agent to bind to a polypeptide of the present invention can be accomplished, for example, by coupling the agent with a radioisotope or enzymatic label such that binding of the agent to the polypeptide of the present invention can be determined by detecting the labeled compound in a complex. For example, agents can be labeled with $^{125}I$, $^{35}S$, $^{14}C$, or $^{3}H$, either directly or indirectly, and the radioisotope detected by direct counting of radioemission or by scintillation counting. Alternatively, agents can be enzymatically labeled with, for example, horseradish peroxidase, alkaline phosphatase, or luciferase, and the enzymatic label detected by determination of conversion of an appropriate substrate to product.

In a similar manner, one may determine the ability of an agent to alter (e.g., stimulate or inhibit) the binding of a polypeptide of the present invention to a known ligand of the polypeptide, e.g., molecule with which a polypeptide of the present invention binds or interacts in nature. An example of such a ligand is estrogen, as well as an anti-estrogen, such as tamoxifen. In a preferred aspect, the ability of an agent to alter the binding of a polypeptide of the present invention to bind to a ligand can be determined by monitoring the activity of the polypeptide of the invention.

In yet another aspect, an assay of the present invention includes contacting a polypeptide of the present invention with an agent and determining the ability of the agent to bind to the polypeptide. Binding of the agent to the polypeptide can be determined either directly or indirectly as described above. In a preferred aspect, the assay includes contacting a polypeptide of the present invention with a ligand known to bind a polypeptide of the present invention to form an assay mixture, contacting the assay mixture with an agent, and determining the ability of the agent to preferentially bind to the polypeptide as compared to the ligand.

In another aspect, an assay includes contacting a polypeptide of the present invention with an agent and determining the ability of the agent to alter (e.g., stimulate or inhibit) the activity of the polypeptide of the present invention.

In a further aspect, an assay includes screening for agents that alter (e.g., stimulate or inhibit) the ability of a polypeptide of the present invention to regulate transcriptional transactivation of an estrogen response element, including, for instance, activities mediated by the AF-1 and/or AF-2 domains of ER-α66. Preferably, a fusion polypeptide including a polypeptide of the present invention and a polypeptide having a transcriptional activation domain, or a transcriptional repressor domain, is used. An example of a polypeptide having a transcriptional activation domain is VP-16, and other useful polypeptides having a transcriptional activation domain or a transcriptional repressor domain are known in the art. Typically, such a fusion polypeptide is used in conjunction with a polynucleotide having an estrogen response element upstream of a promoter and an operably linked coding sequence. A variety of promoters can be used, including, for instance, a thymidine kinase promoter. Preferably, the operably linked coding region encodes a detectable marker, such as luciferase, or a fluorescent polypeptide such as green fluorescent protein. In one aspect, the fusion polypeptide with transcriptional activation domain, polynucleotide, and agent are combined under conditions that promote expression of the coding region present on the polynucleotide in the absence of the agent, and the effect of the agent in altering transcription is determined. Optionally, an ER-α66 polypeptide and/or an ERβ polypeptide may also be present, and the assay used to identify agents that alter (e.g., stimulate or inhibit) the ability of a polypeptide of the present invention to modulate ligand-dependent and ligand-independent transcriptional activities of ER-α66 polypeptide or ERβ. Preferably, both the fusion polynucleotide and the polynucleotide that includes an estrogen response element upstream of a promoter and an operably linked coding sequence are present in a cell. Without intending to be limiting, it is expected that agents that alter the ability of a polypeptide of the present invention to regulate transcriptional transactivation may include agents that alter the conformation of a polypeptide of the present invention to increase or decrease the ability of the In the assays, it may be desirable to immobilize either a polypeptide of the present invention, its ligand, or the agent to facilitate separation of complexed from uncomplexed forms of one or both of the molecules, as well as to accommodate automation of the assay. In one embodiment, a fusion protein can be provided that adds a domain that allows the polypeptide of the present invention to be bound to a matrix. For example, fusion polypeptides with glutathione-S-transferase can be adsorbed onto glutathione sepharose beads (Sigma Chemical, St. Louis, Mo.) or glutathione-derivatized microtitre plates, which are then combined with the agent, and the mixture incubated under conditions conducive to complex formation (e.g. at physiological conditions for salt and pH). Following incubation, the beads or microtitre plate wells can be washed to remove any unbound components and complex formation is measured either directly or indirectly, for example, as described above. Alternatively, the complexes can be dissociated from the matrix, and the level of binding determined.

Other techniques for immobilizing polypeptides on matrices can also be used in the screening assays of the invention. For example, a polypeptide of the present invention can be immobilized using conjugation of biotin and streptavidin. A polypeptide of the present invention can be biotinylated using biotin-NHS (N-hydroxy-succinimide) with techniques well known in the art (e.g., biotinylation kit, Pierce Chemicals, Rockford, Ill.), and, for instance, immobilized in the wells of streptavidin-coated 96-well plates (Pierce Chemicals). Alternatively, antibodies reactive with a polypeptide of the present invention can be derivatized to the wells of the plate, and unbound polypeptide of the present invention trapped in the wells by antibody conjugation. Methods for detecting such complexes, in addition to those described above for the GST-immobilized complexes, include immunodetection of complexes using antibodies reactive with antibody that specifically binds a polypeptide of the present invention.

The present invention also includes novel agents identified by the above-described screening assays and uses thereof for treatments as described herein.

Methods of Treatment

The present invention is further directed to methods for treating certain diseases in a subject. The subject is a mammal, preferably a human. As used herein, the term "disease" refers to any deviation from or interruption of the normal structure or function of a part, organ, or system, or combination thereof, of a subject that is manifested by a characteristic symptom or set of symptoms. Diseases include cancers dependent upon signalling via steroid hormone receptors, such as estrogen receptors. Examples of such diseases are referred to as estrogen-related cancers and include breast cancer and prostate cancer. Typically, whether a subject has a disease, and whether a subject is responding to treatment, is determined by evaluation of symptoms associated with the disease. As used herein, the term "symptom" refers to objective evidence of a disease present in a subject. Symptoms associated with diseases referred to herein and the evaluation of such symptoms are routine and known in the art. Examples of symptoms of cancers dependent upon signalling via steroid hormone receptors include, for instance, the presence and size of tumors, and the presence and amount of biomarkers. Biomarkers are compounds, typically polypeptides, present in a subject and indicative of the progression of cancer. Examples of biomarkers include, for instance, Her-2 expression, and cyclin D1 expression.

Treatment of a disease can be prophylactic or, alternatively, can be initiated after the development of a disease. Treatment that is prophylactic, for instance, initiated before a subject manifests symptoms of a disease, is referred to herein as treatment of a subject that is "at risk" of developing a disease. An example of a subject that is at risk of developing a disease is a person having a risk factor, such as a genetic marker, that is associated with the disease. Examples of genetic markers indicating a subject has a predisposition to develop certain cancers such as breast, or prostate cancer include alterations in the BRAC1 and/or BRAC2 genes. Treatment can be performed before, during, or after the occurrence of the diseases described herein. Treatment initiated after the development of a disease may result in decreasing the severity of the symptoms of one of the conditions, or completely removing the symptoms.

In some aspects, the methods typically include contacting a cell with a composition including an effective amount of an agent that inhibits the activity of a polypeptide of the present invention, for instance, an agent identified using a method described herein. Preferably, such an agent binds to a polypeptide of the present invention. In some aspects, the agent is preferably not an anti-estrogen. As used herein, an "effective amount" is an amount effective to inhibit in a cell the activity of a polypeptide of the present invention, decrease symptoms associated with a disease, or the combination thereof. In one aspect, a composition may include an effective amount of an antibody of the present invention. Preferably, an antibody is covalently attached to a chemotherapeutic agent, such as, for instance, tamoxifen. The composition may optionally include other chemotherapeutic agents. Whether an agent or antibody, preferably, antibody, is expected to function in this aspect of the invention can be evaluated using ex vivo models and animal models. Such models are known in the art and are generally accepted as representative of disease or methods of treating humans. A preferred example of such an animal model is the nude mouse. For instance, breast cancer cells can be inoculated into the mammary fatpad of ovariectomized female nude mice, and lesion formation followed and evaluated, for example, by palpation, measurement by vernier calipers, and tumor weight. Transgenic animal models are also available. For instance, models for the study of prostate cancer such as the TRAMP model (see, for instance, Greenberg et al., Proc. Natl. Acad. Sci. USA, 92:2429-3443 (1995)) and for breast cancer such as the MMTV-Wnt-1 model (see, for instance, Tsukamoto et al., Cell, 55:619-625 (1988)) are commonly accepted as models for human disease.

In another aspect, a cell is contacted with a composition including a polynucleotide, where the polynucleotide causes the post-transcriptional silencing of a coding region encoding a polypeptide of the present invention. Such a polynucleotide is referred to herein as a silencing polynucleotide. The silencing polynucleotide may be introduced into a cell as an RNA polynucleotide, or as a vector including a DNA polynucleotide that encodes and will express the RNA polynucleotide. More than one type of polynucleotide can be administered. For instance, two or more polynucleotides that are designed to silence the same mRNA can be combined and used in the methods herein. Alternatively, two or more polynucleotides can be used together where the polynucleotides are each designed to silence different mRNAs.

As used herein, the term "polynucleotide" refers to a polymeric form of nucleotides of any length, either ribonucleotides, deoxynucleotides, or a combination thereof, and includes both single-stranded molecules and double-stranded duplexes. A polynucleotide can be obtained directly from a natural source, or can be prepared with the aid of recombinant, enzymatic, or chemical techniques. Preferably, a polynucleotide of the present invention is isolated. As used herein, a "target coding region" and "target coding sequence" refer to the coding region whose expression is inhibited by a silencing polynucleotide. As used herein, a "target mRNA" is an mRNA encoded by a target coding region. An example of a target coding region is the nucleotide sequence encoding an ER-α36 (SEQ ID NO: 21), the 5' flanking nucleotide sequence (SEQ ID NO:20), or the 3' flanking nucleotide sequence, including the nucleotide sequence encoded by exon 9 (SEQ ID NO:25).

Silencing polynucleotides include double stranded RNA (dsRNA) polynucleotides. The sequence of a silencing polynucleotide includes one strand, referred to herein as the sense strand, of between 16 to 30 nucleotides, for instance, 16, 17, 18, 19, 20, 21, 22, 23, 24, 25, 26, 27, 28, 29, or 30 nucleotides. The sense strand is substantially identical, preferably, identical, to a target mRNA. As used herein, the term "identical" means the nucleotide sequence of the sense strand has the same nucleotide sequence as a portion of the target mRNA. As used herein, the term "substantially identical" means the sequence of the sense strand differs from the sequence of a target mRNA at 1, 2, or 3 nucleotides, preferably 1 nucleotide, and the remaining nucleotides are identical to the sequence of the mRNA. These 1, 2, or 3 nucleotides of the sense strand are referred to as non-complementary nucleotides. When a silencing polynucleotide includes a sense strand that is substantially identical to a target mRNA, the 1, 2, or 3 non-complementary nucleotides are preferably located in the middle of the sense strand. For instance, if the sense strand is 21 nucleotides in length, the non-complementary nucleotides are typically at nucleotides 9, 10, 11, or 12, preferably nucleotides 10 or 11. The other strand of a dsRNA polynucleotide, referred to herein as the anti-sense strand, is complementary to the sense strand. The term "complementary" refers to the ability of two single stranded polynucleotides to base pair with each other, where an adenine on one polynucleotide will base pair to a thymine or uracil on a second polynucleotide and a cytosine on one polynucleotide will base pair to a guanine on a second polynucleotide. The silencing polynucleotides also include the double stranded DNA polynucleotides that correspond to the dsRNA polynucleotides. Also included are the single stranded RNA polynucleotides and single stranded DNA polynucleotides corresponding to the sense strands and anti-sense strands disclosed herein. It should be understood that the sequences disclosed herein as DNA sequences can be converted from a DNA sequence to an RNA sequence by replacing each thymidine nucleotide with a uracil nucleotide. Without intending to be limiting, the polynucleotides of the present invention cause the post-transcriptional silencing of a target coding region. Modifications to polynucleotides for use in silencing are known in the art and the silencing polynucleotides can be so modified.

The sense and anti-sense strands of a dsRNA silencing polynucleotide of the present invention may also be covalently attached, typically by a spacer made up of nucleotides. Such a polynucleotide is often referred to in the art as a short hairpin RNA (shRNA). Upon base pairing of the sense and anti-sense strands, the spacer region forms a loop. The number of nucleotides making up the loop can vary, and loops between 3 and 23 nucleotides have been reported (Sui et al., Proc. Nat'l. Acad. Sci. USA, 99, 5515-5520 (2002), and Jacque et al., Nature, 418, 435-438 (2002)).

A silencing polynucleotide causes the post-transcriptional inhibition of expression, also referred to as silencing, of a target coding region. Without intending to be limited by theory, after introduction into a cell a silencing polynucleotide will hybridize with a target mRNA and signal cellular endonucleases to cleave the target mRNA. The result is the inhibition of expression of the polypeptide encoded by the mRNA. Whether the expression of a target coding region is inhibited can be determined by, for instance, measuring a decrease in the amount of the target mRNA in the cell, measuring a decrease in the amount of polypeptide encoded by the mRNA, or by measuring a decrease in the activity of the polypeptide encoded by the mRNA. A silencing polynucleotide can be present in a vector. A silencing polynucleotide can be present in a vector as two separate complementary polynucleotides, each of which can be expressed to yield a sense and an antisense strand of the dsRNA, or as a single polynucleotide containing a sense strand, a loop region, and an anti-sense strand, which can be expressed to yield an RNA polynucleotide having a sense and an antisense strand of the dsRNA.

A silencing polynucleotide can be designed using methods that are routine and known in the art. For instance, a silencing polynucleotide may be identified by scanning the coding region AA dinucleotide sequences; each AA and the downstream (3') consecutive 16 to 30 nucleotides of the mRNA can be used as the sense strand of a candidate polynucleotide. A candidate polynucleotide is the polynucleotide that is being tested to determine if it decreases expression of one of a polypeptide of the present invention. The candidate polynucleotide can be identical to nucleotides located in the region encoding the polypeptide, or located in the 5' or 3' untranslated regions of the mRNA. Optionally and preferably, a candidate polynucleotide is modified to include 1, 2, or 3, preferably 1, non-complementary nucleotides. Other methods are known in the art and used routinely for designing and selecting candidate polynucleotides. A silencing polynucleotide may, but need not, begin with the dinucleotide AA at the 5' end of the sense strand. A candidate polynucleotide may also include overhangs of 1, 2, or 3 nucleotides, typically on the 3' end of the sense strand, the anti-sense strand, or both. Candidate polynucleotides are typically screened using publicly available algorithms (e.g., BLAST) to compare the candidate polynucleotide sequences with coding sequences. Those that are likely to form a duplex with an mRNA expressed by a non-target coding region are typically eliminated from further consideration. The remaining candidate polynucleotides may then be tested to determine if they inhibit expression of one of the polypeptides described herein.

In general, candidate polynucleotides are individually tested by introducing a candidate polynucleotide into a cell that expresses polypeptide of the present invention. The candidate polynucleotides may be prepared in vitro and then introduced into a cell. Methods for in vitro synthesis include, for instance, chemical synthesis with a conventional DNA/RNA synthesizer. Commercial suppliers of synthetic polynucleotides and reagents for such synthesis are well known. Methods for in vitro synthesis also include, for instance, in vitro transcription using a circular or linear vector in a cell free system.

The candidate polynucleotides may also be prepared by introducing into a cell a construct that encodes the candidate polynucleotide. Such constructs are known in the art and include, for example, a vector encoding and expressing a sense strand and an anti-sense strand of a candidate polynucleotide, and RNA expression cassettes that include the sequence encoding the sense strand and an anti-sense strand of a candidate polynucleotide flanked by operably linked regulatory sequences, such as an RNA polymerase III promoter and an RNA polymerase III terminator, that result in the production of an RNA polynucleotide. The cell can be ex vivo or in vivo. Candidate polynucleotides may also be tested in animal models.

When evaluating whether a candidate polynucleotide functions to inhibit expression of one of the polypeptides described herein, the amount of target mRNA in a cell containing a candidate polynucleotide can be measured and compared to the same type of cell that does not contain the candidate polynucleotide. Methods for measuring mRNA levels in a cell are known in the art and routine. Such methods include quantitative RT-PCR. Primers and specific conditions for amplification of an mRNA vary depending upon the mRNA, and can be readily determined by the skilled person. Other methods include, for instance, Northern blotting, and array analysis.

Other methods for evaluating whether a candidate polynucleotide functions to inhibit expression of one of the polypeptides described herein include monitoring the polypeptide. For instance, assays can be used to measure a decrease in the amount of polypeptide encoded by the mRNA, or to measure a decrease in the activity of the polypeptide encoded by the mRNA. Methods for measuring a decrease in the amount of a polypeptide include assaying for the polypeptide present in cells containing a candidate polynucleotide and comparing to the same type of cell that does not contain the candidate polynucleotide. For instance, an antibody of the present invention may be used in, for example, Western immunoblot, immunoprecipitation, or immunohistochemistry. Antibodies to each of the polypeptides described herein are commercially available. Methods for measuring a decrease in the activity of one of a polypeptide of the present invention may also be used.

Kits

The invention provides kits that contain reagents that can be used in the methods of the present invention, including, for instance, determining if a cell expresses a polypeptide of the present invention. Such kits can contain packaging material and an antibody of the present invention. Such kits may also be used by medical personal for the formulation of compositions, such as pharmaceutical compositions, that contain an antibody of the invention.

The packaging material provides a protected environment for the antibody. For example, the packaging material may keep the antibody from being contaminated. In addition, the packaging material may keep an antibody in solution from becoming dry. Examples of suitable materials that can be used for packaging materials include glass, plastic, metal, and the like. Such materials may be silanized to avoid adhesion of an antibody to the packaging material.

In one example, the invention provides a kit that includes packaging material, a first antibody that specifically binds to a polypeptide of the invention, and a second antibody that specifically binds to an ER-α66 polypeptide. The kit may optionally include additional components such as buffers, reaction vessels, secondary antibodies, and syringes.

EXAMPLES

Example 1

Caveolin-1 Haploinsufficiency Produces Activation of ER-α Expression and Estrogen Stimulated Transformation of Normal Breast Epithelial Cells A gene-trapped library of cell clones from normal human mammary epithelial MCF10A cells was prepared through use of a poly-A trap retrovirus vector (RET) obtained from Dr. Philip Leder's laboratory at Harvard Medical School (Ishida et. al., Nucl. Acid Res., 27:580 (1999)). Briefly, this vector used an improved poly-A trap strategy for the efficient identification of functional genes regardless of their expression status in target cells. A combination of a strong splice acceptor and an effective polyadenylation signal assures the complete disruption of the function of "trapped" genes. Inclusion of a promoterless GFP cDNA in the RET vector allows the expression pattern of the trapped gene to be easily monitored in living cells. A retrovirus containing the RET vector was used to infect MCF10A cells. The cells were then screened for G418-resistant to establish a gene-trapped library of MCF10A cells. After selection by G418 for three weeks, GFP expression, under the control of the endogenous promoter of the "trapped" gene, was monitored and G418 resistant and GFP expressing clones were then selected. This library represented $3 \times 10^5$ independent infected clones in which one allele of a functional gene was disrupted by the RET vector.

Figure 3:
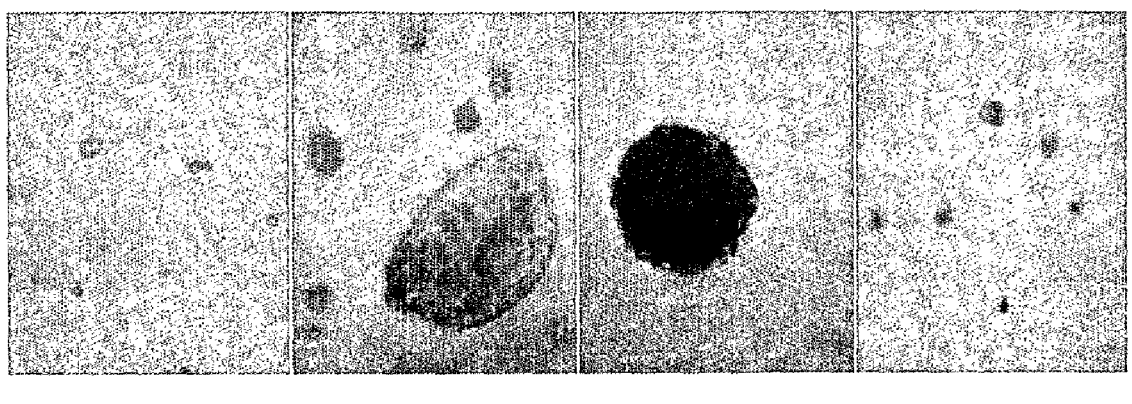
FIG. 3 is a picture showing that pRET-infected MCF10A cells grow a big colony in soft-agar in the presence of estradiol (E2). The ST1 clone shows an accelerated growth in E2-containing soft-agar. MCF7 and MCF10A cells are included as a positive and negative control, receptively.

It was thought that loss of expression of genes with tumor suppression activity could confer the transformed phenotype to normal MCF10A cells. A soft-agar cloning assay was performed and cells from the gene-trapped cell library that acquired anchorage-independent growth, a characteristic of the transformed phenotype, were identified. More than 100 positive colonies ($\geq 30$ cells) from the library of G418-resistant cells grew in soft-agar while the parental MCF10A cells did not. Twenty cell clones were isolated, expanded, and then selected again in soft-agar containing regular serum plus 10-8 M 17b-estradiol (E2) and dextrin coated charcoal-stripped serum that lacks steroid hormones for three weeks. Four cell clones (ST1, ST3, ST4 and ST6) that exhibited accelerated growth in soft-agar containing extra E2 were isolated and expanded (FIG. 3).

3'-RACE, which permits the capture of unknown 3'mRNA sequences that lie between the exon of a candidate gene and the poly-A tail, was used to clone potential genes whose disruption leads to MCF10A cell transformation. Transformation of the MCF10A cells was thought to be due to positive estrogen signaling. The purified PCR fragments resulting from the RACE procedure were cloned and sequenced. Using a BLASTN search, the DNA sequences from two clones (ST1 and ST3) were matched identically to the sequence of caveolin-1 (Cav-1) exon-3 located on chromosome 7 (GenBank accession number XM048940). This result indicated that an allele of the Cav-1 gene was disrupted in at least 2 clones. In addition to Cav-1, two other genes were identified using the same technique. The gene disrupted in clone ST4 was SPRR1B (GenBank accession number NT-004441.5), a member of the cornifin/small proline-rich protein family involved in structural organization of cornified cell envelopes. Another gene from clone ST6 is a putative novel gene (GenBank accession number 6599139) with no known function.

Figure 4:
FIG. 4 is a Western blot showing downregulation of Caveolin-1 (Cav-1) expression in pRET-infected MCF10A cells. Equal amounts of total cellular extracts from various cell lines were analyzed by Western blot using a rabbit anti-Cav-1 antibody (N20). The position of Cav-1 is indicated by an arrow and the cell extract analyzed in each lane is indicted above each lane.

Cav-1 protein levels were analyzed in parental MCF10A cells to test whether expression levels of Cav-1 were decreased in the cav-1 gene trapped cells. Four cell clones (ST1, 3, 4 and 6) described above, and MCF10A-Ha-ras, (MCF10A cells transformed by a Ha-ras mutant) were analyzed. Compared to the levels in parental MCF10A cells, Cav-1 protein levels were about 2-fold lower in all transformed cells as demonstrated by Western blot analysis (FIG. 4). This data is consistent with Cav-1 expression being decreased when only one functional allele of the cav-1 gene is functional in ST1 and ST3 cells. This indicates that Cav-1 haploinsufficiency created by "gene trapping" leads to transformation stimulated by E2. This data also indicates that downregulation of Cav-1 is also involved in transformation resulted from the disruption of other genes in ST4 and ST6 cells.

Figure 5:
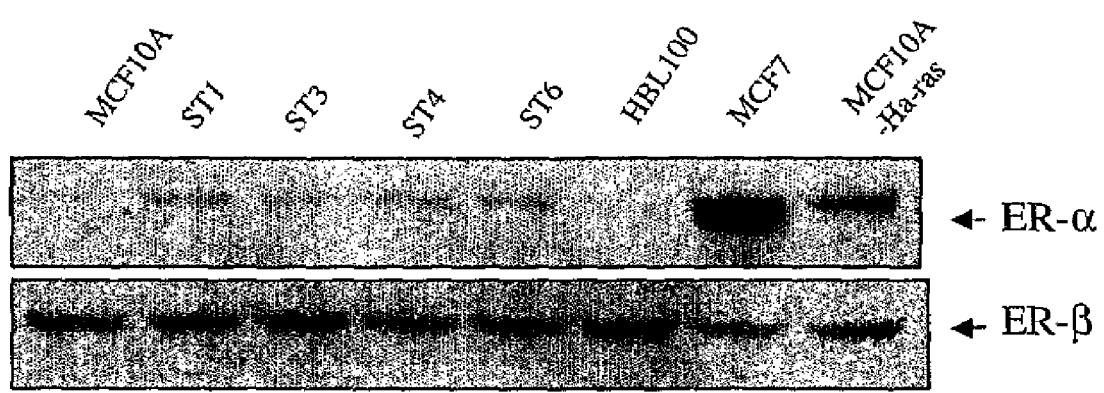
FIG. 5 is a western blot showing upregulation of ER-α expression in pRET-infected MCF10A cells. Equal amounts of total cellular extracts from various cell lines were analyzed by Western blot using antibodies against ER-α (H222) and ER-β. The positions of ER-α and ER-β are indicated by arrows and the cell extract analyzed in each lane is indicted above each lane.

To determine the mechanism by which Cav-1 haploinsufficiency leads to estrogen-stimulated cell growth and transformation, the expression levels of ER-α and ER-β in the transformed cells described above was examined. It was found that all of the four transformed cell clones expressed ER-α at a level comparable to that in the Ha-ras transformed cells, whereas parental MCF10A cells and HBL-100 cells, another normal mammary epithelial cell line, expressed undetectable levels of ER-α (FIG. 5). ER-β expression was without any change in all of the cells tested (FIG. 5). This data indicated that ER-α expression was activated and that estrogen signaling in these transformed cells is responsible for the estrogen-stimulated cell growth on soft-agar. It has been shown before that both ER-α expression and estrogen signaling are activated in Ha-ras transformed cells (Shekhar et. al., Int. J. Oncol., 13:907 (1998) and Shekhar et. al., Am. J. of Pathl., 152:1129 (1998)). The present results indicate that the Ras/MAPK pathway is involved in the regulation of ER-α expression and positive estrogen signaling.

Figure 6:
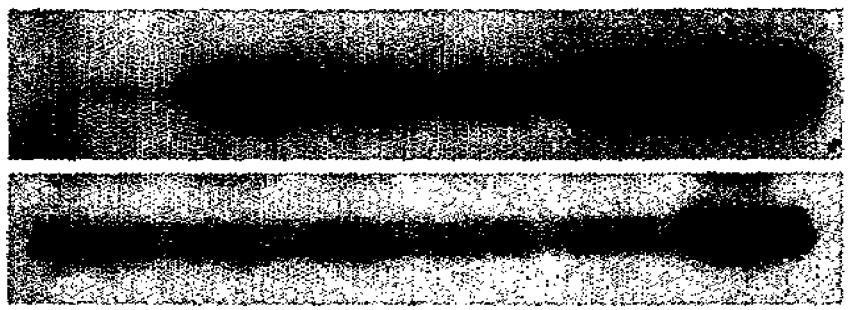
FIG. 6 is a Western blot showing activation of ERK1/2 phosphorylation in pRET-infected MCF10A cells. Equal amounts of total cellular extracts from the cell lines were analyzed by Western blot using antibodies against ERK1/2 and phosphorylated ERK1/2.

Activation of the MAPK pathway in these transformed cells was analyzed by examining the phosphorylation levels of ERK1/2 using phospho-specific antibodies. It was found that ERK1/2 are highly and constitutively phosphorylated in all transformed cells but not in MCF10A cells (FIG. 6).

Taken together, these data indicate that the Cav-1/Ras/MAPK pathway is involved in the activation of ER-α expression during human breast cancer development and cooperates with estrogen signaling pathway to stimulate transformed cell proliferation.

Example 2

Identification, Cloning, Expression and Characterization of an Isoform of Estrogen Receptor Alpha (ER-α36)

Figure 7:
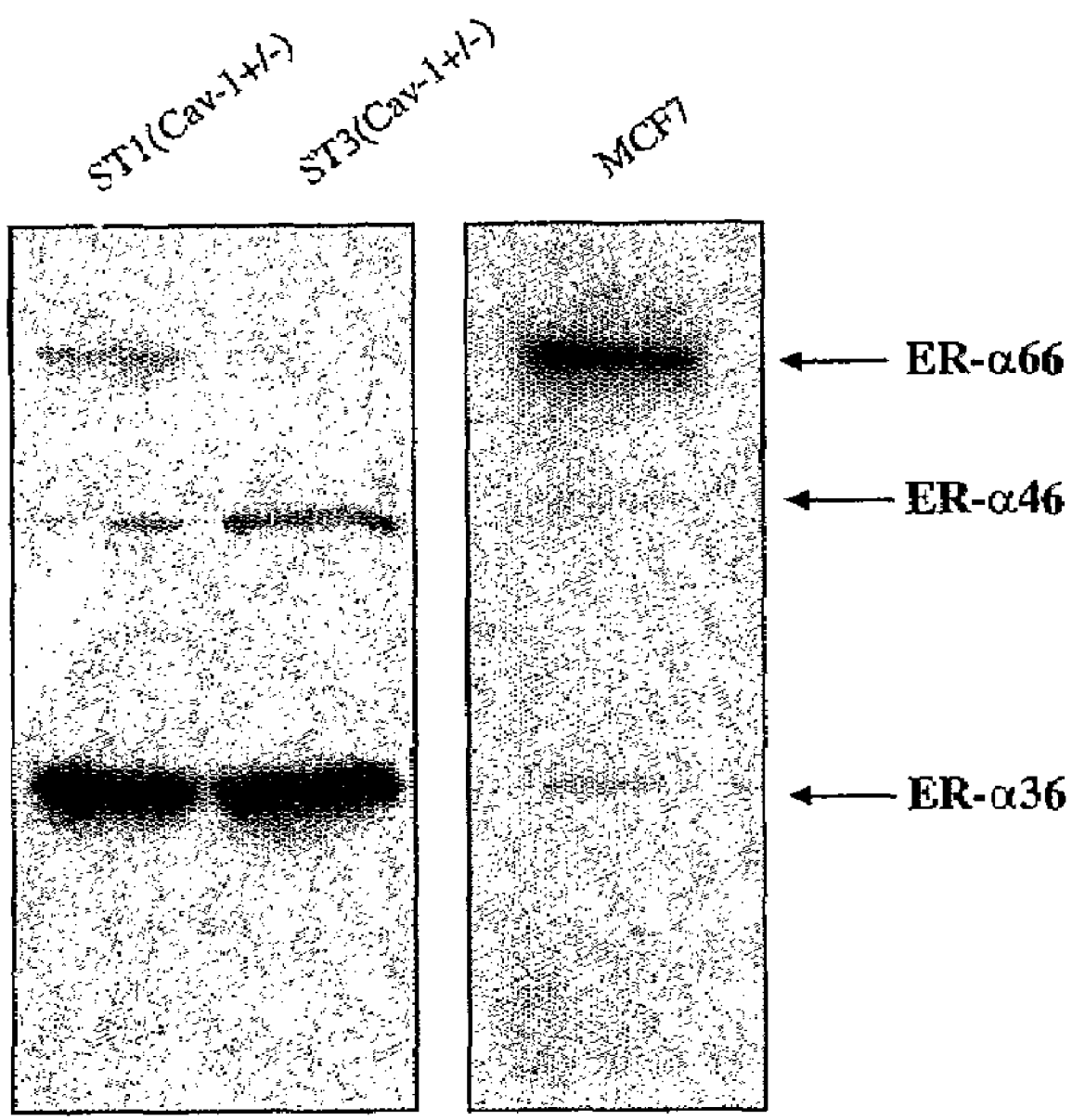
FIG. 7 is a Western blot showing the existence of three ER-α proteins in Cav-1 haploinsufficient cells, ST1 and ST3, and MCF7 breast cancer cells. Equal amounts of total cellular extracts from the cell lines were analyzed by Western blot using the H222 antibody against ER-α. The positions of ER-α66, ER-α46 and ER-α36 are indicated by arrows and the cell extract analyzed in each lane is indicted above each lane.

During the course of the work described above, three protein bands (66-kDa, 46-kDa and 36-kDa) were consistently observed in western blot analysis using the Rat anti-ER-α antibody (clone H222) from Research Diagnostic, INC. The H222 antibody recognizes the ligand-binding domain of ER-α. To exclude the possibility that 46-kDa and 36-kDa protein bands were the degradation products of ER-α66, as suggested by a previous report (Abbondanza et. al., Steroids, 58:4 (1993)), cells were lysed in culture plates using a buffer containing 8 M urea and tested by western blot analysis. Three distinct bands were readily observed in Cav-1 haplo-insufficient cells, ST1 and ST3, and MCF7 breast cancer cells (FIG. 7). These results indicated the existence of ER-α isoforms that share a similar epitope that is recognized by the antibody H222.

Through a literature search, it was found that a 46-kDa isoform of ER-α had been cloned that functions as a dominant-negative inhibitor of transactivation mediated by the AF-1 domain of ER-α66 (Flouriot et. al., EMBO J., 19:4688 (2000)). A continued search identified a clone from a normal human edometrium cDNA library (RZPD clone number: DKFZp686N23123) that contains a 5.4 kb cDNA. This cDNA clone harbors a 310 amino acid open reading frame that theoretically can produce a protein with a predicted molecular weight of 35.7 kDa. The cDNA sequence of the open-reading frame matched 100% to DNA sequence of the exons 2 to 6 of the ER-α66 gene. The 5'untranslated region (5'UTR) of the cDNA showed 100% homology to the DNA sequence of the first intron of the ER-α66 gene from 734 to 907 (the first base pair of the 34,233 bp first intron of ER-α66 gene was designated as 1). Thus, it was determined that the transcript of ER-α36 is initiated from a previously unidentified promoter in the first intron of the ER-α66 gene.

Figure 8:
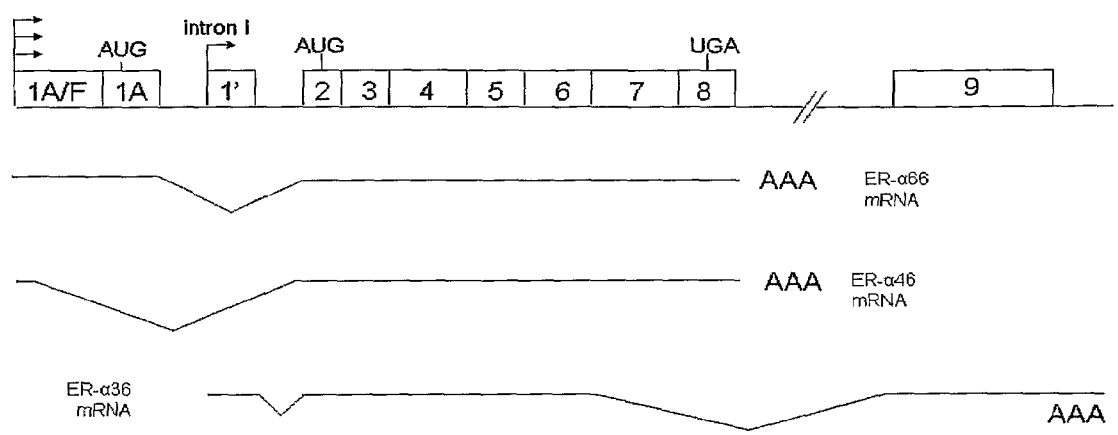
FIG. 8 illustrates the genomic organization of the human ER-α gene. The location of multiple promoters are shown as arrows. The translation start and stop sites are indicated as AUG and UGA. The exons are shown as numbered boxes. Intron 1 is also shown with the exon 1' in a box. The lower panel shows the mRNA structure of ER-α isoforms. Poly A sites are indicated by AAA.

A small, non-coding novel exon from 734 to 907 of the first intron of the ER-α66 gene was designated as "exon 1'". The exon 1' is then spliced directly into the exon 2 of the ER-α66 gene and continues from exon 2 to exon 6 of the ER-α66 gene. Exon 6 is then spliced to an exon located 64,141 bp downstream of the ER-α66 gene (GeneBank accession number AY425004, see Table 1). The cDNA sequence encoding the last 27 amino acids and the 4,293 bp 3'untranslated region was matched 100% to a continuous sequence from the genomic sequence of clone RP1-1304 on chromosome 6q24.2-25.3 (GeneBank accession number AL078582), indicating the remaining cDNA sequence of this novel ER-α isoform is transcribed from one exon of 4,374 bp located downstream of the previously reported ER-α66 gene. This exon is thus designated as exon 9 to reflect the extra exon beyond the previous reported eight exons (FIG. 8). All of these splicing events are supported by the identification of perfect splice donors and acceptors at the splice juncture. The protein ER-α36 can be produced from a perfect Kozak sequence located in the second exon, the same initiation codon used to produce ER-α46 (Flouriot et. al., EMBO J., 19:4688 (2000)). ER-α36 differs from ER-α66 by lacking both transcriptional activation domains, AF-1 and AF-2, but retaining the dimerization, DNA-binding and partial ligand-binding domains. It also possesses an extra, unique 27 amino acid domain to replace the last 138 amino acids encoded by exon 7 and 8 of the ER-α66 (FIG. 1). Here, this novel isoform of ER-α is herein named ER-α36.

Figure 9:
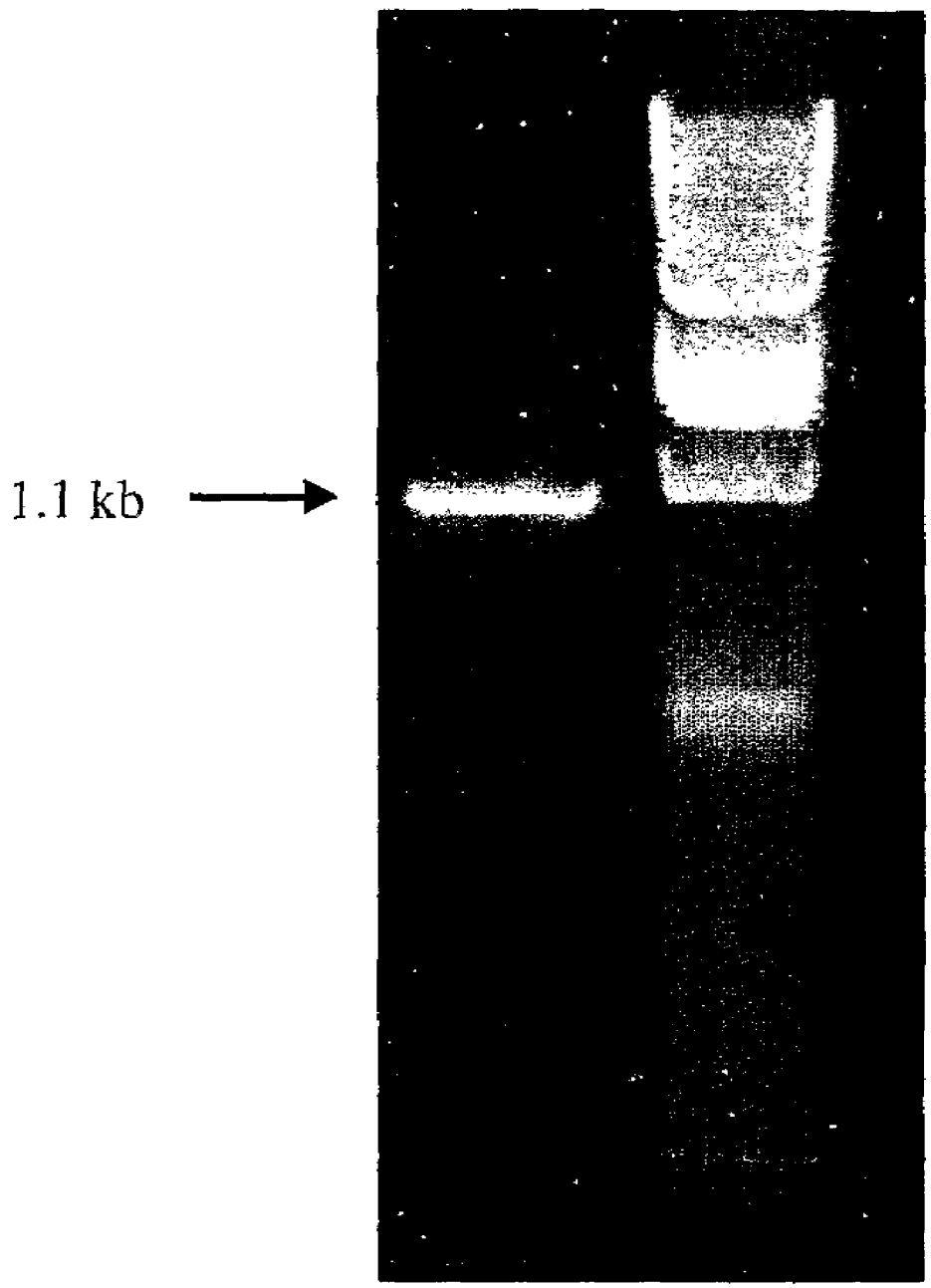
FIG. 9 is a picture of an agarose gel showing the isolation of cDNA encoding the open-reading frame of ER-α36 by PCR. The position of the cDNA in the gel is indicated by an arrow.

The open reading frame encoding ER-α36 was obtained by using the PCR from the Marathon Ready cDNA prepared from human placenta RNA (Clonetech) according to the procedure described by the manufacture. The PCR primer pairs are designed according to the cDNA sequence of DKFZp686N23123. The 5' primer is 5'-CGGAATTC-CGAAGGGAAGTATGGCTATGGAATCC-3' (SEQ ID NO:23) with an EcoRI site at the end, and the 3' primer is 5'-CGGGATCCAGAGGCTTTAGACACGAGGAAAC-3' (SEQ ID NO:24) with a BamHI site at the end. The PCR product was subjected to electrophoresis on a 1% agarose gel, and an expected 1.1 kb DNA fragment was observed (FIG. 9). The DNA fragment was purified, digested with EcoRI and BamHI, cloned into a pBluescript vector (pBS-ER-α36) and fully sequenced. The sequence showed 100% identity to the cDNA clone DKFZp686N23123, indicated that ER-α36 is a naturally occurring isoform of ER-α that can be cloned from another source. The predicted amino acid sequence encoded by the open-reading frame is shown in FIG. 10.

Figure 11:
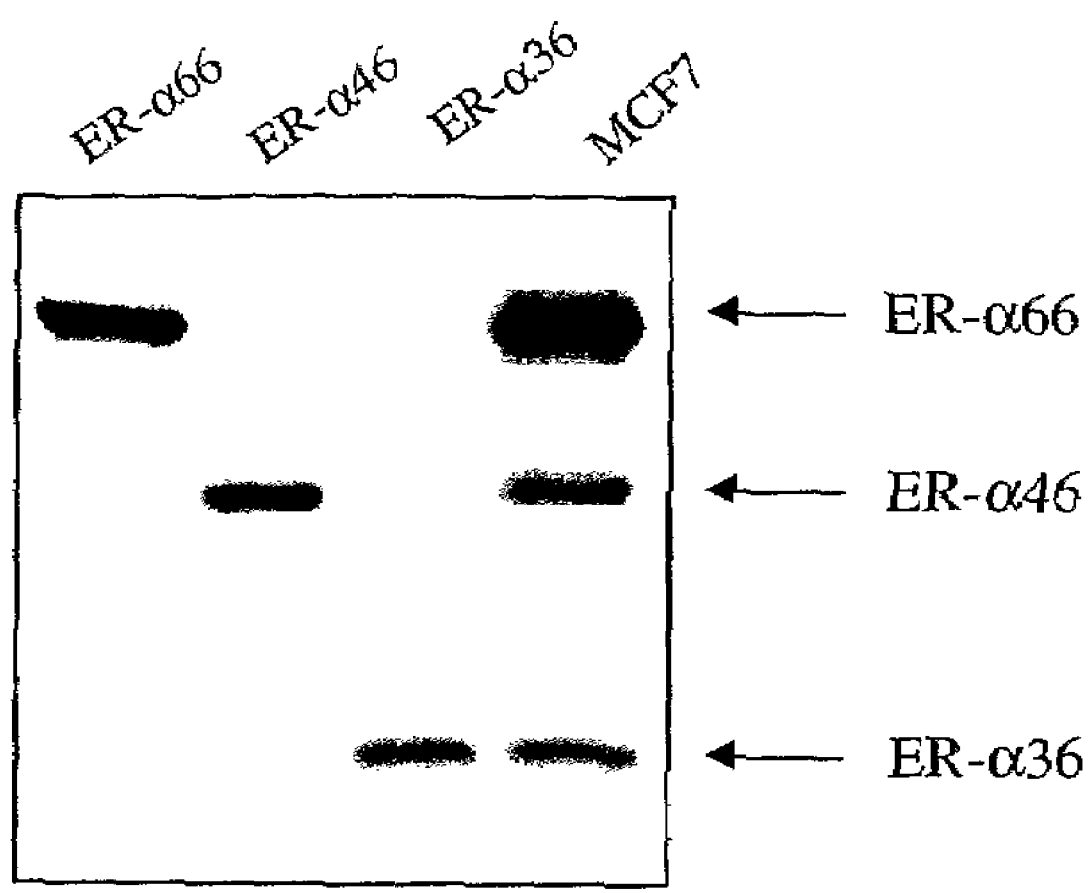
FIG. 11 shows a Western blot analysis of ER-α66, ER-α46 and ER-α36. The lanes marked ER-α66, ER-α46 and ER-α36 represent separated cultures of HEK 293 cells that were transfected with expression plasmids encoding the indicated estrogen receptor isoform, and lysed two days after being transfected. The lysate of each transfectant was immunodetected with an anti-ER-α antibody (H222). The cell extracts from MCF7 cells used as a positive control. The positions of ER-α66, ER-α46 and ER-α36 are indicated by arrows.

Transient transfection assays were performed in human embryonic kidney 293 cells using expression vectors containing ER-α66, ER-α46 and ER-α36 to test whether the cloned cDNA will produce the ER-α36 protein. Whole cell extracts from these transfected cells and MCF7 cells were subjected to western blot analysis with the monoclonal antibody H222 raised against the ligand-binding domain of ER-α (Abbondanza et. al., Steroids, 58:4 (1993)). A 36 kDa protein that was recognized by the H222 antibody was produced in ER-α36 vector transfected cells (FIG. 11). The size of this protein and its failure to react with the antibody H226 directed to the B-domain of the ER-α66, and with the antibody HC 20 which recognizes the C-terminal of ER-α66, indicates that the ER-α isoform lacked both the N-terminus and C-terminus of ER-α66, resulting in an ER-α lacking both AF-1 and AF-2 domains.

A series of computer searches were performed on the ER-α36 protein. FindMod and SCANPROSITE algorithms predicted three myristoylation sites in ER-α36, suggesting that it may localize in the peripheral membrane. This is in agreement with the k-nearest neighbors (PSPORT II) algorithm that predicts 21.7%, 34.8%, 17.4%, and 26% of ER-α36 is localized to the nucleus, cytoplasm, mitochondria, and membrane fractions, respectively. This is similar to the prediction for ER-α46 (26.1%, 30.4%, 17.4%, and 26.1%, respectively). By contrast, 73.9% 8.7%, 0.1% and 17.3% of ER-α66 carries comparative predictions. Thus, the differential compartmentalization of ER-α66, ER-α46, and ER-α36 indicates that the functional site and primary role of each receptor may be different.

A computer search was also performed on the putative 5' flanking region of the gene encoding ER-α36 that is located in the first intron of ER-α66 gene. A TATA binding protein (TBP) recognition sequence was found upstream of the cDNA start site and several Sp1, NF-κB and Ap1 binding sites in the 5' flanking region (FIG. 12). A perfect half estrogen response element (ERE) site was identified at the 5' upstream region of ER-α36, indicating that ER-α36 is subjected to E2-mediated transcriptional regulation.

Example 3

ER-α36 Mediates Membrane-initiated Estrogen Signaling and is Expressed in ER-negative Breast Cancer Methods Cell culture, establishment of stable cell lines and membrane-labeling with E2-BSA-FITC. MCF10A cells were obtained from Karmanos Cancer Institute at Detroit, Mich., and human embryonic kidney 293 cells, and all breast cancer cells were obtained from ATCC. All cells were maintained at 37° C. in a 5% $CO_2$ atmosphere in appropriate tissue culture medium. To establish stable cells that express recombinant ER-α36, HEK293 cells were plated at a density of $1 \times 10^5$ cells per 60-mm dish and transfected 24 hours later with ER-α36 expression vector driven by the cytomagalovirus (CMV) promoter using the FuGene6 transfection reagent (Roche Molecular Biochemicals). The ER-α36 expression vector was constructed by cloning a 1,1-kb EcoRI-BamHI cDNA fragment of ER-α36 from pBS-ER-α36 into the EcoRI and BamHI sites of mammalian expression vector pCB6+. Empty vector was also transfected into cells to serve as controls. Forty-eight hours after transfection, the cells were replated and selected with 500 µg/ml of G418 (Invitrogen) for two weeks. The resulting uncloned population of G418-resistant cells was expanded to generate cells used for further analysis. To label the cell surface of stable cells that express recombinant ER-α36, cells were labeled at 4° C. for 15 minutes with 1 µM fluorescein isothiocyanate (FITC)-labeled BSA covalently attached to E2β-hemisuccinate (Sigma), fixed in freshly prepared 4% paraformaldehyde and mounted with mounting solution containing DAPI for microscopic evaluation.

Cellular stimulation with estrogens and anti-estrogens, and MTT assay. Before treatment, cells were cultured in phenol-red free medium with 2.5% dextrin-coated charcoal-stripped Fetal Calf Serum for 48-72 hours, and then washed with PBS and placed in fresh phenol red-free, serum-free medium containing 0.1 µg/ml of BSA and 5 µg/ml of insulin for 12 hours. Stimulation of quiescent cells was carried out at 37° C. in serum free medium for different period of time. Different estrogens and antiestrogens were purchased from Steraloids Inc. BSA-E2β was obtained from Sigma.

For 3-(4,5-dimethylthiazol-2-yl)-2,5-diphenyltetrazolium bromide (MTT) assays, cells in suspension were added to each well of a 96-well culture plate for a final concentration of $1 \times 10^3$ cells/well, and incubated for 24 hours at 37° C. in a $CO_2$ incubator. Media containing 10 nM E2β, 10 nM of Tamoxifen or 4OH-Tamoxifen or 7.2 nM UO126 (Calbiochem) were added to each well for 48 hours. MTT assay was performed with the CellTiter96 Aqueous One Solution Cell Proliferation Assay Kit (Bio Rad) as the manufacture recommended. A microplate reader (Promega) was used to measure absorbance at 490 nm.

Cell fractionation assay. Cell fractionation was done as described by Márquez et al. (*Oncogene*, 20, 5420-5430 (2001)).

Western blot analysis, indirect immunofluorescence and antibodies. For Western blot analysis, cells were disrupted with RIPA buffer, boiled in gel loading buffer and separated on a 10% SDS-PAGE gel. After electrophoresis, the proteins were transferred to a PVDF membrane (Millipore). The filter was probed with various antibodies and visualized with appropriate HRP-conjugated secondary antibodies (Santa Cruz Biotechnology) and ECL reagents (Perkin Elmer Life Sciences).

Antibody against ERK1/2 (K-23) was purchased from Santa Cruz Biotechnology. Antibodies used to analyze activation of the MAP kinase pathway included the phosphorylated forms of Mek1 and ERK1/2, and were purchased from Cell Signaling Technology. Rat anti-ER-α antibody (H222) was purchased from Research Diagnostic Inc. Antibodies of COPB (Y-20), mSin3A (AK-11), and 5'nucleotidase (H-300) were purchased from Santa Cruz biotechnology Inc. D4-GDI (clone 97A1015) was obtained from Upstate Biotechnology.

The polyclonal anti-ER-α36 antibody was raised in rabbit against the synthesized peptide antigen according to the last 15 amino acids at the C-terminal region of ER-α36 that are unique to ER-α36 (Alpha Diagnostic Inc.). An affinity column of synthesized peptide used to raise the antibody was used to purify the antibody. The specificity of the antibody has also been tested in ER-α36 expression vector transfected HEK293 cells that do not express endogenous ER-α36. Immunofluorescence assay showed that immunoreactive signals of the anti-ER-α36 antibody were detected only in transient transfectants with ER-α36-expressing vectors but not in transfectants expressing a mutant ER-α36 lacking the C-terminus, suggesting that the ER-α36 antibody is highly specific.

DNA transfection and luciferase assay. For transient transfection assays, HEK293 cells subseeded in 6 well dishes were grown to 60-70% confluence in phenol-red free medium plus 2.5% steroid-free fetal calf serum. Cells were washed and transiently transfected with total 5 µg of plasmids (2 µg of the reporter plasmid 2×ERE-tk-Luc together with 1.5 µg of the expression vector pSG5, 1.5 µg of pSG hERα66 or 1.5 µg of pSG hERβ alone or with 1.5 µg of ER-α36 expression vector) with FuGene6 reagent (Roche Molecular Biochemicals). A reporter plasmid containing two EREs (sequence from −331 to −289 of the chicken Vitellogenin A2 gene) placed upstream of the thymidine kinase promoter (2×ERE-tk-Luc, obtained from Dr. Katarine Pettersson, Karolinska Institute, Sweden) was used. The expression vectors containing ER-α66 and β were also obtained from Dr. Katarine Pettersson. The expression vector of ER-α46 was obtained from Dr. Zafar Nawaz (Creighton University Medical Center, Omaha, Nebr.). Cells were treated with or without E2 (10 nM) for 12 hours before being assayed for luciferase activity. Luciferase assays were performed using the Luciferase Assay kit from Promega. Values correspond to the average ±standard deviation of more than three separate transfection experiments.

RNA extraction and Northern blot analysis. Total cellular RNA was isolated using Trizol (Invitrogen), according to the manufacturer's instruction. Ten µg of total RNA was separated by electrophoresis on a 1.2% formamide/formaldehyde gel and blotted onto a nylon membrane (Hybond-N, Amersham Pharmacia Biotech). The blots were prehybridized for 1 hour and hybridized for 2 hours in Quick-Hybridization solution (Amersham Pharmacia Biotech) at 65° C. The probes included a 410 bp cDNA fragment from the 3' untranslated region of ER-α36 that is unique to ER-α36, and a β-actin DNA probe from BD Clonetech. The DNA probes were labeled with $^{32}P$ dCTP and a Rediprime II DNA labeling kit (Amersham Biotech). Blots were autoradiographed using intensifying screens at −70° C. overnight. The same membranes were stripped and reprobed with a labeled β-actin DNA probe to confirm equal loading.

Breast cancer specimens and immunohistochemistry assay. Paraffin-embedded human breast cancer specimens were obtained from the Department of Pathology, the Sir Run Run Shaw Hospital, Hangzhou P. R. China. Immunohistochemical staining was done using UltraSensitive™ S-P kit (Maixin-Bio, China) according to the manufacturer's instruction, with an ER-α66 specific antibody (LabVision Corporation, USA) and the ER-α36 specific antibody as primary antibody, respectively.

Results

Figure 13:
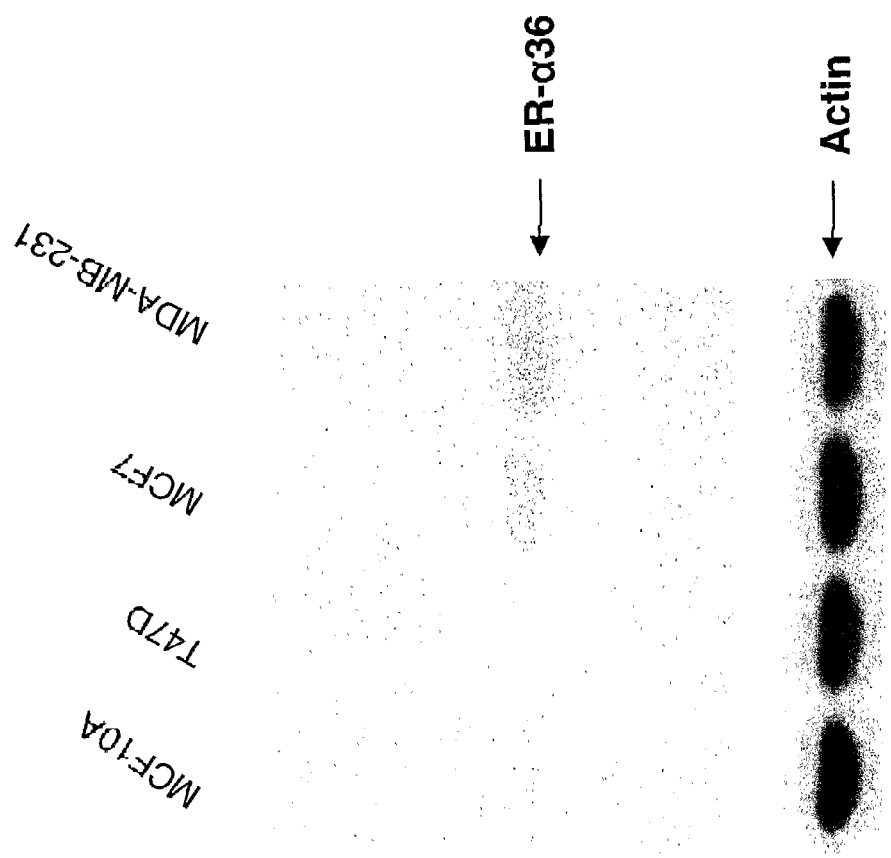
FIG. 13 shows Northern blot analysis of ER-α36 in different breast cancer cells MCF10A, T47D, MCF7, and MDA-MB-231. The positions of ER-α36 and actin are indicated by arrows.

To further confirm that ER-α36 is a naturally occurring isoform of ER-α 66, Northern blot analysis of total RNA from a normal mammary epithelial cell line, MCF10A, and ER-positive and -negative (i.e., ER-α66-positive and -negative) breast cancer cells was performed. A DNA probe was synthesized using the RT-PCR method with the primer pairs designed according to the 3' untranslated region of the ER-α36 that is unique to ER-α36 (5' GCAAAGAAGAGAATC-CTGAACTTGCATCCT (SEQ ID NO:26) and 5' TTAGT-CAGGTATTTAATAACTAGGAATTG (SEQ ID NO:27)). The Northern blot analysis showed that a single mRNA with estimated size of 5.6 kb was identified in ER-positive (i.e., ER-α66-positive) breast cancer cells MCF7 but not in MCF10A cells (FIG. 13). Surprisingly, ER-α36 was also expressed in MDA-MB-231 cells, a well known ER-negative (i.e., ER-α66-negative) breast cancer cell line (FIG. 13). This data indicates that transcripts with the predicted size of the ER-α36 mRNA are expressed in breast cancer cells, and even in breast cancer cells that lack the ER-α66.

Figure 14:
FIG. 14 shows inhibition by ER-α36 of the transcriptional transactivation activities mediated by the AF-1 and AF-2 domains of ER-α66 and ER-β. (+E2), cells treated with E2; (−E2), cells not treated with E2.

ER-α36 inhibits transactivation activities of liganded- and unliganded-ER-α66 and -β. We first tested whether ER-α36 that lacks both AF-1 and AF-2 domains retains any transcriptional activity. Transient transfection assays were performed in HEK293 cells using a luciferase-expressing reporter construct that contains two estrogen response elements (ERE) placed upstream of the thymidine kinase promoter (2×EREtk-Luc). The HEK293 cell line was selected since it was reported previously that the AF-1 and -2 of ER-α66 function equally well in HEK293 cells (Denger et al., Mol. Endocrinol., 15, 2064-2077 (2001)). As shown in FIG. 14, we found that ER-α36 exhibits no intrinsic transcriptional activity in the presence and absence of E2β, consistent with the finding that ER-α36 lacks both transcription activation domains. We then assessed the regulatory function of ER-α36 in transcriptional transactivation activities mediated by the AF-1 and -2 domains of the ER-α66. Co-expression of ER-α36 strongly inhibited the transactivation activity of ER-α66 in the presence and absence of E2β (FIG. 14), suggesting that ER-α36 inhibits the transactivation activities mediated by the AF-1 and AF-2 domains of ER-α66. Furthermore, ER-α36 also inhibited ligand-dependent and -independent transactivation activities of ER-β (FIG. 14).

Figure 15A:
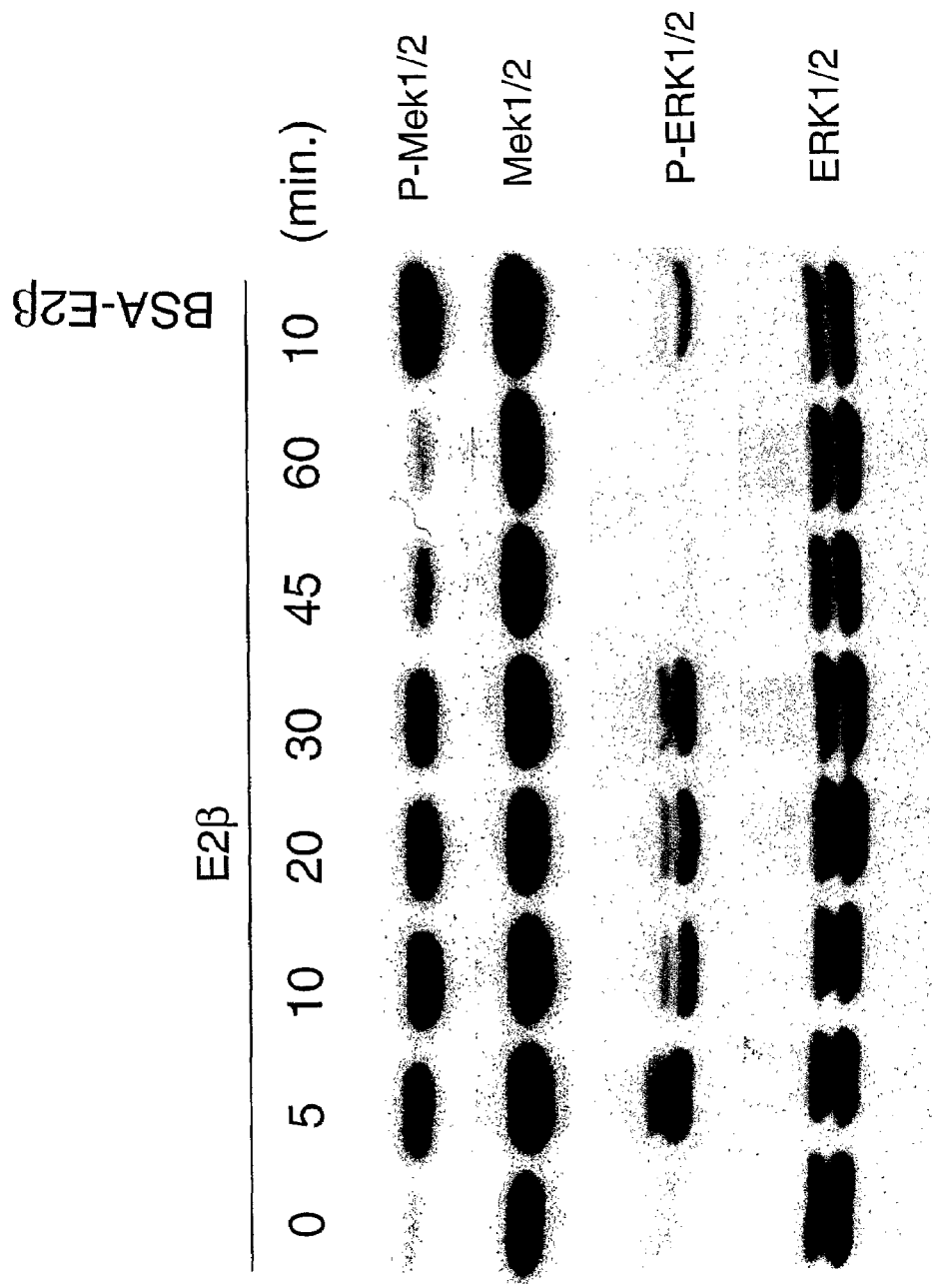
FIG. 15 shows ER-α36 mediates membrane-initiated MAPK kinase pathway stimulated by E2. (a) Western blot shows treatment of ER36-293 cells with estradiol-17β (E2β) induces rapid phosphorylation of Mek1/2 and ERK1/2. P-Mek1/2 and P-ERK1/2, phosphorylated forms of Mek1/2 and ERK1/2, respectively. (b) Serum but not E2β induces phosphorylation of ERK1/2 in control vector-293 cells. P-ERK1/2, phosphorylated form of ERK1/2. (c) Different estrogens and antiestrogens induce rapid phosphorylation of ERK1/2 in ER36-293 cells. P-ERK1/2, phosphorylated form of ERK1/2. (d) Tamoxifen treatment constitutively stimulates ERK1/2 phosphorylation in ER36-293 cells. P-ERK1/2, phosphorylated form of ERK1/2.
Figure 15B:
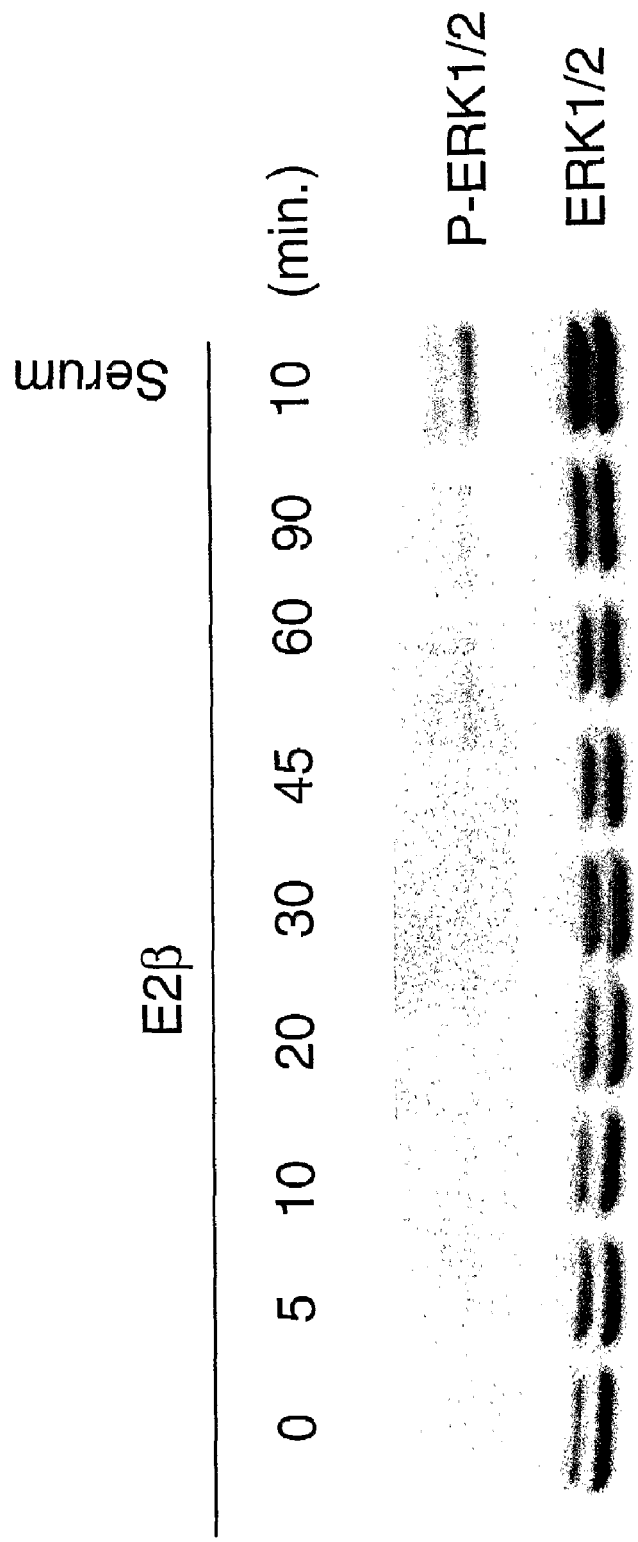

ER-α36 mediates membrane-initiated estrogen signaling pathway. Previous reports have indicated that E2O stimulates a rapid activation of the MAPK/ERK pathway (Razandi et al., Mol. Endocrinol., 13, 307-319 (1999), Watters et al., Endocrinol., 138, 4030-4033 (1997), and Migliaccio et al., EMBO J., 15, 1292-1300 (1996)). To determine whether ER-α36 is involved in this signaling pathway, we established stable cells that express exogenous ER-α36 in HEK293 cells that do not express endogenous ER-α. Whole ER-α36 transfected HEK293 cells were incubated with fluorescein isothiocyanate (FITC)-conjugated E2β-BSA (E2β-BSA-FITC) that is membrane impermeable. The cell surface of the ER-α36 transfected cells was strongly labeled by the E2β-BSA-FTIC whereas the control cells transfected with empty vector were not labeled by E2β-BSA-FITC. Cell lysates were prepared from quiescent cells that were either untreated or treated with E2β (10 nM) for various lengths of time. ERK activation was measured by immunoblotting using phosphorylation state-dependent and -independent antibodies. A 10-fold increase in the phosphorylation of ERK1/2 that lasted about 45 minutes was observed within 5 minutes in the cells transfected with ER-α36 expression vector but not in the control cells transfected with empty vector (FIGS. 15a and 15b). However, serum (20% for 10 minutes) was able to activate ERK1/2 in these control cells (FIG. 15b), indicating that there is no global defect of the MAPK signaling pathway in these cells. Furthermore, Mek1, the kinase that phosphorylates and activates ERK1/2, is also activated in response to E2β in ER-α36 transfected cells (FIG. 15a). To provide further evidence for activation of the ERK1/2 by a membrane-initiated estrogen signaling, ER-α36 transfected cells were also treated with E2β-BSA, a membrane impermeable form of E2β. A strong activation of ERK1/2 phosphorylation was also observed in E2β-BSA treated cells (FIG. 15a).

Figure 15C:
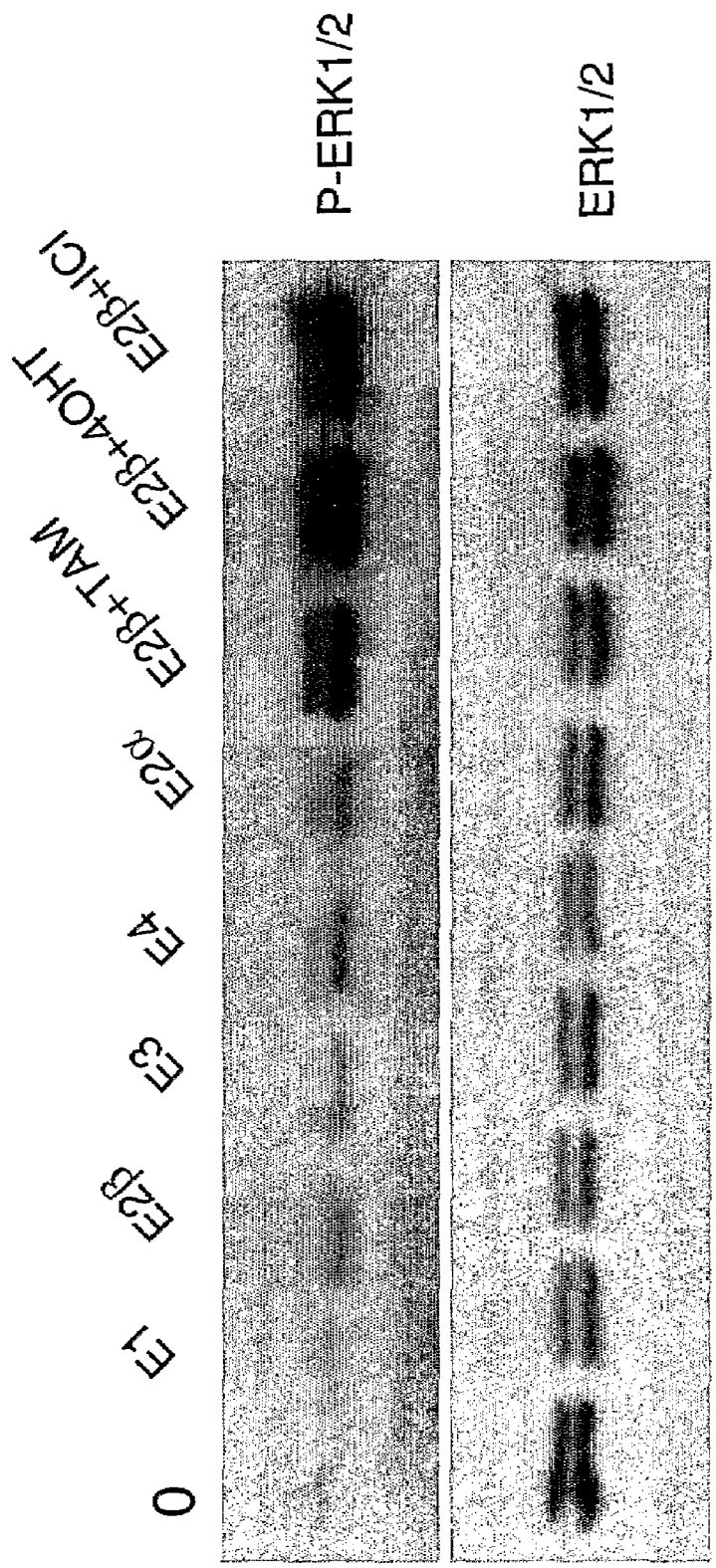
Figure 15D:
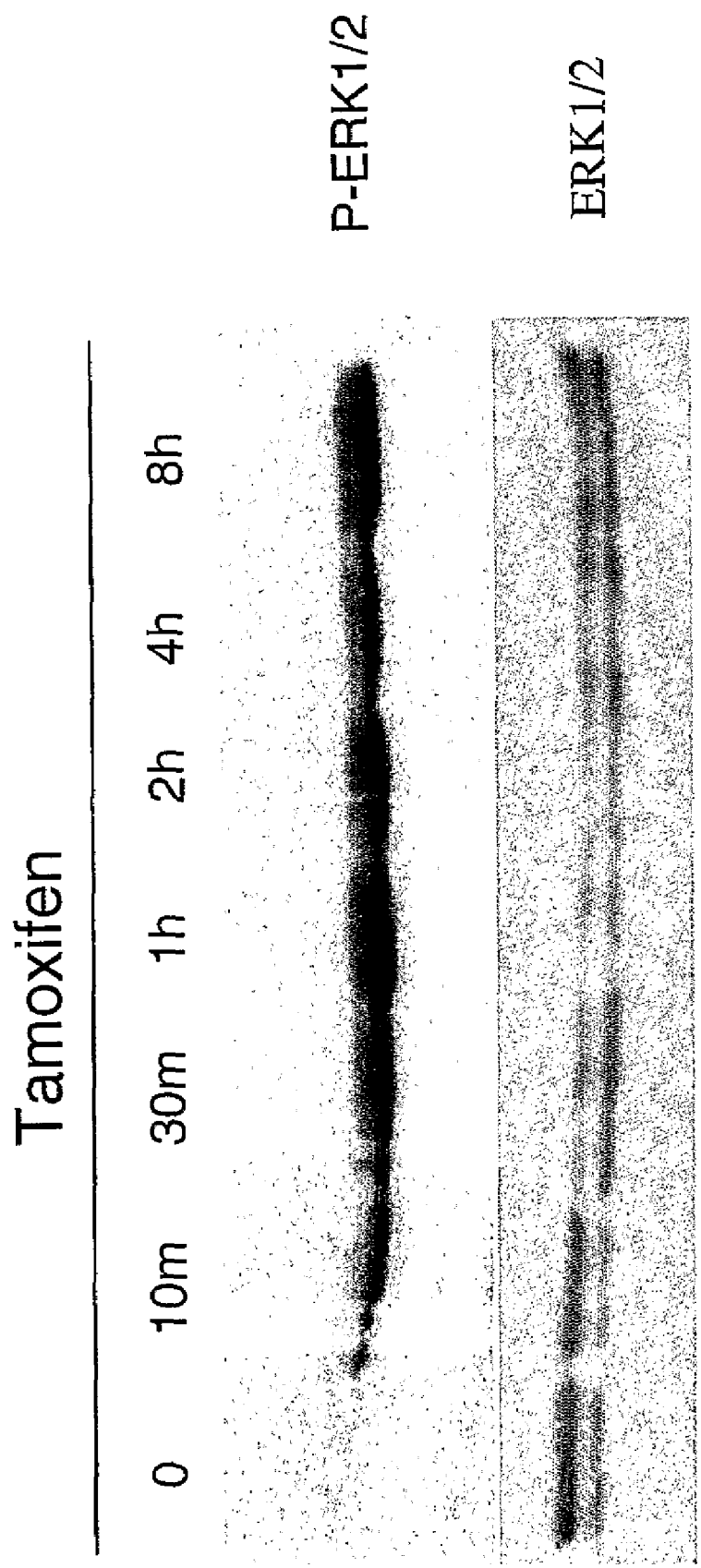

ER-α36 mediates activation of the MAPK signaling pathway stimulated by different estrogens and anti-estrogens. We also treated ER-α36 transfected cells for 10 minutes with estrone (E1), 17β-estradiol (E2β), 17α-estradiol (E2α), estriol (E3), or estetrol (E4), and found that all of these estrogens except E1 activated ERK1/2 phosphorylation at a very similar level, suggesting ER-α36 may recognize these estrogens at a similar level (FIG. 15c). We then included the anti-estrogens including Tamoxifen, 4OH-Tamoxifen, ICI-182, 780 in the experiment to test whether ER-α36 mediated estrogen signaling is sensitive to anti-estrogens. Tamoxifen, 4OH-Tamoxifen and the pure anti-estrogen ICI-182, 780 did not block ERK1/2 activation mediated by ER-α36. On the contrary, the effects are even stronger compared to the effects mediated by E2β alone (FIG. 15c). When ER-α36 transfected cells were treated with 1 μM Tamoxifen alone, a concentration that can blunt both ER-α66 and β, a strong and persistent ERK1/2 activation that lasted longer than eight hours was observed (FIG. 15d). Tamoxifen at the same concentration, however, had no effect in control 293 cells transfected with empty expression vector.

ER-α36 mediates E2-stimulated cell proliferation. To further determine whether the estrogen activated MAPK pathway mediated by ER-α36 can lead to the transcriptional signaling in cell nucleus, we examined the ability of membrane-initiated estrogen signaling to activate the transcription factor Elk, a downstream effector of the MAPK/ERK signaling pathway. We transiently transfected ER-α36 expressing 293 cells with the ERK-responsive GAL-Elk chimeric transcription factor, consisting of the DNA-binding domain of yeast transcription factor GALA fused to the ERK-responsive trans-activation domain of human Elk1, and measured its activity in vivo on the expression of a GAL4-binding reporter gene in the presence of E2β. The reporter gene was 5×Gal4-LUC, a luciferase reporter plasmid containing five Gal4 DNA binding sites. A bacteria β-galactosidase expression vector was used to control transfection efficiency. After transfection, the cell culture was maintained in estrogen free medium for 36 hours before E2β (10 nM) was added for 12 hours. Luciferase activities with standard deviation are representative of more than three experiments performed in duplicates. Estrogen treatment of ER-α36 transfected cells induced about two-fold increase of Elk/Gal4 fusion protein-mediated trans-activation of the reporter whereas E2β had no effect on the transcription activity of the Elk/Gal4 fusion protein in the control cells transfected with empty vector (FIG. 16a).

Figure 16B:
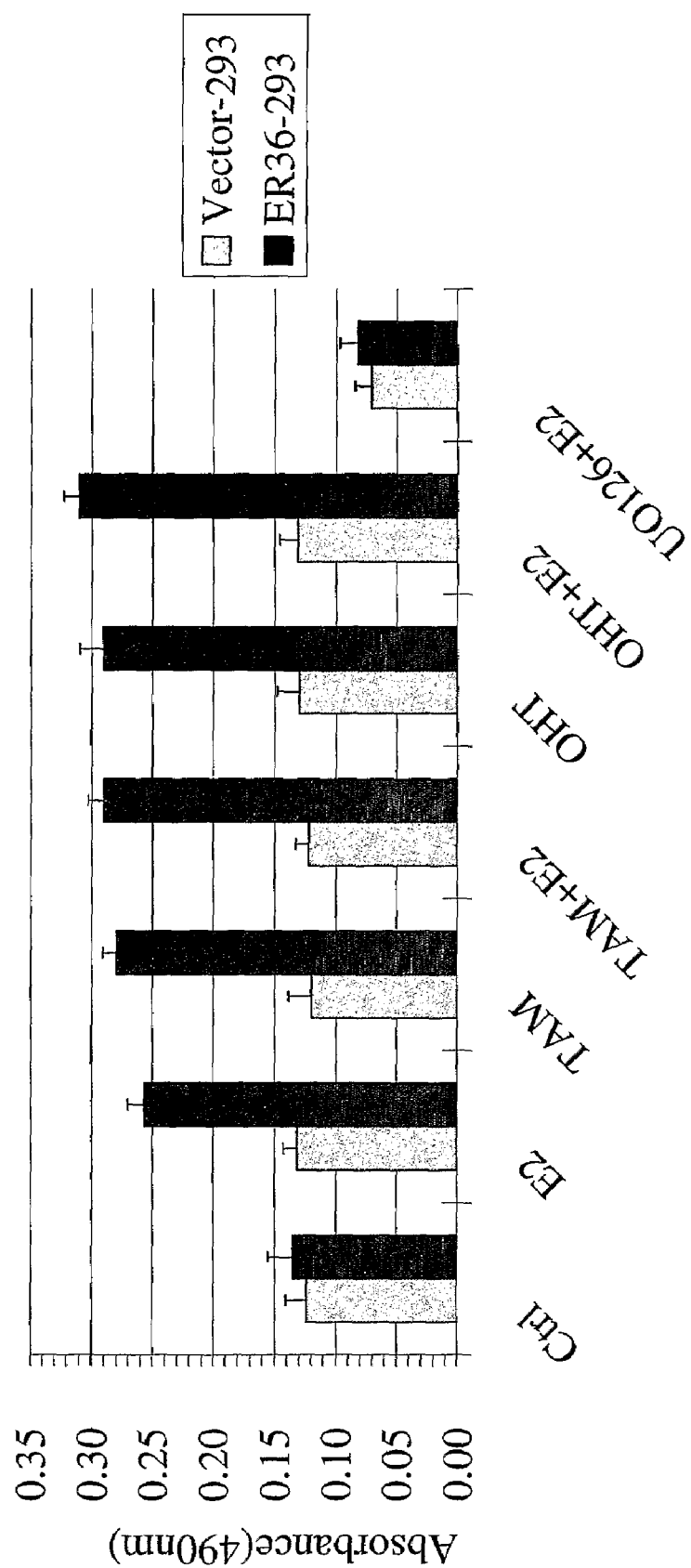
FIG. 16 shows ER-α36 mediates E2β induced MAPK kinase nuclear signaling and stimulates cell growth. (a) Effects of E2β on MAPK kinase nuclear signaling. ER36-293 and control vector-293 cells were transiently transfected with 5×Gal4-LUC, a luciferase reporter plasmid containing five Gal4 DNA binding sites, and Gal-ELK expression vector containing an ELK transcriptional activation domain fused with the Gal4 DNA binding domain (Upper panel). After transfection, the cell culture was maintained in estrogen free medium for 36 hours before E2β (1 nM or 10 nM) was added for 12 hours. Luciferase activities with standard deviation are representative of more than three experiments performed in duplicates. (b) E2β and anti-estrogens stimulate growth of ER36-293 cells. Absorbance data at 490 nm are shown. Results of more than five independent experiments have were averaged; the mean and SEM are shown. The statistical significance of these results was also evaluated by paired t-test. P-values were <0.001 for ER36-293 and vector-293 cells.

We next addressed whether the ER-α36 can mediate estrogen-stimulated cell proliferation. Proliferation of the ER-α36 transfected cells and control cells in the presence and absence of E2β was evaluated by the MTT assay. Proliferation of ER-α36 transfected cells was stimulated by E2β treatment while E2β had no effect on the growth of the control cells transfected with empty expression vector (FIG. 16b). The inclusion of the anti-estrogens including Tamoxifen and 4OH-Tamoxifen did not block E2β-stimulated cell growth (FIG. 16b). Tamoxifen or 4OH-Tamoxifen alone strongly stimulated growth of the ER-α36 transfected cells. However, the specific inhibitor of MAPK pathway, UO126, strongly inhibited E2β-stimulated cell growth. These data suggest that ER-α36-mediated membrane estrogen signaling stimulates cell growth through activation of the MAPK/ERK signaling pathway. The data also suggest anti-estrogens also stimulate cell growth through ER-α36.

Figure 17A:
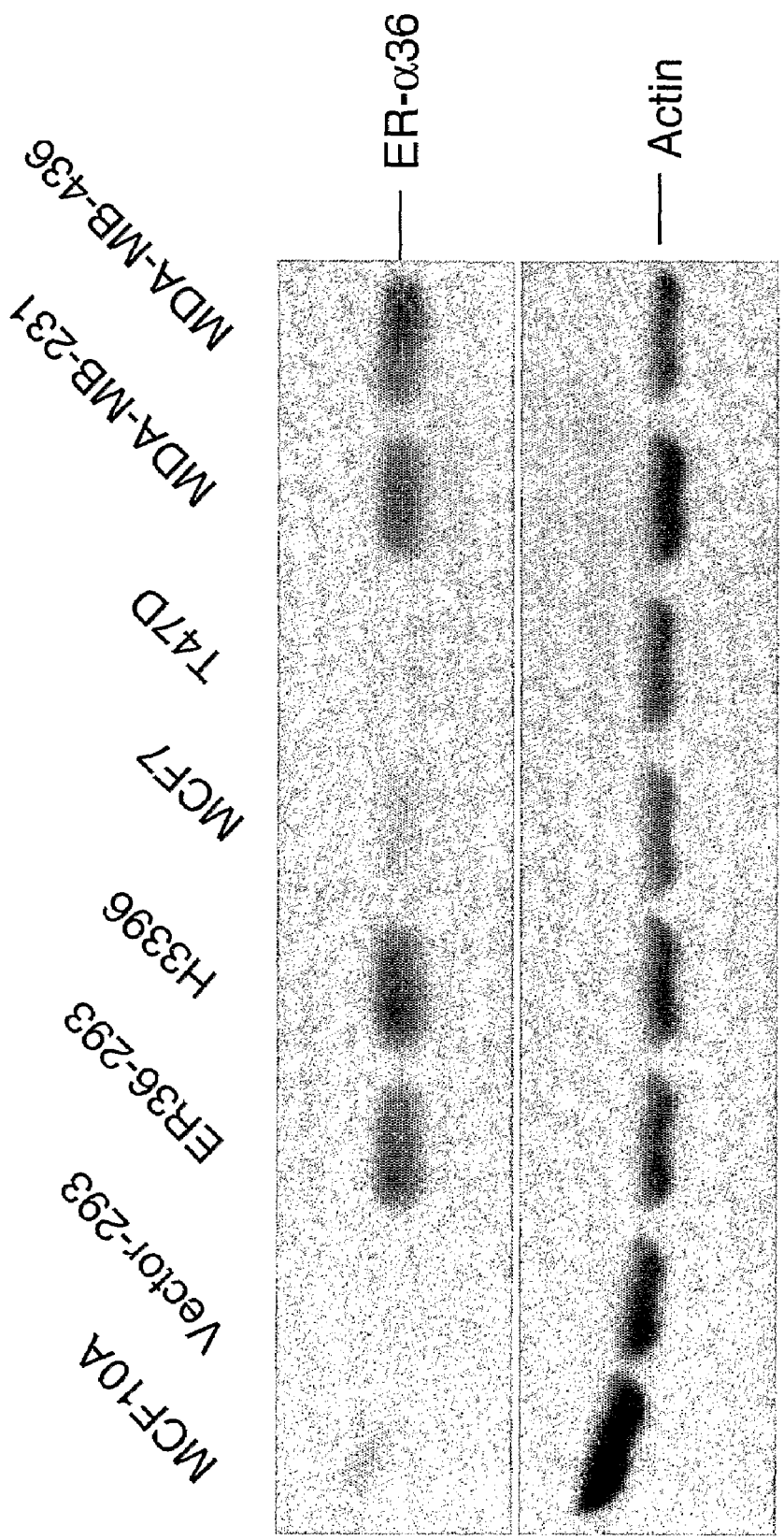
FIG. 17 shows ER-α36 is mainly a membrane-based estrogen receptor. (a) Western blot analysis of expression of ER-α36 in different established breast cancer cell lines. The same blot was stripped and probed with an anti-actin antibody to ensure equal loading. (b) Subcellular localization of ER-α36 in ER-α36 transfected 293 cells. Immunoblot of ER-α36 in different subcellular fractions with the ER-α36 specific antibody. W, whole cell lysate; PM, plasma membrane; C, cytosol; N, nucleus. Subcellular fraction purity was examined by immunoblotting various protein markers for the plasma membrane, cytosol, nucleus and Golgi. 5'NT, 5'nucleotidase; D4-GDI, GDP dissociation inhibitor; mSin3A, a component of histone remodeling complex; COPB, β coat protein.

ER-α36 is predominantly a membrane-based estrogen receptor. To further characterize ER-α36, we have successfully developed a polyclonal anti-ER-α36 antibody raised against the 15 amino acids at the C-terminal region of ER-α36 that are unique to ER-α36. An affinity column of synthesized peptide used to raise the antibody was used to purify the antibody. Western blot analysis of proteins prepared from normal mammary epithelial cells and established breast cancer cell lines using this antibody demonstrated a single protein band with 37-kDa molecular weight in some breast cancer cells but not in normal mammary epithelial cells (FIG. 17a). ER-α36 is expressed in MDA-MB-231, MDA-MB436 and HB3396 cells, three well-known ER-α66 negative breast cancer cell lines, and also is expressed in ER-α66 positive breast cancer cells MCF7 but not in T47D (FIG. 17a), consistent with our Northern blot data that ER-α36 is expressed in ER-α66 negative breast cancer cells. To evaluate further the possibility that ER-α36 is expressed in ER-α66 negative breast cancer cells, indirect immunofluorescent assay and confocal microscopy in permeabilized MDA-MB-231 cells using the anti-ER-α36 specific antibody showed that ER-α36 is expressed on the plasma membrane, cytoplasm and nucleus of the ER-α66 negative breast cancer cells, MDA-MB-231.

Figure 17B:
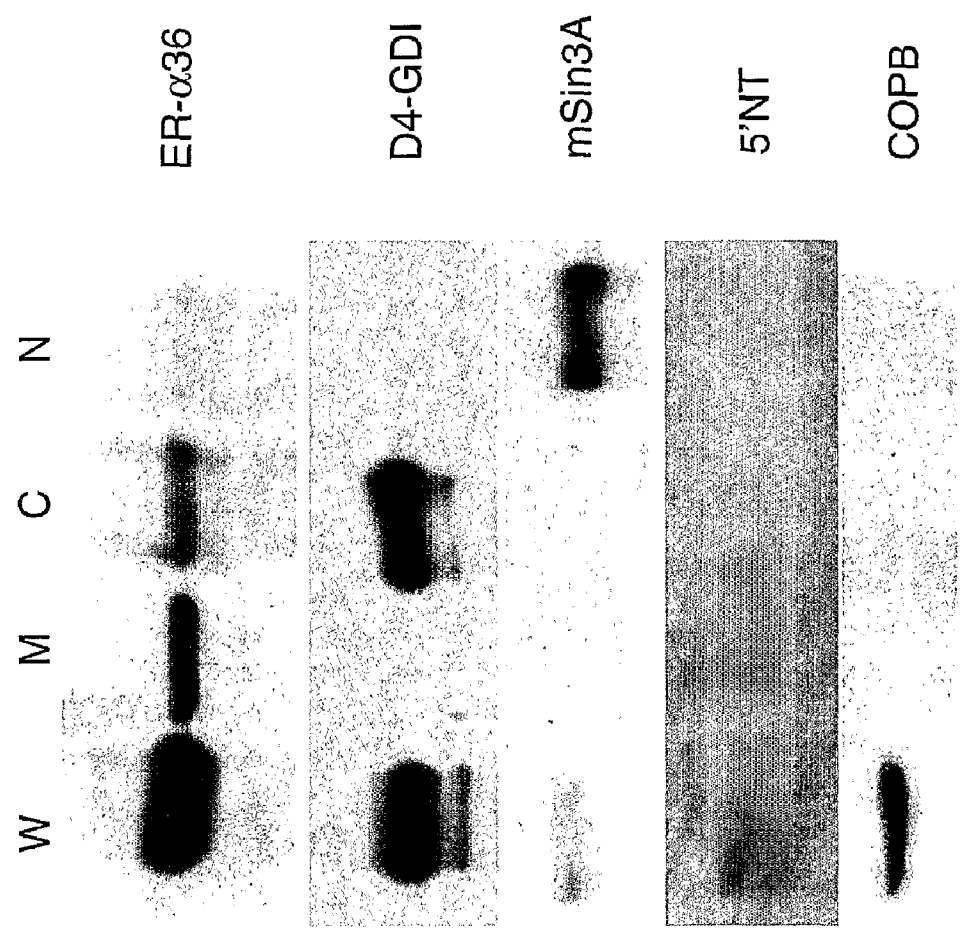

To further assess the ER-α36 compartmentalization in cells, the subcellular fractionation assay was performed to isolate nuclei, plasma membranes, and cytosol from ER-α36 transfected HEK293 cells. ER-α36 was identified by immunodetection from the different fractions. A high percentage of ER-α36 (~50%) was localized on the plasma membrane and a low percentage of it in cytosol (~40%) and nucleus (~10%). To exclude cross-contamination of different fractions, the fraction purity was examined by Western blot analysis with different marker proteins including mSin3A (nucleus), GDP dissociation inhibitor (cytosol), 5'nucleotidase (plasma membrane), and β-COP (Golgi). These results confirmed that there was no contamination among different fractions. This experiment established that ER-α36 is predominantly a membrane-based estrogen receptor (FIG. 17b).

ER-α36 is expressed in ER-α66 negative breast cancer specimens. To further determine the relevance of ER-α36 to human breast cancer, we examined the ER-α36 expression patterns in human breast cancer specimens with an immunohistochemistry assay using the specific anti-ER-α36 antibody. In situ analysis of human breast tissue showed the up-regulation of ER-α36 in breast cancer. Cells that were positive for ER protein stained brown, and nuclei were stained blue with hematoxylin. Among 35 cases of breast cancer specimens examined, 21 of them (60%) stained positive for ER-α36, and 21 of them (60%) positive for ER-α66 (Table 2). Consistent with our Northern and Western blot analyses, 11 out of 14 (78%) breast cancer specimens that stained negative for ER-α66 were stained positive for ER-α36, indicating most ER-negative (i.e., ER-α66-negative) breast cancers still express ER-α36. In situ staining of ER-α36 in a normal section of tissue found in a human ductal carcinoma showed ER-α36 expression only in lumenal epithelial cells and mainly localized in cytoplasm and plasma membrane. Tumor sections were from human infiltrating ductal carcinoma and from invasive ductal carcinoma. All 21 cases ER-α36 positive specimens exhibited ER-α36 immunostaining patterns predominantly outside of the cell nucleus, contrary to the mainly nuclear staining of ER-α66. Like ER-α66, some luminal epithelial cells in neighboring normal tissue were also stained positive for ER-α36. These results demonstrate that like ER-α66, ER-α36 is expressed in two-thirds of the human breast cancer examined, and suggest that ER-α36 may be involved in development of ER-α66-negative breast cancer.

TABLE 2

ER-α36 and 66 expression: Survey of immunostaining in human breast cancer.

| Case# | ER-α66 | ER-α36 |
|---|---|---|
| 04-06108D | +++ | + |
| 04-06278G | +++ | + |
| 03-19482D | +++ | ++ |
| 03-13610E | +++ | + |
| 01-09182B | ++ | + |
| 02-17950B | ++ | + |
| 02-07748H | ++ | + |
| 01-13537G | ++ | + |
| 00-0319D | ++ | +/− |
| 03-04069G | + | +/− |
| 00-02787D | ++ | − |
| 02-18513F | ++ | − |
| 04-08474J | ++ | − |
| 02-01265M | ++ | − |
| 03-07870E | + | − |
| 02-04206F | ++ | − |
| 02-12985F | +++ | − |
| 03-08862G | ++ | − |
| 02-09537B | +++ | − |
| 03-22792D | ++ | − |
| 04-10881D | + | − |
| 03-10071F | − | ++ |
| 03-22971M | − | + |
| 01-08119D | − | +/− |
| 02-02018D | − | + |
| 02-04567E | − | + |
| 04-07055E | − | + |
| 03-05946C | − | + |
| 03-225861 | − | + |
| 01-02877A | − | + |
| 01-17570C | − | +/− |
| 00-08489G | − | +/− |
| 00-02202F | − | − |
| 98-03898D | − | − |
| 03-04898B | − | − |

In this study, a novel variant of ER-α, ER-α36, has been identified, cloned and characterized. This ER-α isoform is the product of a transcript initiated from a previous unidentified promoter in the first intron of ER-α66 gene. The putative promoter region of the ER-α36 contains a TATA binding protein (TBP) recognition sequence upstream of the ER-α36 cDNA start site, and several Sp1, NF-kB and Ap1 binding sites (FIG. 12). We have cloned the 5' flanking region of ER-α36 and confirmed that it possess strong promoter activity. Furthermore, a perfect half ERE site was identified at the 5' flanking region of ER-α36, suggesting that ER-α36 is subjected to ER-mediated transcriptional regulation.

ER-α36 protein is identical to the ER-α66 protein encoded by exons 2-6 of the ER-α66 gene. This isoform is devoid of the domains previously identified to have transactivation activities, AF-1 and -2. Indeed, analysis of ER-α36 transactivation activity demonstrated that ER-α36 lacks intrinsic transcriptional activity. However, ER-α36 efficiently suppresses the transactivation activities mediated by the AF-1 and -2 domains of liganded- and unliganded-ER-α66 and -β, indicating that ER-α36 is a potent inhibitor of the genomic estrogen signaling. This finding parallels the previous report that ER-α46 that lacks the AF-1 domain functions as a powerful competitor to suppress the AF-1 activity of the ER-α66.

The presence of a plasma membrane-based ER that triggers rapid estrogen signaling was controversial for a long time, since the molecular identity of this receptor has not been established. Previously, Razandi using transfection assay reported that both ER-α66 and -β can initiate membrane estrogen signaling, although only a very small percentage of them was expressed on the cell surface (Razandi et al., Mol. Endocrinol., 13, 307-319 (1999)), suggesting that these ERs may be involved in membrane-initiated estrogen signaling in addition to their traditional roles in genomic estrogen signaling. Recently, the 46-kDa isoform of ER-α was localized on cell surface and found to mediate estrogen-stimulated eNOS phosphorylation (Li et al., Pro. Natl. Acad. Sci. USA, 100, 4807-4812 (2003)). Here, we demonstrated that another ER-α variant, ER-α36, is predominantly localized on the plasma membrane and mediates activation of the MAPK/ERK pathway induced by membrane-initiated estrogen signaling. Moreover, since ER-α36 totally lacks intrinsic transactivation activity and only functions as a regulator of genomic estrogen signaling, ER-α36 may act primarily as a membrane-based estrogen receptor to mediate membrane-initiated estrogen signaling. Previously, it has been reported that some E2β-mediated rapid actions occur in neurons of ER-α gene knockout (aERKO) mice and these actions are not blocked by ICI 182,780 (Gu et al., Endocrinology, 140, 660-666 (1999)), suggesting that the existence of more than one membrane-initiated estrogen signaling pathway. We demonstrated here that anti-estrogens did not block ER-α36-mediated MAPK/ERK activation, suggesting that ER-α36 is involved in the anti-estrogen insensitive signaling pathway previously described. As αERKO mice were created by an insertional disruption of the first coding exon of the mouse ER-α gene (the exon that is skipped in the generation of transcripts of ER-α36), it is likely that the production of the mouse counterpart of ER-α36 remains normal in these knockout mice. Thus, ER-α36 may contribute to the remaining estrogen effects observed in these mice. Recently, Toran-Allerand et al. (J. Neuroscience 22, 8391-8401 (2002)) reported the existence of a novel plasma membrane-associated estrogen receptor (ER-X) with an estimated molecular weight of 63-65 kDa. ER-X shows some similarities with ER-α36, such as reacting with antibodies to the ligand-binding domain of ER-α66 and responding equally well to E2α and β. However, the molecular identity of these two receptors awaits for the cloning and sequencing of ER-X.

We have also shown that ER-α36 promotes membrane-initiated activation of the MAPK/ERK pathway that leads to estrogen-stimulated cell proliferation. Thus, ER-α36, that is devoid of intrinsic transcription activity, is sufficient to promote estrogen-stimulated cell growth, offering support to the previous report that a transcriptionally inactive mutant of ER-α66 induces DNA synthesis. These data together suggest that transcriptional activities of ER may not be required to promote estrogen-stimulated cell growth. Surprisingly, we also observed that anti-estrogens such as Tamoxifen strongly activated the MAPK/ERK signaling and stimulated cell growth during the experiment period (48 hours). This finding is in good agreement with the idea that Tamoxifen functions as both agonist and antagonist of estrogen signaling, and suggests that ER-α36 may be also involved in membrane-initiated anti-estrogen signaling.

It is well known that breast cancer cells with an ER-α66 positive phenotype (ER-positive breast cancer) are more differentiated and have lower metastatic potential than ER-α-negative tumors (McGuire, W. L. Prognostic factors in primary breast cancer. *Cancer Surv.* 5, 527-536 (1986)). It is interesting that ER-α36 is expressed not only in the subset of ER-α66-positive breast cancers but also in most ER-α66 negative breast cancers examined. Corroborating these results, it has been reported that estrogen signaling induced a rapid activation of the PI3K/Akt pathway in MDA-MB-231 cells that could not be blocked by estrogen antagonists (Tsai et al., Cancer Res. 61, 8390-8392 (2001)), which was explained as estrogen signaling through an ER-independent pathway. High concentration of Tamoxifen also has been shown to induce apoptosis in MDA-MB-231 cells (Mandleker et al., Apoptosis 6, 469-477 (2001)). These data strongly suggest that ER-α66-negative breast cancer may still retain estrogen or anti-estrogen effects mediated by membrane-initiated signaling.

ER-α36 also possess a unique ligand-binding domain by replacing the last 5 helixes (helix 8-12) of the 12 helixes in the ER-α66 with a unique 27 amino acid domain, which may change the ligand-binding specificity and affinity of ER-α36. Indeed, we found that ER-α36 elicited membrane-initiated signaling equally well in response to E2α and β, E3 and E4. Thus, ER-α36 appears to possess a much broader ligand-binding spectrum than ER-α66, which makes ER-α36 potentially a more potent mediator of mitogenic signaling. Further analysis of the ligand-binding specificity and affinity of ER-α36 will help design anti-estrogens specific for ER-α36 that can be used to treat ER-α negative (i.e., ER-α66-negative) breast cancer.

Example 4

E2β Promotes Growth of ER-α66 Negative MDA-MB-231 Cells in Soft Agar

Figure 18:
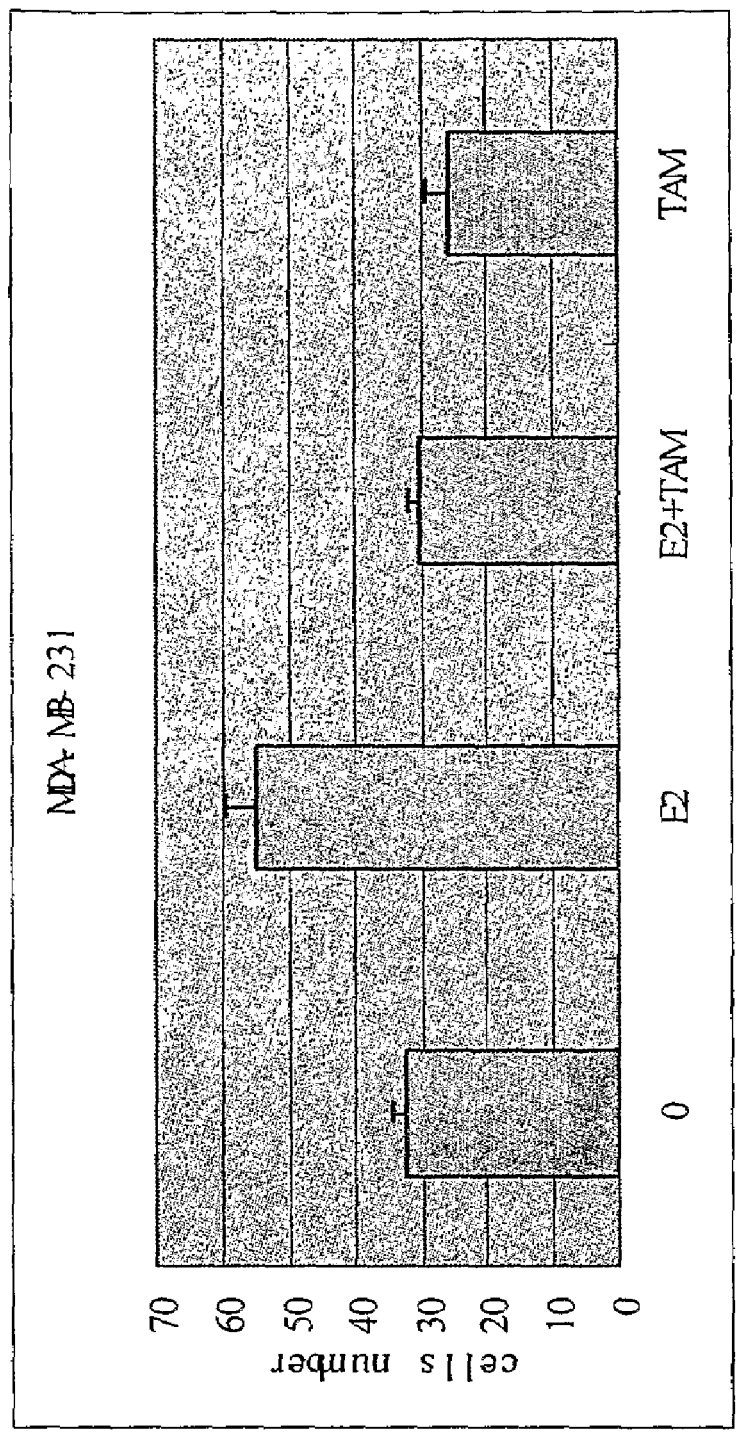
FIG. 18 shows that E2β promotes growth of ER-α66 negative breast cancer cells, MDA-MB-231, in soft agar. MDA-MB-231 cells were grown on soft agar for three weeks in the absence of E2β (0), and in the presence of 10 nM E2β (E2) 10 nM E2β and 10 nM Tamoxifen (E2+TAM) and 10 nM Tamoxifen alone (TAM).

To determine anchorage-independent growth in soft-agar in the presence and absence of E2β and tamoxifen together or separately, five hundred MDA-MB-231 cells were suspended in 3 ml of 3.5% (wt/vol) agar containing phenol red-free DMEM/F12 medium plus 10% E2-free fetal calf serum. The cells were then overlaid onto a 0.7% (wt/vol) agar containing phenol-red free DMEM/F12 medium plus 10% E2-free fetal calf serum in five replica 60 mm dishes. Cells on soft agar were covered with medium plus 10% E2 free fetal calf serum with or without 1 nM E2β, or combined with 1 nM tamoxifen. After three weeks, colonies were scored using an inverted microscope. As seen in FIG. 18, we found that E2 treatment strongly promoted anchorage-independent growth of ER-α66 negative MDA-MB-231 cells in soft agar, whereas anti-estrogen Tamoxifen inhibits the effect of E2β, indicating that ER-α66 negative MDA-MB-231 cells retain responsiveness to estrogen signaling presumably through Er-α36.

Example 5

Figure 19:
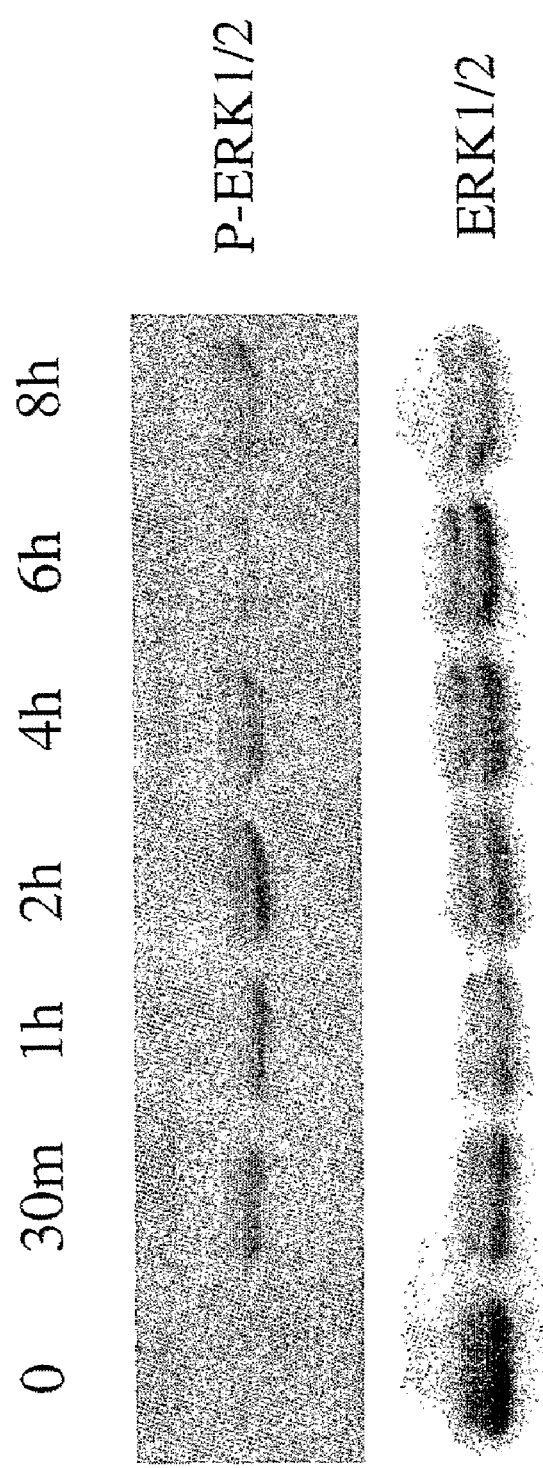
FIG. 19 shows that E2β induces membrane initiated estrogen signaling in ER-α66 negative breast cancer cells MDA-MB-231. Treatment of MDA-MB-231 cells with estradiol-17β (E2β) induced rapid phosphorylation of ERK1/2. Cells were treated with E2β (10 nM) for different time points, lysed and analyzed with Western blot using phosphorylation dependent and independent antibodies.

E2β Induces Membrane-initiated Estrogen Signaling in ER-α66 Negative MDA-MB-231 Cells To determine whether E2β induces membrane initiated estrogen signaling in ER-α66 negative MDA-MB-231, serum starved MDA-MB-231 cells were treated with 1 nM E2β for different time periods. For Western blot analysis, cells were disrupted with RIPA buffer, boiled in gel loading buffer and separated on a 10% SDS-PAGE gel. After electrophoresis, the proteins were transferred to a PVDF membrane (Millipore). The filter was probed with antibody against ERK1/2 (K-23) (Santa Cruz Biotechnology), or antibody used against the phosphorylated form of ERK1/2 (Cell Signaling Technology). As seen in FIG. 19, treatment of MDA-MB-231 cells with estradiol-17β (E2β) induced rapid phosphorylation of ERK1/2. These data strongly suggested that E2β stimulates activation of the MAPK pathway in ER-α66 negative MDA-MB-231 cells.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated monoclonal antibody that specifically binds to an amino acid sequence depicted at SEQ ID NO:1.

2. The antibody of claim 1 wherein the antibody is covalently attached to a compound.

3. The antibody of claim 2 wherein the compound is a chemotherapeutic agent.

4. The antibody of claim 2 wherein the compound is a detectable marker.

5. The antibody of claim 4 wherein the detectable marker is a fluorescent marker.

6. The antibody of claim 1 wherein the antibody specifically binds to an amino acid sequence depicted at amino acids 13-27 of SEQ ID NO:1.

7. A composition comprising an antibody of claim 1.

8. The composition of claim 7 further comprising a pharmaceutically acceptable carrier.

9. A method for making an antibody comprising administering to an animal a polypeptide comprising an amino acid sequence depicted at amino acids 13-27 of SEQ ID NO:1 or an immunogenic fragment thereof, and isolating the antibody from the animal, wherein the isolated antibody specifically binds to amino acids 13-27 of SEQ ID NO:1.

10. The method of claim 9 wherein the polypeptide or immunogenic fragment thereof is covalently attached to a carrier polypeptide.

11. A method for making an antibody comprising:
administering to an animal a polypeptide comprising an amino acid sequence depicted at amino acids 13-27 of SEQ ID NO:1 or an immunogenic fragment thereof;
obtaining from the animal a cell that produces the antibody;
making a monoclonal antibody-producing hybridoma using the cell; and
isolating a monoclonal antibody from the monoclonal antibody-producing hybridoma, wherein the isolated monoclonal antibody specifically binds to amino acids 13-27 of SEQ ID NO:1.

12. A polyclonal antibody produced by a method of claim 9.

13. A monoclonal antibody produced by a method of claim 11.

14. A method for detecting a polypeptide comprising:
providing a cell;
analyzing the cell for a polypeptide, wherein the polypeptide has a molecular weight of 36 kDa as measured following electrophoresis on a sodium dodecyl sulfate (SDS)-polyacrylamide gel, and is recognized by an isolated antibody that specifically binds to a polypeptide comprising the amino acid sequence depicted in SEQ ID NO:1; and
determining whether the cell expresses the polypeptide;
wherein analyzing the cell for a polypeptide comprises contacting the cell with an antibody that specifically binds to the amino acid sequence depicted at SEQ ID NO:1 or an immunogenic fragment thereof, and detecting the bound antibody.

15. The method of claim 14 wherein the cell is ex vivo.

16. The method of claim 15 wherein the cell is a tumor cell.

17. The method of claim 16 wherein the tumor is a breast tumor.

18. The method of claim 14 wherein the cell is in vivo.

19. The method of claim 18 wherein the cell is a tumor cell.

20. The method of claim 19 wherein the tumor is a breast tumor.

21. The method of claim 14 wherein the antibody is covalently attached to a detectable marker.

22. The method of claim 21 wherein the detectable marker is a fluorescent marker.

23. A kit comprising the isolated monoclonal antibody of claim 1, and a packaging material.

24. The isolated monoclonal antibody of claim 1, wherein the monoclonal antibody comprises a humanized monoclonal antibody.

25. The antibody of claim 24 wherein the antibody is covalently attached to a compound.

26. The antibody of claim 25 wherein the compound is a chemotherapeutic agent.

27. The antibody of claim 25 wherein the compound is a detectable marker.

28. The antibody of claim 27 wherein the detectable marker is a fluorescent marker.

29. The antibody of claim 24 wherein the antibody specifically binds to an amino acid sequence depicted at amino acids 13-27 of SEQ ID NO:1.

30. A composition comprising an antibody of claim 24.

31. The composition of claim 30 further comprising a pharmaceutically acceptable carrier.

32. The method of claim 14 wherein the isolated antibody comprises a monoclonal antibody.

33. The method of claim 32 wherein the monoclonal antibody comprises a humanized monoclonal antibody.

34. The kit of claim 23 wherein the monoclonal antibody comprises a humanized monoclonal antibody.

* * * * *

```
                         SEQUENCE LISTING

<160> NUMBER OF SEQ ID NOS: 27

<210> SEQ ID NO 1
<211> LENGTH: 27
<212> TYPE: PRT
<213> ORGANISM: Artificial Sequence
<220> FEATURE:
<223> OTHER INFORMATION: C-terminus of SEQ ID NO:20

<400> SEQUENCE: 1

Gly Ile Ser His Val Glu Ala Lys Lys Arg Ile Leu Asn Leu His Pro
1               5                   10                  15

Lys Ile Phe Gly Asn Lys Trp Phe Pro Arg Val
            20                  25

<210> SEQ ID NO 2
<211> LENGTH: 6
<212> TYPE: PRT
<213> ORGANISM: Artificial Sequence
<220> FEATURE:
<223> OTHER INFORMATION: carrier protein

<400> SEQUENCE: 2

Gln Phe Phe Gly Leu Met
1               5

<210> SEQ ID NO 3
<211> LENGTH: 10
<212> TYPE: PRT
<213> ORGANISM: Artificial Sequence
<220> FEATURE:
<223> OTHER INFORMATION: carrier protein

<400> SEQUENCE: 3

Glu Gln Lys Leu Ile Ser Glu Glu Asp Leu
1               5                   10

<210> SEQ ID NO 4
<211> LENGTH: 7
<212> TYPE: PRT
<213> ORGANISM: Artificial Sequence
<220> FEATURE:
<223> OTHER INFORMATION: carrier protein

<400> SEQUENCE: 4

Lys Ala Glu Asp Glu Ser Ser
1               5

<210> SEQ ID NO 5
<211> LENGTH: 9
<212> TYPE: PRT
<213> ORGANISM: Artificial Sequence
<220> FEATURE:
<223> OTHER INFORMATION: carrier protein

<400> SEQUENCE: 5

Tyr Pro Tyr Asp Val Pro Asp Tyr Ala
```

```
1               5

<210> SEQ ID NO 6
<211> LENGTH: 8
<212> TYPE: PRT
<213> ORGANISM: Artificial Sequence
<220> FEATURE:
<223> OTHER INFORMATION: carrier protein

<400> SEQUENCE: 6

Asp Tyr Lys Asp Asp Asp Asp Lys
1               5

<210> SEQ ID NO 7
<211> LENGTH: 11
<212> TYPE: PRT
<213> ORGANISM: Artificial Sequence
<220> FEATURE:
<223> OTHER INFORMATION: carrier protein

<400> SEQUENCE: 7

Tyr Thr Asp Ile Glu Met Asn Arg Leu Gly Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: carrier protein

<400> SEQUENCE: 8

Met Ala Ser Met Thr Gly Gly Gln Gln Met Gly
1               5                   10

<210> SEQ ID NO 9
<211> LENGTH: 6
<212> TYPE: PRT
<213> ORGANISM: Artificial Sequence
<220> FEATURE:
<223> OTHER INFORMATION: carrier protein

<400> SEQUENCE: 9

Asp Thr Tyr Arg Tyr Ile
1               5

<210> SEQ ID NO 10
<211> LENGTH: 6
<212> TYPE: PRT
<213> ORGANISM: Artificial Sequence
<220> FEATURE:
<223> OTHER INFORMATION: carrier protein

<400> SEQUENCE: 10

Thr Asp Phe Tyr Leu Lys
1               5

<210> SEQ ID NO 11
<211> LENGTH: 6
<212> TYPE: PRT
<213> ORGANISM: Artificial Sequence
<220> FEATURE:
<223> OTHER INFORMATION: carrier protein

<400> SEQUENCE: 11

His His His His His His
1               5
```

<210> SEQ ID NO 12

<400> SEQUENCE: 12

000

<210> SEQ ID NO 13
<211> LENGTH: 6
<212> TYPE: PRT
<213> ORGANISM: Artificial Sequence
<220> FEATURE:
<223> OTHER INFORMATION: carrier protein

<400> SEQUENCE: 13

Gln Tyr Pro Ala Leu Thr
1               5

<210> SEQ ID NO 14
<211> LENGTH: 11
<212> TYPE: PRT
<213> ORGANISM: Artificial Sequence
<220> FEATURE:
<223> OTHER INFORMATION: carrier protein

<400> SEQUENCE: 14

Gln Arg Gln Tyr Gly Asp Val Phe Lys Gly Asp
1               5                   10

<210> SEQ ID NO 15
<211> LENGTH: 6
<212> TYPE: PRT
<213> ORGANISM: Artificial Sequence
<220> FEATURE:
<223> OTHER INFORMATION: carrier protein

<400> SEQUENCE: 15

Glu Tyr Met Pro Met Glu
1               5

<210> SEQ ID NO 16
<211> LENGTH: 6
<212> TYPE: PRT
<213> ORGANISM: Artificial Sequence
<220> FEATURE:
<223> OTHER INFORMATION: carrier protein

<400> SEQUENCE: 16

Glu Phe Met Pro Met Glu
1               5

<210> SEQ ID NO 17
<211> LENGTH: 5
<212> TYPE: PRT
<213> ORGANISM: Artificial Sequence
<220> FEATURE:
<223> OTHER INFORMATION: carrier protein

<400> SEQUENCE: 17

Arg Tyr Ile Arg Ser
1               5

<210> SEQ ID NO 18
<211> LENGTH: 595
<212> TYPE: PRT
<213> ORGANISM: Homo Sapiens

<400> SEQUENCE: 18

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415
```

-continued

```
Cys Val Glu Gly Met Val Glu Ile Phe Asp Met Leu Leu Ala Thr Ser
        420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                    485                 490                 495
Leu Gln Gln Gln His Gln Arg Leu Ala Gln Leu Leu Leu Ile Leu Ser
                500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
        530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                    565                 570                 575
His Ser Leu Gln Lys Tyr Tyr Ile Thr Gly Glu Ala Glu Gly Phe Pro
                580                 585                 590
Ala Thr Val
        595

<210> SEQ ID NO 19
<211> LENGTH: 1788
<212> TYPE: DNA
<213> ORGANISM: Homo Sapiens

<400> SEQUENCE: 19
atgaccatga ccctccacac caaagcatct gggatggccc tactgcatca gatccaaggg      60
aacgagctgg agcccctgaa ccgtccgcag ctcaagatcc ccctggagcg gccccctggc     120
gaggtgtacc tggacagcag caagcccgcc gtgtacaact accccgaggg cgccgcctac     180
gagttcaacg ccgcggccgc cgccaacgcg caggtctacg gtcagaccgg cctcccctac     240
ggccccgggt ctgaggctgc ggcgttcggc tccaacggcc tggggggttt ccccccactc     300
aacagcgtgt ctccgagccc gctgatgcta ctgcaccccg cgccgcagct gtcgcctttc     360
ctgcagcccc acggccagca ggtgccctac tacctggaga cgagcccag cggctacacg      420
gtgcgcgagg ccgccgcc ggcattctac aggccaaatt cagataatcg cgccagggt       480
ggcagagaaa gattggccag taccaatgac aagggaagta tggctatgga atctgccaag     540
gagactcgct actgtgcagt gtgcaatgac tatgcttcag gctaccatta tggagtctgg     600
tcctgtgagg gctgcaaggc cttcttcaag agaagtattc aaggacataa cgactatatg     660
tgtccagcca ccaaccagtg caccattgat aaaaacagga ggaagagctg ccaggcctgc     720
cggctccgca aatgctacga agtgggaatg atgaaaggtg ggatacgaaa agaccgaaga     780
ggagggagaa tgttgaaaca caagcgccag agatgatg gggagggcag gggtgaagtg       840
gggtctgctg agacatgag agctgccaac ctttggccaa gcccgctcat gatcaaacgc      900
tctaagaaga acagcctggc cttgtccctg acgccgacc agatggtcag tgccttgttg      960
gatgctgagc cccccatact ctattccgag tatgatccta ccagacccett cagtgaagct    1020
```

```
tcgatgatgg gcttactgac caacctggca gacagggagc tggttcacat gatcaactgg    1080
gcgaagaggg tgccaggctt tgtggatttg accctccatg atcaggtcca ccttctagaa    1140
tgtgcctggc tagagatcct gatgattggt ctcgtctggc gctccatgga gcacccagtg    1200
aagctactgt ttgctcctaa cttgctcttg gacaggaacc agggaaaatg tgtagagggc    1260
atggtggaga tcttcgacat gctgctggct acatcatctc ggttccgcat gatgaatctg    1320
cagggagagg agtttgtgtg cctcaaatct attattttgc ttaattctgg agtgtacaca    1380
tttctgtcca gcaccctgaa gtctctggaa gagaaggacc atatccaccg agtcctggac    1440
aagatcacag acactttgat ccacctgatg gccaaggcag gcctgaccct gcagcagcag    1500
caccagcggc tggcccagct cctcctcatc ctctcccaca tcaggcacat gagtaacaaa    1560
ggcatggagc atctgtacag catgaagtgc aagaacgtgg tgccctcta tgacctgctg    1620 ctggagatgc tggacgccca ccgcctacat gcgcccacta gccgtggagg ggcatccgtg    1680
gaggagacga ccaaagcca cttggccact gcgggctcta cttcatcgca ttccttgcaa    1740
aagtattaca tcacggggga ggcagagggt ttccctgcca cagtctga                1788

<210> SEQ ID NO 20
<211> LENGTH: 310
<212> TYPE: PRT
<213> ORGANISM: Homo Sapiens

<400> SEQUENCE: 20

Met Ala Met Glu Ser Ala Lys Glu Thr Arg Tyr Cys Ala Val Cys Asn
1               5                   10                  15

Asp Tyr Ala Ser Gly Tyr His Tyr Gly Val Trp Ser Cys Glu Gly Cys
            20                  25                  30

Lys Ala Phe Phe Lys Arg Ser Ile Gln Gly His Asn Asp Tyr Met Cys
        35                  40                  45

Pro Ala Thr Asn Gln Cys Thr Ile Asp Lys Asn Arg Arg Lys Ser Cys
    50                  55                  60

Gln Ala Cys Arg Leu Arg Lys Cys Tyr Glu Val Gly Met Met Lys Gly
65                  70                  75                  80

Gly Ile Arg Lys Asp Arg Arg Gly Gly Arg Met Leu Lys His Lys Arg
                85                  90                  95

Gln Arg Asp Asp Gly Glu Gly Arg Gly Glu Val Gly Ser Ala Gly Asp
            100                 105                 110

Met Arg Ala Ala Asn Leu Trp Pro Ser Pro Leu Met Ile Lys Arg Ser
        115                 120                 125

Lys Lys Asn Ser Leu Ala Leu Ser Leu Thr Ala Asp Gln Met Val Ser
    130                 135                 140

Ala Leu Leu Asp Ala Glu Pro Pro Ile Leu Tyr Ser Glu Tyr Asp Pro
145                 150                 155                 160

Thr Arg Pro Phe Ser Glu Ala Ser Met Met Gly Leu Leu Thr Asn Leu
                165                 170                 175

Ala Asp Arg Glu Leu Val His Met Ile Asn Trp Ala Lys Arg Val Pro
            180                 185                 190

Gly Phe Val Asp Leu Thr Leu His Asp Gln Val His Leu Leu Glu Cys
        195                 200                 205

Ala Trp Leu Glu Ile Leu Met Ile Gly Leu Val Trp Arg Ser Met Glu
    210                 215                 220

His Pro Gly Lys Leu Leu Phe Ala Pro Asn Leu Leu Leu Asp Arg Asn
225                 230                 235                 240
```

```
Gln Gly Lys Cys Val Glu Gly Met Val Glu Ile Phe Asp Met Leu Leu
                245                 250                 255
Ala Thr Ser Ser Arg Phe Arg Met Met Asn Leu Gln Gly Glu Phe
            260                 265                 270
Val Cys Leu Lys Ser Ile Leu Leu Asn Ser Gly Ile Ser His Val
        275                 280                 285
Glu Ala Lys Lys Arg Ile Leu Asn Leu His Pro Lys Ile Phe Gly Asn
    290                 295                 300
Lys Trp Phe Pro Arg Val
305                 310
```

<210> SEQ ID NO 21
<211> LENGTH: 933
<212> TYPE: DNA
<213> ORGANISM: Homo Sapiens

<400> SEQUENCE: 21

```
atggctatgg aatctgccaa ggagactcgc tactgtgcag tgtgcaatga ctatgcttca    60
ggctaccatt atggagtctg gtcctgtgag ggctgcaagg ccttcttcaa gagaagtatt   120
caaggacata cgactatat gtgtccagcc accaaccagt gcaccattga taaaaacagg    180
aggaagagct gccaggcctg ccggctccgc aaatgctacg aagtgggaat gatgaaggt    240
gggatacgaa aagaccgaag aggagggaga atgttgaaac acaagcgcca gagagatgat   300
ggggagggca ggggtgaagt ggggtctgct ggagacatga gagctgccaa cctttggcca   360
agcccgctca tgatcaaacg ctctaagaag aacagcctgg ccttgtccct gacggccgac   420
cagatggtca gtgccttgtt ggatgctgag ccccccatac tctattccga gtatgatcct   480
accagaccct tcagtgaagc ttcgatgatg ggcttactga ccaacctggc agacagggag   540
ctggttcaca tgatcaactg ggcgaagagg gtgccaggct tgtggattt gaccctccat    600
gatcaggtcc accttctaga atgtgcctgg ctagagatcc tgatgattgg tctcgtctgg   660
cgctccatgg agcacccagg gaagctactg tttgctccta acttgctctt ggacaggaac   720
cagggaaaat gtgtagaggg catggtggag atcttcgaca tgctgctggc tacatcatct   780
cggttccgca tgatgaatct gcagggagag gagtttgtgt gcctcaaatc tattcttttg   840
cttaattctg gtatctcaca tgtagaagca aagaagagaa tcctgaactt gcatcctaaa   900
atatttggaa acaagtggtt cctcgtgtc taa                                  933
```

<210> SEQ ID NO 22
<211> LENGTH: 752
<212> TYPE: DNA
<213> ORGANISM: Homo Sapiens

<400> SEQUENCE: 22

```
ggtacccgcg cccgcgccgc ccgtcggggt ggccgccgcg cccggcagga gggagggagg    60
gagggaggga gaagggagag cctagggagc tgcgggagcc gcgggacgcg cgacccgagg   120
gtgcgcgcag ggagcccggg gcgcgcggcc cagcccgggg gttctgcgtg cagcccgcgc   180
tgcgttcaga gtcaagttct ctcgccgggc agctgaaaaa aacgtactct ccacccactt   240
accgtccgtg cgagaggcag acccgaaagc ccgggcttcc taacaaaaca cacgttggaa   300
aaccagacaa agcagcagtt atttgtgggg gaaaacacct ccaggcaaat aaacacgggg   360
cgctttgagt cacttgggaa ggtctcgctc ttgcattta agttgggggg tgtttggagt    420
tagcagagct cagcagagtt ttatttatcc ttttaatgtt tttgtttaat gtgctcccca   480
```

```
aatttccttt catctagact atttgattgg aaatatgtca gctatgatga tgactttctg    540
ggaagcgatt cctgtcaccc gctttcccct cctccccacc ccacgtcctg gggctttaga    600
gagcgattgg gagttgaatg ggtctgattt cggagttagc tggctgagtc cgcgctggag    660
cggattgctg gcatgtgact tctgacagcc ggaaatttgt aggtgtcccg cgagtttaaa    720
acaagccata tggaagcaca agtgcttaaa aa                                  752
```

```
<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
cggaattccg aagggaagta tggctatgga atcc                                34

<210> SEQ ID NO 24
<211> LENGTH: 31
<212> TYPE: DNA
<213> ORGANISM: Artificial Sequence
<220> FEATURE:
<223> OTHER INFORMATION: primer

<400> SEQUENCE: 24
cgggatccag aggctttaga cacgaggaaa c                                   31

<210> SEQ ID NO 25
<211> LENGTH: 4359
<212> TYPE: DNA
<213> ORGANISM: Homo Sapiens

<400> SEQUENCE: 25
ctggtatctc acatgtagaa gcaaagaaga gaatcctgaa cttgcatcct aaaatatttg     60
gaaacaagtg gtttcctcgt gtctaaagcc tctggtcata aggcctcaca gtatcctgca    120
gatcatcaaa tccgtgtgtg gacgtgggga cattttgttt tgaggcagtt acatgaccat    180
gggcaagtgg attggtctct ctggccttca gtttctcat ttgcaatgat tcaatggttt    240
gccttaaagt gtcttaagaa ggataggata gctacccaca aactttggat caaattttct    300
tcaaaacatc cttcccctga ctttaaaata tgccctggca accaacactc aacacccgta    360
gctagatgag ttataacaga gtgactgaag agagctccca caattcctag ttattaaata    420
cctgactaat tttcattagg agacatttaa gaactttagt gatgggaaga tttacatata    480
taattgatag tacaatctga cagagctgaa tagctcctgt ttgtcaactg ttaaattctt    540
tgtgcaatta ggtcaaagat caagatcaaa acaagggctg cccattgacc tgttcactcc    600
tgagaaaaat ggcaaaccat tgaatcataa atcatgacag ccaaaataat tttaggatat    660
taatgcaccc ctcatctttg caagtgagaa aactgaaggc cagagagact aatttacttg    720 cccattttg ataaaaatgt caccatttac agaatgtgga ctcctatgtt ggagtctgtt    780
gaaggacatg gcacatttaa cagcatcaga gcattttta ttaaaattta atttgtgcat    840
gacttctaat gctgaagaac gccaagctag gaagaagtca tgggctgaga tggggacaga    900
gagaacacac aatattcagt gactgtccgt gcagctggct gcccttgaaa atatccgaac    960
tatccactgg gaaaatgcct gtccccttgg ggtaattacc agagtttcaa catgcccaaa   1020
gctgcctcat cttcagggg aacttgttct agcgatttta gtatcaagaa gctaatggtc   1080
ccagggaaag ggttattttt aatatttagc tactgtgcta aaaatcacct aagtttctag   1140
```

```
agtcttggga aatttcataa gggaaagaac aaaggcaact tgttgactac ccactggtca    1200
ttctcctctg gtcttattac atacatggat gccagtttag attgtgttta tataggaaaa    1260
tttaaatgtg tgagcctcct taaggaacat catcaataca gatatatcag atagttctgt    1320
ccagcaaaaa acgtgcttat ttgctacaag taaatttta tttatttttc tcacttccct    1380
cactccttca aatttccagg taaatagctg cccaggagtt gcttcatctc tgtcccaaaa    1440
tacctagaca attgcgggat aaggagaatg gcagggaggg agtagtggct aaaatcacac    1500
ccttcaaaag aaagtgtgta ggacacacaa ttgtgagaag tctgaatgcc atgcacatag    1560
ggtatgactc actttgaaaa ttgtttataa tcaaggaaat gaaaatgagt taatttcgtg    1620
catgcatcat ttaaagccaa atgagaagaa acttctaatt tattttgtta cttttcggct    1680
aacactggca gtatgtaaca gatttatttt gcagaaacat ctagattgtc cgtgatcttg    1740
atcctgccct tatgtgtctt gtctttgaaa cccagtgttt cctggatata tggttcagga    1800
gacaagtttc cagaatcaag ttaggaccca ggtcttcttt ttttccaaac caaacattct    1860
tgctaatcct aaactacctg aggcagcctg tggtggcctc agctctaaaa ccattgttta    1920
aaggcttcta cccatcaatg gcccttcagc agagtggtac ggttaacggg gtagggtctg    1980
gagtcagggg agacctgggt tcaaatccta catctttaca cctctaatcc ccagtgtcct    2040
tgtctataaa ttgggaatat agccatgtca tgggattctt gtgagggtta aatgaggtaa    2100
aacacataca atgcttagca tgtatacaat taagcactaa ataattgaaa cacattaagt    2160
actaaatgaa tgtcagcagc ttatcactat tatctgtata atgataccaa gggtgtgccg    2220
actcataccc ttaggggttg gctggattcg gccttttctc tcgggaaaac atacctgatt    2280
tattaatagt gctttcaagc atgtgataaa tttctcaaac tgcctgtctt gttccctaga    2340
aacaccagga aggcctacct caaatagcaa cagagaaacc tatcggagcc ttaccctaca    2400
gctttccttg gggcacgggt gagcaatctg ccttagaggg gagaggctct gtgctgaggc    2460
tctttgaatg ctttgaataa atagatcccc agataatgaa aagacttcaa acaaattct    2520 acaagaaact gagtagtgtt tatagtgagg ccctagtgta catgcaaaaa accccccactg    2580 cccttgctta aatgtatctg attaacttga atacattttt aaatgagggc ttttttttccc    2640 tctttcagtg tttcggccag tcatttgcca cttctcattc catcttagtt ctctgtaaag    2700
aaggtgccag agacctaagg tgcccaaggc aattttgcat tttacaattc taagctttag    2760
aatgaagtca tcaatttgct acatccggac tacagtgcaa ttattccttt gccttgctgg    2820
aaattggagt gaaatctttc tagctgtcaa tttcaactca gttgcagtag tgttttgaag    2880
aattaatggc gataaggtta gaaaatttta agtcaaacgt agggaaaaag taccagctag    2940
accatcataa gcatttgctt tgaaagcatg cttctaaagt gtgtttaacc tcaaataaca    3000
gtcacaaata tggttattat gaatgtatgc acagatttt atgtttctaa ttttaagaag    3060
ttctagggag ctccctgtaa cgatttaggg aatctctaga ttctgatata ctgcaagtct    3120
tttaatggta ggaatcacat tgaattaatt ttgtaggccc agggcctaaa tttagtaggt    3180
gttcagtacc tattggcatc aattcatatg taggtttaaa atactgtatg aagatacaga    3240
atcaccacca tcaaatcaaa ttgaaatatg taacaggcta gtataatatt aacatctgac    3300
tttaaacaac aacaaagaaa ccaaatgagt aactcctccc ttcaaactaa tagtcagttt    3360
cttccaactc agtctctttc tcctctcagg aagaatgcgt atctaaaaat ttcccattgc    3420
agactgctgg aaacaacatt ctaaactatt tatgcttctg caataacctt tccaatttgc    3480
```

-continued

```
tggaccagtg caagattaaa cacgagatat ctcaagtctc aatgtaaagg aacaccacga    3540
cagcctggac tgtgggtgaa gttcattctt ccccagcaga ctctgccttt cattctcggg    3600
gttgggtgtg ccccaaacag aggtaccgac ggtaacgaag cccaagaatg ttcaaccaca    3660
acctgtctgt gaaggtgttg gatgacgttt gccattcagg tgaagattat ttatgttcca    3720
gtcccacctg agtagcaaag tgaacactgt gctgaatgct cagaaagatg ttaatgaacc    3780
gtgctggaca gagcagagct gaaaggcgcc ttgcgagtgt cgtagtgaga atgtggctgt    3840
cccagctgca aagccctgtt aggaggcatg aggaagcact tgctgcccta agaaacgatg    3900
ccttcgacat tttcaaaaga tctatgtggc tgtctgaaac aatgcggaga gcagatagac    3960
gcaatatttg ggaaccaaag agtgactgct gttggcgttg catcataaca taagcgcttt    4020
cccccttctc gtcactatca tttgtatcaa ccaaagaact gatctctggt atcctcgaag    4080
gaatgctgtg gggatattct tcatctctgt tcatggtaca tcagcaattt gtggggaaaa    4140
gatggactat ataacacaat gatctgccta aaagaaactg tctctactta taggggctg     4200 agcaaacctt agagcatctg cggatgctcg tcattatctt caaaagtccc caagagtttt    4260
tctccatact ttattattgc tattttgttt aggctagaaa aaaaaaaaac tcataaaatt    4320
gtcttcaaac caaaccaaag gaaaaaaaaa aaaaaaaa                             4359
```

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26

```
gcaaagaaga gaatcctgaa cttgcatcct                                        30
```

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27

```
ttagtcaggt atttaataac taggaattg                                         29
```